(12) United States Patent
Choi et al.

(10) Patent No.: US 11,117,892 B2
(45) Date of Patent: Sep. 14, 2021

(54) PYRROLO-PYRIDINE DERIVATIVE COMPOUND, METHOD FOR PREPARING SAME, AND PHARMACEUTICAL COMPOSITION CONTAINING SAME AS ACTIVE INGREDIENT FOR PREVENTION OR TREATMENT OF PROTEIN KINASE-RELATED DISEASES

(71) Applicants: DAEGU-GYEONGBUK MEDICAL INNOVATION FOUNDATION, Daegu (KR); KOREA RESEARCH INSTITUTE OF BIOSCIENCE AND BIOTECHNOLOGY, Daejeon (KR); DAEGU GYEONGBUK INSTITUTE OF SCIENCE AND TECHNOLOGY, Daegu (KR)

(72) Inventors: Hwan Geun Choi, Seoul (KR); Eunhwa Ko, Daegu (KR); Joong-heui Cho, Daegu (KR); Jung Beom Son, Daegu (KR); Yi Kyung Ko, Daegu (KR); Jin-Hee Park, Jeollanam-do (KR); So Young Kim, Daegu (KR); Seock Yong Kang, Seoul (KR); Seungyeon Lee, Daegu (KR); Hee Yoon Ryu, Daegu (KR); Nam Doo Kim, Daegu (KR); Sang Bum Kim, Daegu (KR); Sun-Hwa Lee, Daegu (KR); Dayea Kim, Daegu (KR); Sun Joo Lee, Daegu (KR); Sungchan Cho, Daejeon (KR); Kyu-Sun Lee, Daejeon (KR); Kweon Yu, Daejeon (KR); Miri Choi, Daejeon (KR); Ja Wook Koo, Daegu (KR); Hyang-Sook Hoe, Daegu (KR)

(73) Assignees: DAEGU-GYEONGBUK MEDICAL INNOVATION FOUNDATION; KOREA RESEARCH INSTITUTE OF BIOSCIENCE AND BIOTECHNOLOGY; DAEGU GYEONGBUK INSTITUTE OF SCIENCE AND TECHNOLOGY

( * ) Notice: Subject to any disclaimer, the term of this patent is extended or adjusted under 35 U.S.C. 154(b) by 0 days.

(21) Appl. No.: 16/495,455

(22) PCT Filed: Mar. 23, 2018

(86) PCT No.: PCT/KR2018/003459
§ 371 (c)(1),
(2) Date: Sep. 19, 2019

(87) PCT Pub. No.: WO2018/174650
PCT Pub. Date: Sep. 27, 2018

(65) Prior Publication Data
US 2020/0207756 A1 Jul. 2, 2020

(30) Foreign Application Priority Data

Mar. 23, 2017 (KR) .................. 10-2017-0036845

(51) Int. Cl.
C07D 471/04 (2006.01)
A61P 25/28 (2006.01)

(52) U.S. Cl.
CPC ............ *C07D 471/04* (2013.01); *A61P 25/28* (2018.01)

(58) Field of Classification Search
CPC ............................. C07D 471/04; A61P 25/28
See application file for complete search history.

(56) References Cited

U.S. PATENT DOCUMENTS

2014/0066406 A1  3/2014  Wang et al.

FOREIGN PATENT DOCUMENTS

| CN | 105940004 A | 9/2016 |
|---|---|---|
| CN | 1059980388 A | 9/2016 |
| KR | 1020160106623 A | 1/2015 |
| RU | 2434013 C2 | 7/2007 |
| WO | 2006127587 A1 | 11/2006 |
| WO | 2008129152 A1 | 10/2008 |
| WO | 2009032694 A1 | 3/2009 |
| WO | 2009032703 A1 | 3/2009 |
| WO | 2011090738 A2 | 7/2011 |
| WO | 2012135631 A1 | 10/2012 |
| WO | 2014170248 A1 | 10/2014 |
| WO | 2015113451 A1 | 8/2015 |
| WO | 2015113452 A1 | 8/2015 |
| WO | WO 2016195776 | * 12/2016 |

OTHER PUBLICATIONS

Iragavarapu. Journal of Hematology & Oncology, 2015, 8:17, 1-9 (Year: 2015).*
Kruczynski. Expert Opinion on Therapeutic Targets, 2012, 16(11), 1127-38 (Year: 2012).*
Michellys, et al., Design and synthesis of novel selective anaplastic lymphoma kinase inhibitors, Bioorganic & Medicinal Chemistry Letters 26 (2016) 1090-1096.

(Continued)

*Primary Examiner* — Noble E Jarrell
(74) *Attorney, Agent, or Firm* — Caesar Rivise, PC

(57) ABSTRACT

The present invention relates to a pyrrolo-pyridine derivative compound, a method for preparing the same, and a pharmaceutical composition containing the same as an active ingredient for the prevention or treatment of protein kinase-related diseases. A compound represented by chemical formula 1, an optical isomer thereof, or a pharmaceutically acceptable salt thereof, according to the present invention, has excellent inhibitory activity against various protein kinases including DYRK1A, and therefore, the pharmaceutical composition containing the same as an active ingredient can be favorably used in the treatment or prevention of protein kinase-related diseases. Particularly, the pharmaceutical composition can be effectively used in the prevention, treatment, or alleviation of Alzheimer's disease, dementia, or Alzheimer's dementia.

9 Claims, 32 Drawing Sheets

(56) References Cited

OTHER PUBLICATIONS

International Search Report of PCT/KR2018/003459 dated Mar. 23, 2018.
English translation of Abstract of RU Patent No. 2434013.
Qidong You, Medicinal Chemistry, Chemical Industry Press, Jan. 004, pp. 32-33, and English translation of article.
English Abstract of CN 1059980388A (WO2015113451).
English Abstract of CN 105940004A (WO2015/113452 A1).
Extended European Search Report for corresponding European Application No. EP18770572 dated Nov. 17, 2020.

* cited by examiner

Harmin

Harmin

57

57

$$\text{Novel object preference (\%)} = \frac{\text{Exploration time(ET) in novel object}}{\text{ET in novel object + ET in familiar object}} \times 100$$

PYRROLO-PYRIDINE DERIVATIVE COMPOUND, METHOD FOR PREPARING SAME, AND PHARMACEUTICAL COMPOSITION CONTAINING SAME AS ACTIVE INGREDIENT FOR PREVENTION OR TREATMENT OF PROTEIN KINASE-RELATED DISEASES

CROSS-REFERENCE TO RELATED APPLICATIONS

This application is a U.S. National Phase Application of PCT/KR2018/003459, filed Mar. 23, 2018, which claims priority to KR 10-2017-0036845, filed Mar. 23, 2017, the contents of which applications are incorporated herein by reference in their entireties for all purposes.

BACKGROUND OF THE INVENTION

1. Field of the Invention

The present invention relates to a pyrrolo-pyridine derivative compound, a preparation method thereof, and a pharmaceutical composition for use in preventing or treating protein kinase related disease as an active ingredient.

2. Description of the Related Art

Protein kinase is an enzyme that catalyses the reaction to transfer the terminal phosphate group of adenosine triphosphate (ATP) to a specific residue of protein (tyrosine, serine, threonine), and is involved in signals that regulate cell activation, growth, and differentiation according to extracellular mediators and environmental changes.

Inappropriately high protein kinase activity is directly or indirectly involved in various diseases resulting from abnormal cellular functions. For example, mutation, over-expression or failure of appropriate regulatory mechanism of kinases involved in inappropriate enzyme activity, or over-synthesis or deficiency of factors involved in upstream or downstream signal transduction of cytokines or kinases can cause disease. Therefore, selective inhibition of kinase activity can be a beneficial target for the development of new drugs for the treatment of disease.

Brain cancer is a general term for primary brain cancer that occurs in the brain tissue and the cerebral meninges surrounding the brain and secondary brain cancer that has metastasized from the skull or other parts of the body. Such brain cancer is distinguished from other cancers developed in other organs in many aspects. First, cancers developed in lung, stomach and breast are limited in one or two types of cancer for each organ and their properties are the same or similar. However, many different types of cancers can be developed in the brain. For example, polymorphic glioblastoma, malignant glioma, lymphoma, blastoma, and metastatic tumor can be developed in the brain.

Down syndrome is a disease caused by chromosome aberration, precisely caused by trisomy of human chromosome 21, which is characterized by such symptoms as mental retardation, learning disorder and memory loss, early onset of Alzheimer's disease and cranial facial disorder. In particular, it is believed that the changes in the expression levels of such genes that exist in a certain region called 'Down syndrome critical region DSCR)' of human chromosome 21 cause Down syndrome. DYRK1A (dual specificity tyrosine-phosphorylation-regulated kinase 1A) is a gene playing an important role in the development and function of the nerve center, and is also involved in phosphorylation of various proteins. This gene is particularly related to the symptoms like learning disorder, memory loss, synaptic flexibility change, abnormal cell cycle and neuropathological symptoms similar to Alzheimer's dementia. So, it is necessary to understand biochemical, functional and molecular biological effects of this protein for disclosing the pathogenesis of Down syndrome related diseases and for developing therapeutic agents for Down syndrome related neurodefective.

Down syndrome is the most frequent chromosome abnormality syndrome, which is diagnosed one out of 700 new born babies. Down syndrome occurs regardless of racial, environmental and socioeconomic differences. The incidence is higher when the mother is over 35 years old. If the mother is over 40 years old, the frequency is 1 per 100 newborns. There is no way to prevent such genetic abnormality in modern medicine. It is only possible to determine whether the fetus has Down syndrome through genetic testing before birth.

Down syndrome patients display the following common physical features. Symptoms appear in all the body, which causes behavioral development delay due to decreased brain function in children with Down syndrome. 30~40% of down syndrome patients are born with congenital heart disease such as heart valve abnormalities and have a high incidence of pneumonia, leukemia, bowel obstruction and enteritis due to decreased immunity. Most of symptoms can be treated or prevented due to the advancement of medical technology so that the average life span of Down syndrome patients is increasing to 50 years.

However, there have been no promising results produced so far regarding the development of a therapeutic agent for cerebral nervous system depression and neurodegenerative symptoms, and Piracetam known to improve cognitive ability has not been shown to be effective in children with Down syndrome (Lobaugh, N. J. et al. (2001). "Piracetam therapy does not enhance cognitive functioning in children with Down syndrome." Arch Pediatr Adolesc Med 155: 442-448). Therefore, it is an urgent request to develop a novel therapeutic agent based on the disclosure of the fundamental cause mechanism of cerebral nervous system abnormalities in patients with Down syndrome.

On the other hand, Alzheimer's disease (AD) is a progressive disease that progresses to senile dementia. This disease can be divided into late onset developed in aged people (over 65 years old) and early onset developed in people who are at the age between and 60. The pathological aspect is equal between these two types of disease above, but when the disease is early onset, the symptoms are more severe and more prevalent.

All the developed medicinal products including those in the course of study and development can delay the progress of Alzheimer's disease or are focused on the alleviation of the symptoms of Alzheimer's disease. In the recent two decades, drugs that can improve cognitive ability especially in patients in the early and intermediate stages of the disease have been developed, and these drugs have been currently used as the primary drugs to treat patients with Alzheimer's disease.

Particularly, acetylcholine esterase inhibitors (AchEI) and N-methyl-D-aspartate (NMDA) receptor antagonist are the examples of those drugs to treat AD, which are still aiming to alleviate the symptoms of the disease, rather than targeting the disease pathway.

Tacrine is the first generation acetylcholine esterase inhibitor (AchE1), which was first approved for its antidementia action. It is known that tacrine can delay the loss of cognitive function in about 30% of Alzheimer's disease patients in the early and intermediate stages by inhibiting the decomposition of acetylcholine generated in the brain. Even though tacrine has been known to delay the loss of cognitive function by inhibiting the decomposition of acetylcholine, the duration of action is short so that it has to be administered at least 4 times a day. In addition, it cannot prevent the degenerative changes of brain cells, which are the fundamental problems of Alzheimer's disease, and even worse it causes many liver related side effects, so that it is hardly used these days.

Donepezil, as the second generation cholinesterase inhibitor (ChE1) attracting our attention these days, was developed by Eisai Co., Japan and approved by FDA, USA, in the late 1996, and thus has been sold in over 30 countries since 1997. Donepezil can be taken once a day, and is able to inhibit selectively to reduce peripheral side effects. Rivastigmine is the drug developed by Novartis Co., USA and approved in December, 1997 in Switzerland and used in EU and South American countries. This drug is being prepared for approval in USA and Canada, and was introduced in Korea in September, 1997. Rivastigmine can be taken twice a day and has significantly reduced peripheral side effects due to its high specificity to the central nervous system. Rivastigmine is reported to have little hepatotoxicity since it is metabolized in the kidney. Metrifonate is undergoing a phase 3 clinical trial in dementia patients and has been reported to have a long duration of action as an irreversible AChEI.

The pathological characteristics of Alzheimer's disease include amyloid plaque generated by the deposition of amyloid-beta peptide (Aβ) and neurofibrillary tangle formed by the hyper-phosphorylation of tau protein which is functioning to stabilize microtubule.

Plaques are produced by the excessive accumulation of beta amyloid due to the over-production or metabolic abnormalities in Alzheimer's disease patients. The loss of neurons can be caused by toxicity of beta amyloid and plaque, resulting in cognitive impairment and memory impairment.

In the course of developing an inhibitor of the expression of DYRK1A, which is a cause of various diseases including cancer, Down syndrome, diabetes, Alzheimer's disease and dementia, the present inventors confirmed that the pyrrolopyridine derivative compound of the present invention was able to inhibit the DYRK1A expression efficiently, leading to the completion of the present invention.

SUMMARY OF THE INVENTION

It is an object of the present invention to provide a novel pyrrolo-pyridine derivative compound.

It is another object of the present invention to provide a preparation method of the pyrrolo-pyridine derivative compound.

It is another object of the present invention to provide a pharmaceutical composition for preventing or treating a disease selected from the group consisting of cancer, degenerative brain disease and metabolic disease.

It is also an object of the present invention to provide a health functional food composition for preventing or ameliorating a disease selected from the group consisting of cancer, degenerative brain disease and metabolic disease.

To achieve the above objects, the present invention provides a compound represented by chemical formula 1 below, an optical isomer thereof or a pharmaceutically acceptable salt thereof:

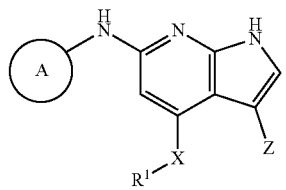

[Chemical Formula 1]

In chemical formula 1,

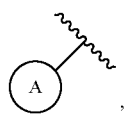

$R^1$, X and Z are as defined in this specification.

The present invention also provides a preparation method of a compound represented by chemical formula 1 comprising the following steps, as shown in reaction formula 1 below:

preparing a compound represented by chemical formula 4 by reacting a compound represented by chemical formula 2 with a compound represented by chemical formula 3 (step 1); and preparing a compound represented by chemical formula 1 by reacting the compound represented by chemical formula 4 prepared in step 1 above in the presence of an acid (step 2):

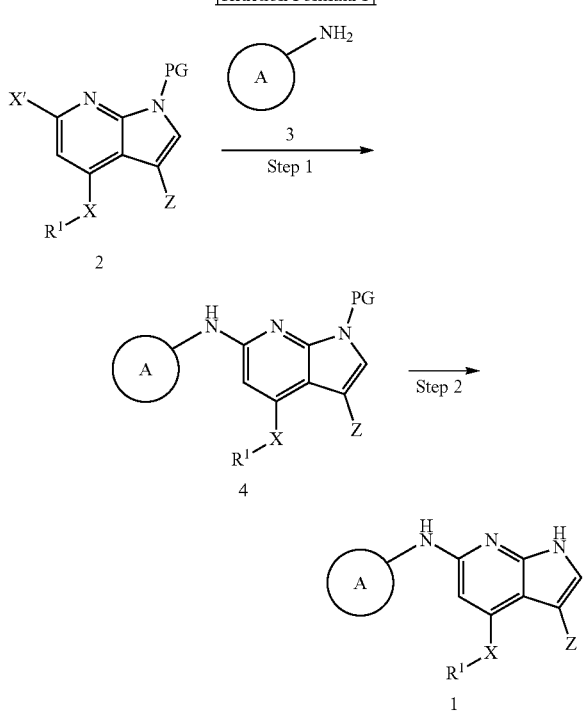

[Reaction Formula 1]

In reaction formula 1,

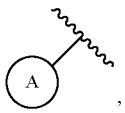

$R^1$, X, X', Z and PG are as defined in this specification.

The present invention also provides a pharmaceutical composition comprising a compound represented by chemical formula 1, an optical isomer thereof or a pharmaceutically acceptable salt thereof as an active ingredient for the prevention or treatment of protein kinase related disease.

The present invention also provides a pharmaceutical composition comprising a compound represented by chemical formula 1, an optical isomer thereof or a pharmaceutically acceptable salt thereof as an active ingredient for preventing or treating a disease selected from the group consisting of cancer, degenerative brain disease and metabolic disease.

The present invention also provides a health functional food composition comprising a compound represented by chemical formula 1, an optical isomer thereof or a pharmaceutically acceptable salt thereof as an active ingredient for preventing or ameliorating a disease selected from the group consisting of cancer, degenerative brain disease and metabolic disease.

The present invention also provides a method for preventing or treating a disease selected from the group consisting of cancer, degenerative brain disease and metabolic disease, which comprises the step of administering a pharmaceutical composition or a health functional food composition comprising a compound represented by chemical formula 1 or a pharmaceutically acceptable salt thereof as an active ingredient to a subject in need.

In addition, the present invention provides a use of the pharmaceutical composition or the health functional food composition above comprising a compound represented by chemical formula 1 or a pharmaceutically acceptable salt thereof as an active ingredient for preventing or treating a disease selected from the group consisting of cancer, degenerative brain disease and metabolic disease.

Advantageous Effect

The compound represented by chemical formula 1, the optical isomer thereof or the pharmaceutically acceptable salt thereof according to the present invention has an excellent activity of inhibiting various protein kinases including DYRK1A, so that a pharmaceutical composition comprising the same as an active ingredient can be effectively used for the prevention or treatment of protein kinase related disease. In particular, it can be effectively used for the prevention, treatment or amelioration of Alzheimer's disease, dementia or Alzheimer's dementia.

BRIEF DESCRIPTION OF THE DRAWINGS

FIG. 8 presents the changes of amyloid plaque by the compound of Example 57 in the Alzheimer's disease animal model.

FIG. 9 presents the results of evaluating short term cognitive improvement effect through behavioral tests. FIG. 10 presents the results of evaluating long term cognitive improvement effect through behavioral tests.

DESCRIPTION OF THE PREFERRED EMBODIMENTS

Figure 1A:
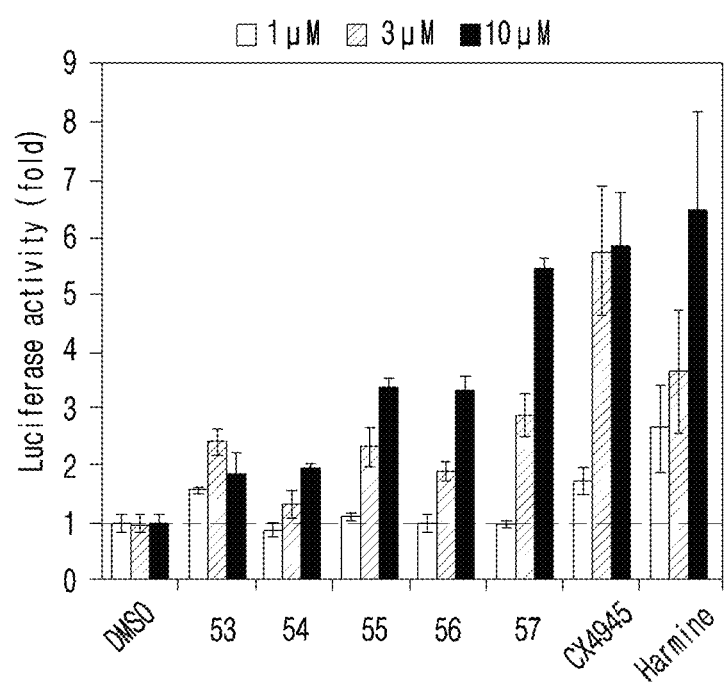
FIG. 1a is a graph illustrating the luciferase activity of DYRK1A affected by the compounds of Examples 53, 54, 55, 56 and 57.

Hereinafter, the present invention is described in detail.

The present invention provides a compound represented by chemical formula 1 below, an optical isomer thereof or a pharmaceutically acceptable salt thereof:

[Chemical Formula 1]

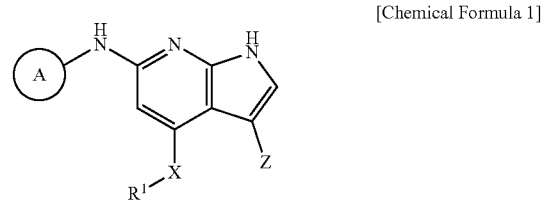

In chemical formula 1,

Z is cyano (—CN); or straight or branched $C_1$-$C_3$ alkyl substituted with one or more halogens;

X is —$NR^a$—, —O— or —S—, wherein $R^a$ is hydrogen or straight or branched $C_1$-$C_{10}$ alkyl, wherein, the alkyl can be substituted with one or more substituents selected from the group consisting of —OH and $C_1$-$C_3$ alkoxy;

$R^1$ is straight or branched $C_1$-$C_{10}$ alkyl, $C_3$-$C_8$ cycloalkyl or $C_{6-14}$ aryl, wherein, the alkyl or cycloalkyl can be substituted with one or more substituents selected from the group consisting of —OH, and, straight or branched $C_1$-$C_3$ alkyl and $C_1$-$C_3$ alkoxy, and the aryl can be substituted with one or more substituents selected from the group consisting of straight or branched $C_1$-$C_3$ alkyl and straight or branched $C_1$-$C_3$ alkoxy, nonsubstituted or substituted with one or more halogens;

or, $R^a$ can form nonsubstituted or substituted 5-8 membered heterocycloalkyl containing one or more heteroatoms selected from the group consisting of N, O and S along with $R^1$ and nitrogen atom to which they are attached, and the substituted heterocycloalkyl can be substituted with one or more substituents selected from the group consisting of straight or branched $C_1$-$C_6$ alkyl and straight or branched $C_1$-$C_6$ alkoxy; and

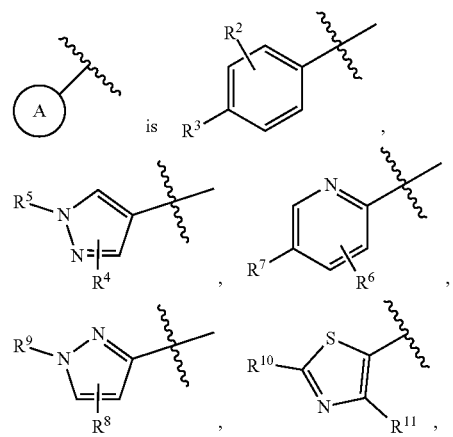

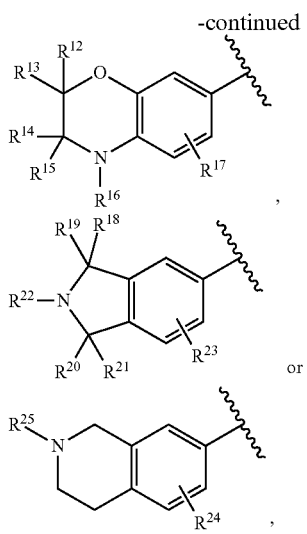

each $R^2$, $R^4$, $R^6$, $R^8$, $R^{11}$, $R^{17}$, $R^{23}$ and $R^{24}$ wherein, are independently one or more substituents selected from the group consisting of hydrogen, halogen, straight or branched $C_1$-$C_6$ alkyl and straight or branched $C_1$-$C_6$ alkoxy;

$R^3$, $R^5$, $R^7$ and $R^9$ are independently hydrogen; straight or branched $C_1$-$C_6$ alkyl or alkoxy; 3-8 membered heterocycloalkyl containing one or more heteroatoms selected from the group consisting of N and O; or —(C=O)NR$^{26}$R$^{27}$, wherein $R^{26}$ and $R^{27}$ are independently hydrogen, straight or branched $C_1$-$C_3$ alkyl or 3-8 membered heterocycloalkyl containing one or more heteroatoms selected from the group consisting of N and O substituted with 3-5 membered heterocycloalkyl containing one or more oxygen atoms, or $R^{26}$ and $R^{27}$ form 3-8 membered heterocycloalkyl containing one or more heteroatoms selected from the group consisting of N and O along with nitrogen atom to which they are attached, wherein, the alkyl or heterocycloalkyl is substituted with one or more substituents selected from the group consisting of —CN, halogen, straight or branched $C_1$-$C_3$ alkyl, and, 3-6 membered heterocycloalkyl containing one or more heteroatoms selected from the group consisting of N and O nonsubstituted or substituted with one or more straight or branched $C_1$-$C_3$ alkyl, $R^{10}$ is —CR$^{28}$R$^{29}$—CN, wherein $R^{28}$ and $R^{29}$ are independently hydrogen or straight or branched $C_1$-$C_3$ alkyl, $R^{12}$, $R^{13}$, $R^{14}$, $R^{15}$, $R^{18}$, $R^{19}$, $R^{20}$ and $R^{21}$ are independently hydrogen or straight or branched $C_1$-$C_3$ alkyl, or, two of $R^{12}$, $R^{13}$, $R^{14}$, $R^{15}$, $R^{18}$, $R^{19}$, $R^{20}$ and $R^{21}$ bonded to the same carbon can form carbonyl along with the carbon to which are attached, and $R^{16}$, $R^{22}$ and $R^{25}$ are independently hydrogen or straight or branched $C_1$-$C_3$ alkyl, wherein the alkyl can be substituted with one or more halogens.

In addition, Z is —CN or methyl substituted with one or more halogens;

X is —NR$^a$— or —O—, wherein R$^a$ is hydrogen or straight or branched $C_1$-$C_6$ alkyl, wherein, the alkyl can be substituted with one or more substituents selected from the group consisting of —OH and $C_1$-$C_3$ alkoxy;

$R^1$ is straight or branched $C_1$-$C_6$ alkyl, $C_3$-$C_8$ cycloalkyl or $C_{6-10}$ aryl, wherein, the alkyl can be substituted with one or more substituents selected from the group consisting of —OH, methyl and methoxy, and the aryl can be substituted with one or more substituents selected from the group consisting of methyl and methoxy, nonsubstituted or substituted with one or more halogens;

or, R$^a$ can form nonsubstituted or substituted 5-6 membered heterocycloalkyl containing one or more heteroatoms selected from the group consisting of N, O and S along with $R^1$ and nitrogen atom to which they are attached, and the substituted heterocycloalkyl can be substituted with one or more substituents selected from the group consisting of straight or branched $C_1$-$C_3$ alkyl and straight or branched $C_1$-$C_3$ alkoxy; and

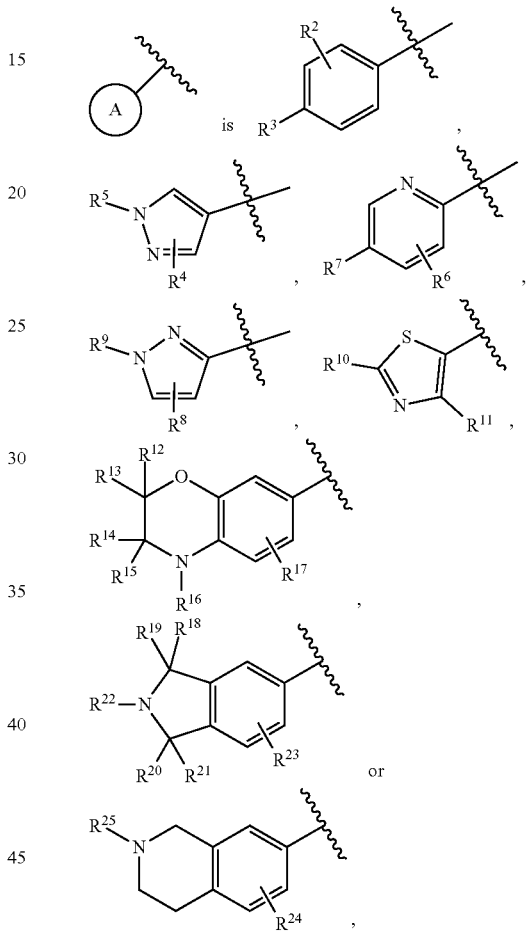

wherein, $R^2$, $R^4$, $R^6$, $R^8$, $R^{11}$, $R^{17}$, $R^{23}$ and $R^{24}$ are independently one or more substituents selected from the group consisting of hydrogen, halogen, straight or branched $C_1$-$C_3$ alkyl and straight or branched $C_1$-$C_3$ alkoxy;

$R^3$, $R^5$, $R^7$ and $R^9$ are independently hydrogen, straight or branched $C_1$-$C_3$ alkyl or alkoxy; morpholinyl, piperazinyl, piperidinyl or —(C=O)NR$^{26}$R$^{27}$, wherein $R^{26}$ and $R^{27}$ are independently hydrogen, methyl, morpholinyl, piperazinyl or piperidinyl, or $R^{26}$ and $R^{27}$ form morpholinyl, piperazinyl or piperidinyl along with nitrogen atom to which they are attached, wherein, the $C_1$-$C_3$ alkyl, morpholinyl, piperazinyl or piperidinyl can be substituted with one or more substituents selected from the group consisting of —CN, fluoro, oxetanyl, morpholinyl, piperazinyl, and, nonsubstituted or substituted with methyl piperidinyl, $R^{10}$ is —CR$^{28}$R$^{29}$—CN, wherein $R^{28}$ and $R^{29}$ are independently hydrogen, methyl or ethyl, $R^{12}$, $R^{13}$, $R^{14}$, $R^{15}$, $R^{18}$, $R^{19}$, $R^{20}$ and $R^{21}$ are independently hydrogen, methyl or ethyl, or, two of $R^{12}$, $R^{13}$, $R^{14}$, $R^{15}$, $R^{18}$, $R^{19}$, $R^{20}$ and $R^{21}$ bonded to the same carbon can form carbonyl along with the carbon to which they are attached, and $R^{16}$, $R^{22}$ and $R^{25}$ are independently hydrogen or, methyl nonsubstituted or substituted with one or more halogens or ethyl nonsubstituted or substituted with one or more halogens.

Further, Z is —CN or —CF$_3$;

X is —NR$^a$— or —O—, wherein R$^a$ is hydrogen or methyl;

$R^1$ is methyl, ethyl, n-propyl, isopropyl, cyclopropyl,

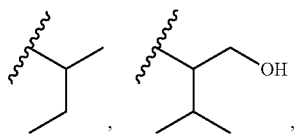

1-methylcyclopropyl, tetrahydropyranyl, tetrahydrofuranyl, or, phenyl substituted with one or more CF$_3$;

or, $R^a$ can form morpholinyl along with $R^1$ and nitrogen atom to which they are attached; and

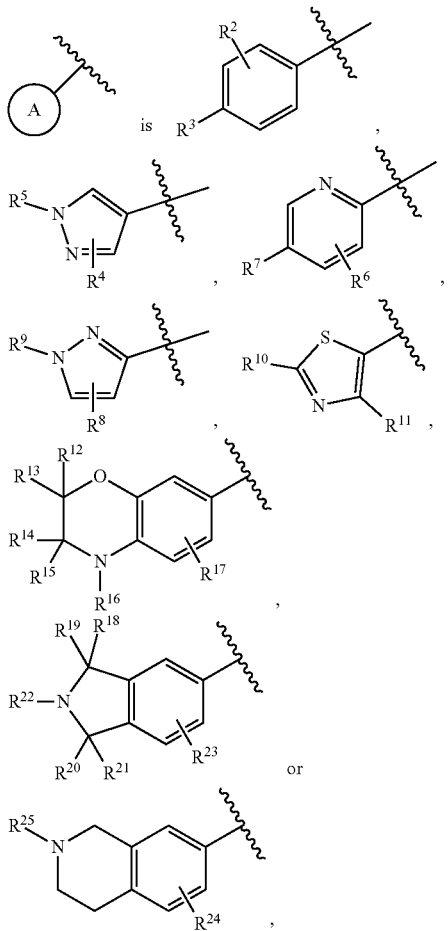

wherein, $R^2$, $R^4$, $R^6$, $R^8$, $R^{11}$, $R^{17}$, $R^{23}$ and $R^{24}$ are independently one or more substituents selected from the group consisting of hydrogen, chloro, fluoro, methyl and methoxy;

$R^3$ and $R^7$ are independently methoxy,

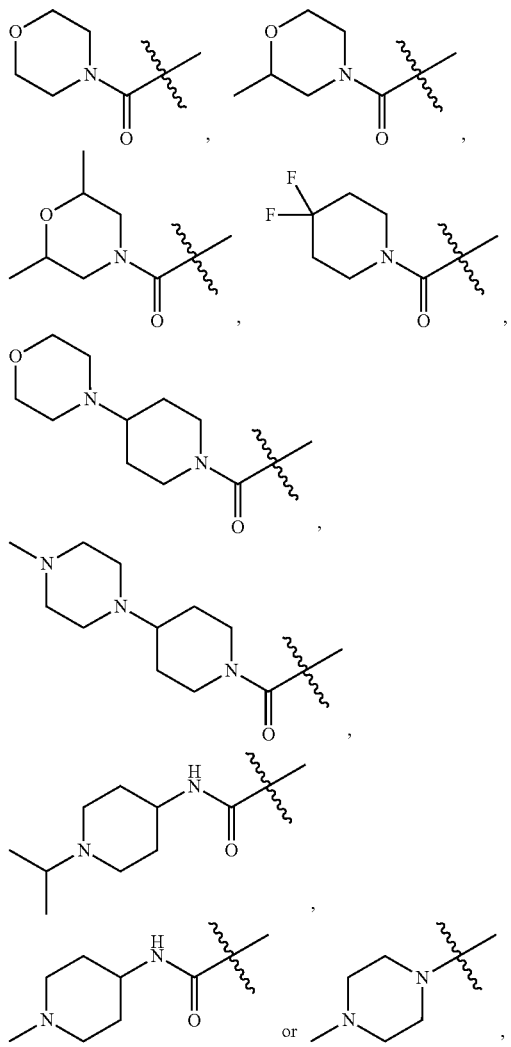

$R^5$ and $R^9$ are independently methyl, isopropyl,

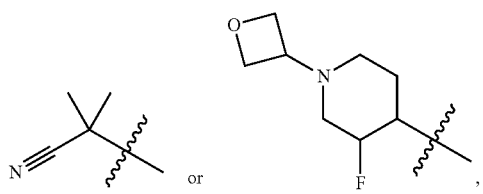

$R^{10}$ is —CR$^{28}$R$^{29}$—CN, wherein $R^{28}$ and $R^{29}$ are independently hydrogen or methyl, $R^{12}$, $R^{13}$, $R^{14}$, $R^{15}$, $R^{18}$, $R^{19}$, $R^{20}$ and $R^{21}$ are independently hydrogen or methyl, or, two of $R^{12}$, $R^{13}$, $R^{14}$, $R^{15}$, $R^{18}$, $R^{19}$, $R^{20}$ and $R^{21}$ bonded to the same carbon can form carbonyl along with the carbon to which they are attached, and $R^{16}$, $R^{22}$ and $R^{25}$ are independently hydrogen, or, methyl nonsubstituted or substituted with one or more halogens.

Furthermore, Z is —CN or —CF$_3$;

X is —NR$^a$— or —O—, wherein R$^a$ is hydrogen or methyl;

$R^1$ is methyl, ethyl, n-propyl, isopropyl, cyclopropyl,
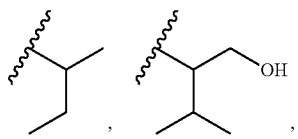
1-methylcyclopropyl, tetrahydropyran-4-yl or tetrahydrofuran-3-yl, or,
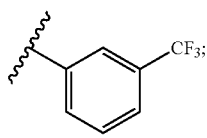 [SMILES: *c1cccc(C(F)(F)F)c1]
or, $R^a$ can form morpholinyl along with $R^1$ and nitrogen atom to which they are attached; and
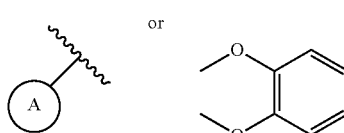
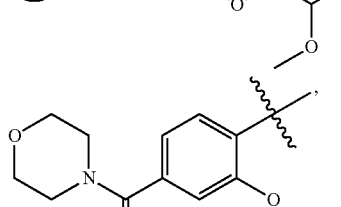
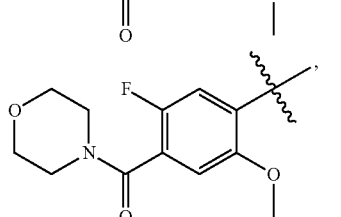
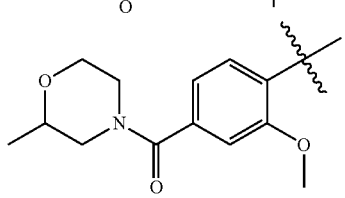
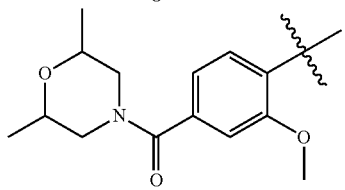
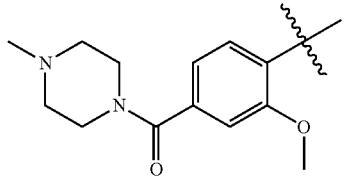
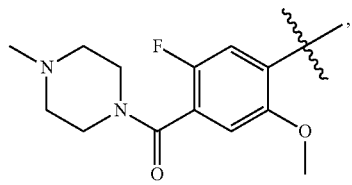
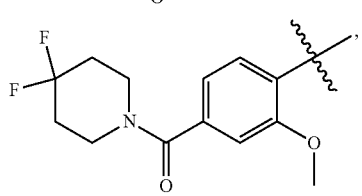
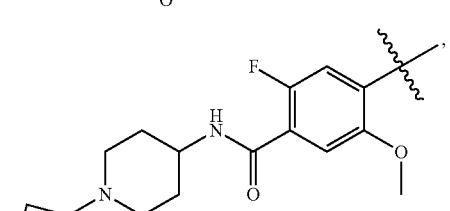
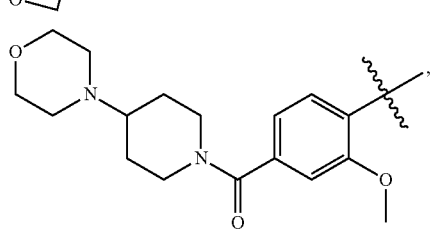
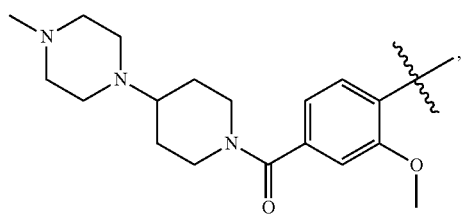
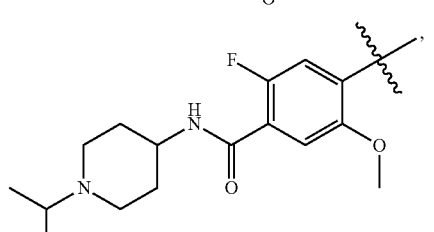
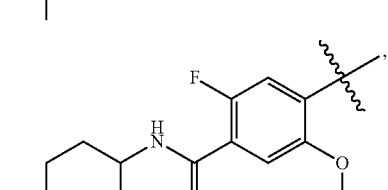
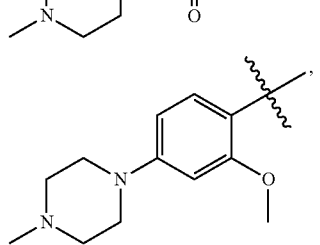

-continued

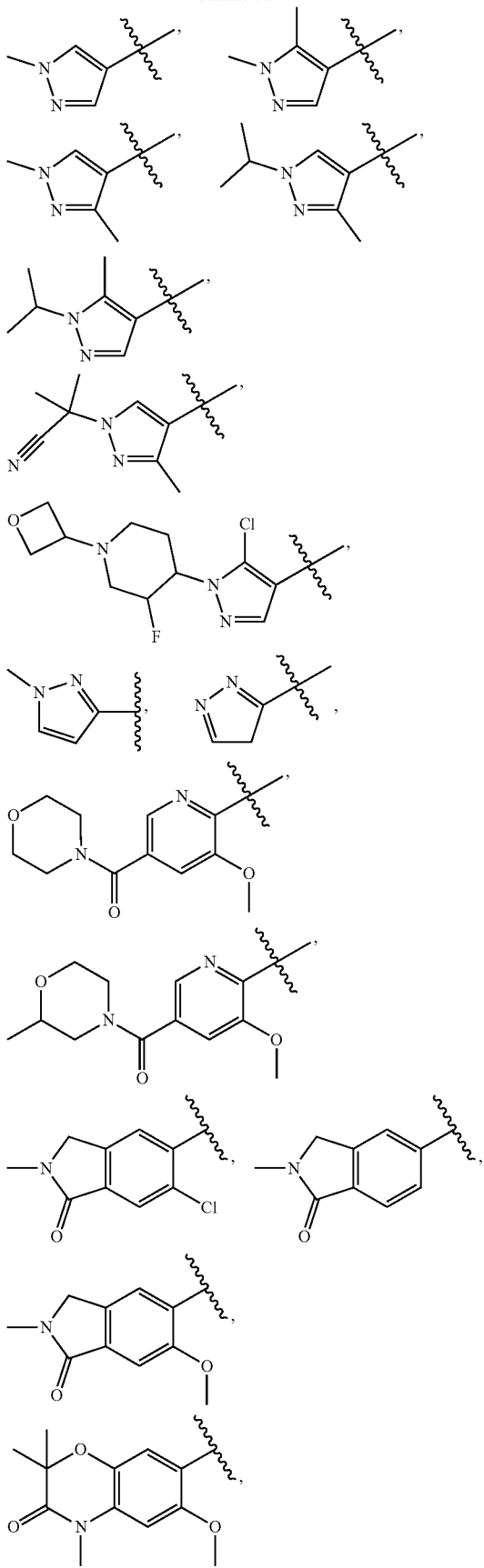

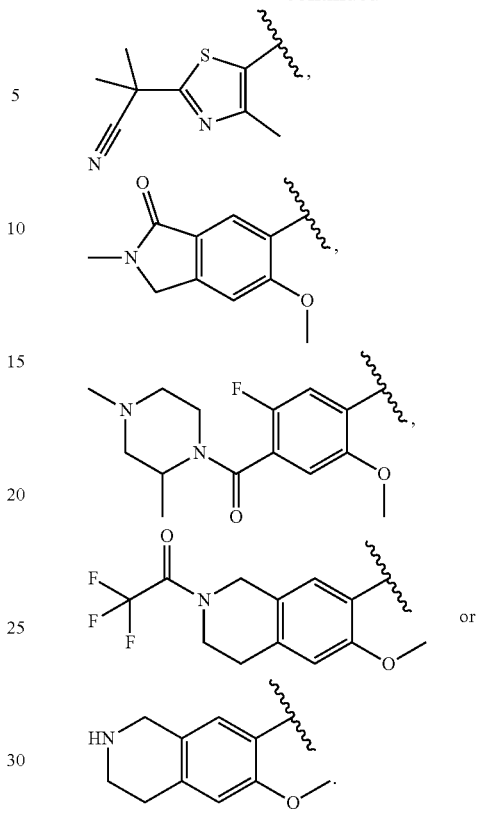

Further, the compound represented by chemical formula 1 above can be any one selected from the group consisting of the following compounds.

(1) 6-((2-methoxy-4-(morpholine-4-carbonyl)phenyl)amino)-4-(methylamino)-1H-pyrrolo[2,3-b]pyridine-3-carbonitrile; (2) 4-(ethylamino)-6-((2-methoxy-4-(morpholine-4-carbonyl)phenyl)amino)-1H-pyrrolo[2,3-b]pyridine-3-carbonitrile; (3) 6-((2-methoxy-4-(4-morpholinopiperidine-1-carbonyl)phenyl)amino)-4-((2-methoxyethyl)amino)-1H-pyrrolo[2,3-b]pyridine-3-carbonitrile; (4) 6-((2-methoxy-4-(morpholine-4-carbonyl)phenyl)amino)-4-((2-methoxyethyl)amino)-1H-pyrrolo[2,3-b]pyridine-3-carbonitrile; (5) 4-((2-methoxyethyl)amino)-6-((3,4,5-trimethoxyphenyl)amino)-1H-pyrrolo[2,3-b]pyridine-3-carbonitrile; (6) 4-((2-methoxyethyl)amino)-6-((1-methyl-1H-pyrazol-4-yl)amino)-1H-pyrrolo[2,3-b]pyridine-3-carbonitrile; (7) 4-((2-methoxyethyl)amino)-6-((1-methyl-1H-pyrazol-3-yl)amino)-1H-pyrrolo[2,3-b]pyridine-3-carbonitrile; (8) 4-(ethylamino)-6-((3,4,5-trimethoxyphenyl)amino)-1H-pyrrolo[2,3-b]pyridine-3-carbonitrile; (9) 6-((2-methoxy-4-(4-morpholinopiperidine-1-carbonyl)phenyl)amino)-4-(propylamino)-1H-pyrrolo[2,3-b]pyridine-3-carbonitrile; (10) 6-((2-methoxy-4-(morpholine-4-carbonyl)phenyl)amino)-4-(propylamino)-1H-pyrrolo[2,3-b]pyridine-3-carbonitrile; (11) 4-(propylamino)-6-((3,4,5-trimethoxyphenyl)amino)-1H-pyrrolo[2,3-b]pyridine-3-carbonitrile; (12) 6-((1-methyl-1H-pyrazol-4-yl)amino)-4-(propylamino)-1H-pyrrolo[2,3-b]pyridine-3-carbonitrile; (13) 6-((1-methyl-1H-pyrazol-3-yl)amino)-4-(propylamino)-1H-pyrrolo[2,3-b]pyridine-3-carbonitrile; (14) 4-(ethylamino)-6-((1-methyl-1H-pyrazol-4-yl)amino)-1H-pyrrolo[2,3-b]pyridine-3-carbonitrile; (15) 4-(ethylamino)-6-((1-methyl-1H-pyrazol-3-yl)amino)-1H-pyrrolo[2,3-b]pyridine-3-carbonitrile; (16) 6-((2-methoxy-4-(4-morpholinopiperidine-1-carbonyl)phenyl)amino)-4-(methylamino)-1H-pyrrolo[2,3-b]pyridine-3-carbonitrile; (17) 6-((5-fluoro-2-methoxy-4-(4-morpholinopiperidine-1-carbonyl)phenyl)amino)-4-(methylamino)-1H-pyrrolo[2,3-b]pyridine-3-carbonitrile; (18) 4-(ethylamino)-6-((2-methoxy-4-(4-morpholinopiperidine-1-carbonyl)phenyl)amino)-1H-pyrrolo[2,3-b]pyridine-3-carbonitrile; (19) 6-((5-fluoro-2-methoxy-4-(morpholine-4-carbonyl)phenyl)amino)-4-(methylamino)-1H-pyrrolo[2,3-b]pyridine-3-carbonitrile; (20) 6-((2-methoxy-4-(morpholine-4-carbonyl)phenyl)amino)-4-((2-methoxyethyl)(methyl)amino)-1H-pyrrolo[2,3-b]pyridine-3-carbonitrile; (21) 6-((5-fluoro-2-methoxy-4-(morpholine-4-carbonyl)phenyl)amino)-4-((2-methoxyethyl)(methyl)amino)-1H-pyrrolo[2,3-b]pyridine-3-carbonitrile; (22) (R)-6-((2-methoxy-4-(2-methylmorpholine-4-carbonyl)phenyl)amino)-4-(methylamino)-1H-pyrrolo[2,3-b]pyridine-3-carbonitrile; (23) (S)-6-((2-methoxy-4-(2-methylmorpholine-4-carbonyl)phenyl)amino)-4-(methylamino)-1H-pyrrolo[2,3-b]pyridine-3-carbonitrile; (24) 6-((4-((2R,6S)-2,6-dimethylmorpholine-4-carbonyl)-2-methoxyphenyl)amino)-4-(methylamino)-1H-pyrrolo[2,3-b]pyridine-3-carbonitrile; (25) 6-((4-(4,4-difluoropiperidine-1-carbonyl)-2-methoxyphenyl)amino)-4-(methylamino)-1H-pyrrolo[2,3-b]pyridine-3-carbonitrile; (26) (R)-4-(ethylamino)-6-((2-methoxy-4-(2-methylmorpholine-4-carbonyl)phenyl)amino)-1H-pyrrolo[2,3-b]pyridine-3-carbonitrile; (27) (S)-4-(ethylamino)-6-((2-methoxy-4-(2-methylmorpholine-4-carbonyl)phenyl)amino)-1H-Wpyrrolo[2,3-b]pyridine-3-carbonitrile; (28) 6-((4-((2R,6S)-2,6-dimethylmorpholine-4-carbonyl)-2-methoxyphenyl)amino)-4-(ethylamino)-1H-pyrrolo[2,3-b]pyridine-3-carbonitrile; (29) 6-((4-(4,4-difluoropiperidine-1-carbonyl)-2-methoxyphenyl)amino)-4-(ethylamino)-1H-pyrrolo[2,3-b]pyridine-3-carbonitrile; (30) 6-((1,3-dimethyl-1H-pyrazol-4-yl)amino)-4-(ethylamino)-1H-pyrrolo[2,3-b]pyridine-3-carbonitrile; (31) 6-((1,5-dimethyl-1H-pyrazol-4-yl)amino)-4-(ethylamino)-1H-pyrrolo[2,3-b]pyridine-3-carbonitrile; (32) 4-(ethylamino)-6-((1-isopropyl-3-methyl-1H-pyrazol-4-yl)amino)-1H-pyrrolo[2,3-b]pyridine-3-carbonitrile; (33) 4-(ethylamino)-6-((1-isopropyl-5-methyl-1H-pyrazol-4-yl)amino)-1H-pyrrolo[2,3-b]pyridine-3-carbonitrile; (34) 6-((1,5-dimethyl-1H-pyrazol-4-yl)amino)-4-(methylamino)-1H-pyrrolo[2,3-b]pyridine-3-carbonitrile; (35) 6-((1,3-dimethyl-1H-pyrazol-4-yl)amino)-4-(methylamino)-1H-pyrrolo[2,3-b]pyridine-3-carbonitrile; (36) 6-((1-isopropyl-3-methyl-1H-pyrazol-4-yl)amino)-4-(methylamino)-1H-pyrrolo[2,3-b]pyridine-3-carbonitrile; (37) 6-((1-isopropyl-5-methyl-1H-pyrazol-4-yl)amino)-4-(methylamino)-1H-pyrrolo[2,3-b]pyridine-3-carbonitrile; (38) 6-((1-(2-cyanopropan-2-yl)-3-methyl-1H-pyrazol-4-yl)amino)-4-(methylamino)-1H-pyrrolo[2,3-b]pyridine-3-carbonitrile; (39) 6-((3-methoxy-5-(morpholine-4-carbonyl)pyridin-2-yl)amino)-4-(methylamino)-1H-pyrrolo[2,3-b]pyridine-3-carbonitrile; (40) 4-(ethylamino)-6-((3-methoxy-5-(morpholine-4-carbonyl)pyridin-2-yl)amino)-1H-pyrrolo[2,3-b]pyridine-3-carbonitrile; (41) 6-((5-chloro-1-((3S,4S)-3-fluoro-1-(oxetan-3-yl)piperidin-4-yl)-1H-pyrazol-4-yl)amino)(methylamino)-1H-pyrrolo[2,3-b]pyridine-3-carbonitrile; (42) 6-((5-chloro-1-((3S,4S)-3-fluoro-1-(oxetan-3-yl)piperidin-4-yl)-1H-pyrazol-4-yl)amino)(ethylamino)-1H-pyrrolo[2,3-b]pyridine-3-carbonitrile; (43) (R)-4-(ethylamino)-6-((3-methoxy-5-(2-methylmorpholine-4-carbonyl)pyridin-2-yl)amino)-1H-pyrrolo[2,3-b]pyridine-3-carbonitrile; (44) (R)-6-((3-methoxy-5-(2-methylmorpholine-4-carbonyl)pyridin-2-yl)amino)-4-(methylamino)-1H-pyrrolo[2,3-b]pyridine-3-carbonitrile; (45) 3-methoxy-4-((4-morpholino-3-(trifluoromethyl)-1H-pyrrolo[2,3-b]pyridin-6-yl)amino)phenyl) (4-methylpiperazin-1-yl)methanone; (46) (3-methoxy-4-((4-morpholino-3-(trifluoromethyl)-1H-pyrrolo[2,3-b]pyridin-6-yl)amino)phenyl) (4-(4-methylpiperazin-1-yl)piperidin-1-yl)methanone; (47) 4-methoxy-6-((2-methoxy-4-(4-morpholinopiperidine-1-carbonyl)phenyl)amino)-1H-pyrrolo[2,3-b]pyridine-3-carbonitrile; (48) 4-methoxy-6-((2-methoxy-4-(morpholine-4-carbonyl)phenyl)amino)-1H-pyrrolo[2,3-b]pyridine-3-carbonitrile; (49) 4-ethoxy-6-((2-methoxy-4-(4-morpholinopiperidine-1-carbonyl)phenyl)amino)-1H-pyrrolo[2,3-b]pyridine-3-carbonitrile; (50) 4-ethoxy-6-((2-methoxy-4-(morpholine-4-carbonyl)phenyl)amino)-1H-pyrrolo[2,3-b]pyridine-3-carbonitrile; (51) (R)-6-((3-methoxy-5-(2-methylmorpholine-4-carbonyl)pyridin-2-yl)amino)-4-(1-methylcyclopropoxy)-1H-pyrrolo[2,3-b]pyridine-3-carbonitrile; (52) 6-((3-methoxy-5-(morpholine-4-carbonyl)pyridin-2-yl)amino)-4-(1-methylcyclopropoxy)-1H-pyrrolo[2,3-b]pyridine-3-carbonitrile; (53) $N^4$-ethyl-3-(trifluoromethyl)-$N^6$-(3,4,5-trimethoxyphenyl)-1H-pyrrolo[2,3-b]pyridine-4,6-diamine; (54) $N^4$-ethyl-$N^6$-(1-methyl-1H-pyrazol-3-yl)-3-(trifluoromethyl)-1H-pyrrolo[2,3-b]pyridine-4,6-diamine; (55) $N^4$-ethyl-$N^6$-(1-methyl-1H-pyrazol-4-yl)-3-(trifluoromethyl)-1H-pyrrolo[2,3-b]pyridine-4,6-diamine; (56) (4-((4-(ethylamino)-3-(trifluoromethyl)-1H-pyrrolo[2,3-b]pyridin-6-yl)amino)-3-methoxyphenyl) (morpholino)methanone; (57) (4-((4-(ethylamino)-3-(trifluoromethyl)-1H-pyrrolo[2,3-b]pyridin-6-yl)amino)-3-methoxyphenyl) (4-morpholinopiperidin-1-yl)methanone; (58) (3-methoxy-4-((4-(methylamino)-3-(trifluoromethyl)-1H-pyrrolo[2,3-b]pyridin-6-yl)amino)phenyl) (morpholino)methanone; (59) (3-methoxy-4-((4-(methylamino)-3-(trifluoromethyl)-1H-pyrrolo[2,3-b]pyridin-6-yl)amino)phenyl) (4-morpholinopiperidin-1-yl)methanone; (60) (2-fluoro-5-methoxy-4-((4-(methylamino)-3-(trifluoromethyl)-1H-pyrrolo[2,3-b]pyridin-6-yl)amino)phenyl) (4-methylpiperazin-1-yl)methanone; (61) (3-methoxy-4-((4-(methylamino)-3-(trifluoromethyl)-1H-pyrrolo[2,3-b]pyridin-6-yl)amino)phenyl) (4-(4-methylpiperazin-1-yl)piperidin-1-yl)methanone; (62) $N^6$-(2-methoxy-4-(4-methylpiperazin-1-yl)phenyl)-$N^4$-methyl-3-(trifluoromethyl)-1H-pyrrolo[2,3-b]pyridine-4,6-diamine; (63) (3-methoxy-4-((4-(methylamino)-3-(trifluoromethyl)-1H-pyrrolo[2,3-b]pyridin-6-yl)amino)phenyl) (4-methylpiperazin-1-yl)methanone; (64) (3-methoxy-4-((4-((2-methoxyethyl)amino)-3-(trifluoromethyl)-1H-pyrrolo[2,3-b]pyridine-6yl)amino)phenyl) (morpholino)methanone; (65) (3-methoxy-4-((4-((2-methoxyethyl)amino)-3-(trifluoromethyl)-1H-pyrrolo[2,3-b]pyridin-6-yl)amino)phenyl) (4-morpholinopiperidin-1-yl)methanone; (66) (3-methoxy-4-((4-((2-methoxyethyl)amino)-3-(trifluoromethyl)-1H-pyrrolo[2,3-b]pyridin-6-yl)amino)phenyl) (4-methylpiperazin-1-yl)-methanone; (67) (3-methoxy-4-((4-((2-methoxyethyl)amino)-3-(trifluoromethyl)-1H-pyrrolo[2,3-b]pyridin-6-yl)amino)phenyl) (4-(4-methylpiperazin-1-yl)piperidin-1-yl)methanone; (68) $N^6$-(2-methoxy-4-(4-methylpiperazin-1-yl)phenyl)-$N^4$-(2-methoxyethyl)-3-(trifluoromethyl)-1H-pyrrolo[2,3-b]pyridine-4,6-diamine; (69) $N^6$-(5-chloro-1-((3S,4S)-3-fluoro-1-(oxetan-3-yl)piperidin-4-yl)-1H-pyrazol-4-yl)-$N^4$-ethyl-3-(trifluoromethyl)-1H-pyrrolo[2,3-b]pyridine-4,6-diamine; (70) (4-(ethylamino)-3-(trifluoromethyl)-1H-pyrrolo[2,3-b]pyridin-6-yl)amino)-3-methoxyphenyl) (4-(4-methylpiperazin-1-yl)piperidin-1-yl)methanone; (71) 4-((4-(ethylamino)-3-(trifluoromethyl)-1H-pyrrolo[2,3-b]pyridin-6-yl)amino)-2-fluoro-5methoxy-N-(1-(oxetanepiperidin-4-yl)benzamide; (72) 4-((4-(ethylamino)-3-(trifluoromethyl)-1H-pyrrolo[2,3-b]pyridin-6-yl)amino)-2-fluoro-5-methoxy-N-(1-methylpiperidin-4- yl)benzylamide; (73) 2-fluoro-5-methoxy-4-((4-((2-methoxyethyl)amino)-3-(trifluoromethyl)-1H-pyrrolo[2,3-b]pyridin-6-yl)amino) (1-methylpiperidin-4-yl)benzamide; (74) 4-((4-(ethylamino-3-(trifluoromethyl)-1H-pyrrolo[2,3-b]pyridin-6-yl)amino)-2-fluoro-N-(1-isopropylpiperidin-4-yl)-5-methoxybenzamide; (75) (R)-(2,4-dimethylpiperazin-1-yl) (2-fluoro-5-methoxy-4-((4-(methylamino)-3-(trifluoromethyl)-1H-pyrrolo[2,3-b]pyridin-6-yl)amino) phenyl) methanone; (76) (3-methoxy-4-((4-morpholino-3-(trifluoromethyl)-1H-pyrrolo[2,3-b]pyridin-6-yl)amino) phenyl) (morpholino) methanone; (77) N-(5-chloro-1-((3S, 4S)-3-fluoro-1-(oxetan-3-yl)piperidin-4-yl)-1H-pyrazol-4-yl)-4-morpholino-3-(trifluoromethyl)-1H-pyrrolo[2,3-b]pyridine-6-amine; (78) N6-(5-chloro-1-((3S, 4S)-3-fluoro-1-(oxetan-3-yl)piperidin-4-yl)-1H-pyrazol-4-yl)-N4-methyl-3-(trifluoromethyl)-1H-pyrrolo[2,3-b]pyridine-4,6-diamine; (79) N6-(5-chloro-1-((3S, 4S)-3-fluoro-1-(oxetan-3-yl)piperidin-4-yl)-1H-pyrazol-4-yl)-3-methoxyethyl)-3-(trifluoromethyl)-1H-pyrrolo[2,3-b]pyridine-4,6-diamine; (80) 1-(6-((4-(ethylamino)-3-(trifluoromethyl)-1H-pyrrolo[2,3-b]pyridin-6-yl)amino)-7-methoxy-3,4-dihydroisoquinolin-2(1H)-yl)-2,2,2-trifluoroethan-1-one; (81) N4-ethyl-N6-(7-methoxy-1,2,3,4-tetrahydroisoquinolin-6-yl)-3-(trifluoromethyl)-1H-pyrrolo[2,3-b]pyridine-4,6-diamine; (82) (3-methoxy-4-((4-morpholino-3-(trifluoromethyl)-1H-pyrrolo[2,3-b]pyridin-6-yl)amino)phenyl) (4-methylpiperazin-1-yl)methanone; (83) (3-methoxy-4-((4-morpholino-3-(trifluoromethyl)-1H-pyrrolo[2,3-b]pyridin-6-yl) amino) phenyl) (4-(4-methylpiperazin-1-yl) piperidin-1-yl) methanone; (84) (3-methoxy-4-(3-(trifluoromethyl)-4-(3-(trifluoromethyl)phenylamino)-1H-pyrrolo[2,3-b]pyridin-6-ylamino)phenyl) (morpholino)methanone; (85) (3-methoxy-4-(3-(trifluoromethyl)-4-(3-(trifluoromethyl) phenylamino)-1H-pyrrolo[2,3-b]pyridin-6-ylamino)phenyl) (4-morpholinopiperidin-1-yl)methanone; (86) N6-(5-chloro-1-((3S, 4S)-3-fluoro-1-(oxetan-3-yl)piperidin-4-yl)-1H-pyrazol-4-yl)-3-(trifluoromethyl)-N4-(3-(trifluoromethyl)phenyl)-1H-pyrrolo[2,3-b]pyridine-4,6-diamine; (87) (3-methoxy-4-((4-methoxyethyl)(methyl)amino)-3-(trifluoromethyl)-1H-pyrrolo[2,3-b]pyridin-6-yl)amino)phenyl) (morpholino)methanone; (88) (3-methoxy-4-((4-methoxyethyl)(methyl)amino)-3-(trifluoromethyl)-1H-pyrrolo[2,3-b]pyridin-6-yl) amino)phenyl) ((4-morpholinopiperidin-1-yl) methanone; (89) N6-(5-chloro-1-((3S,4S)-3-fluoro-1-(oxetan-3-yl)piperidin-4-yl)-1H-pyrazol-4-yl) methoxyethyl)-N4-methyl-3-(trifluoromethyl)-1H-pyrrolo[2,3-b]pyridine-4,6-diamine; (90) (4-(4-(isopropylamino)-3-(trifluoromethyl)-1H-pyrrolo[2,3-b]pyridin-6-ylamino)-3-methoxyphenyl) (4-morpholinopiperidin-1-yl)methanone; (91) (R)-(4-((4-((1-hydroxy-3-methylbutan-2-yl)amino)-3-(trifluoromethyl)-1H-pyrrolo[2,3-b]amino)-3-methoxyphenyl) (4-morpholinopiperidin-1-yl)methanone; (92) (R)-(4-((4-((1-hydroxy-3-methylbutan-2-yl) amino)-3-(trifluoromethyl)-1H-pyrrolo[2,3-b]amino)-3-methoxyphenyl) (morpholino)methanone; (93) (S)-(4-((4-(2-butylamino)-3-(trifluoromethyl)-1H-pyrrolo[2,3-b]pyridin-6-yl)amino)-3-methoxyphenyl) (4-morpholinopiperidin-1-yl)-methanone; (94) (4-((4-(cyclopropylamino)-3-(trifluoromethyl)-1-((2-(trimethylsilyl)ethoxy)methyl)-1H-pyrrolo[2,3-b]pyridin-6-yl)-3-methoxyphenyl) (4-morpholinopiperidin-1-yl)methanone; (95) (4-((4-(cyclopropylamino)-3-(trifluoromethyl)-1H-pyrrolo[2,3-b]pyridin-6-yl)amino)-3-methoxyphenyl) (morpholino) methanone; (96) 5-((4-(ethylamino)-3-(trifluoromethyl)-1H-pyrrolo[2,3-b]pyridin-6-yl) amino)-6-methoxy-2-methylisoindolin-1-one; (97) 7-((4-(ethylamino)-3-(trifluoromethyl)-1H-pyrrolo[2,3-b]pyridin-6-yl)amino)-6-methoxy-2,2,4-trimethyl-2H-benzo[1,4]oxazin-3(4H)-1-one; (98) 6-((4-(ethylamino)-3-(trifluoromethyl)-1H-pyrrolo[2,3-b]pyridin-6-yl) amino)-5-methoxy-2-methylisoindolin-1-one; (99) 4-(ethylamino)-6-((6-methoxy-2-methyl-3-oxoisoindol-5-yl)amino)-1H-pyrrolo[2,3-b]pyridine-3-carbonitrile; (100) 6-((2(2-cyanopropan-2-yl)-4-methylthiazol-5-yl)amino)-4-(ethylamino)-1H-pyrrolo[2,3-b]pyridine-3-carbonitrile; (101) (6-chloro-5-((4-(ethylamino)-3-(trifluoromethyl)-1H-pyrrolo[2,3-b]pyridin-6-yl) amino)-2-methylisoindolin-1-one; (102) 5-((4-(ethylamino)-3-(trifluoromethyl)-1H-pyrrolo[2,3-b]pyridin-6-yl)amino)-2-methylisoindolin-1-one; (103) 4-(ethylamino)-6-((2-methyl-1-oxoisoindol-5-yl)amino)-1H-pyrrolo[2,3-b]pyridine-3-carbonitrile; (104) 6-((6-chloro-2-methyl-1-oxoisoindolin-5-yl)amino)-4-(ethylamino)-1H-pyrrolo[2,3-b]pyridine-3-carbonitrile; and (105) 4-(ethylamino)-6-((6-methoxy-2,2,4-trimethyl-3-oxo-3,4-dihydro-2H-benzo[b][1,4]oxazin-7-yl)amino)-1H-pyrrolo[2,3-b]pyridine-3-carbonitrile.

The compound represented by chemical formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by chemical formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The compound represented by chemical formula 1 according to the present invention, an optical isomer thereof or a pharmaceutically acceptable salt thereof is excellent in inhibiting DYRK1A kinase activity and has also been confirmed to have excellent DYRK1A kinase inhibitory activity at the cellular level through DYRK1A high dependent calcienurin/NFAT signaling experiment. In addition, the compound of the present invention is excellent in inhibiting phosphorylation of Tau, known as an important factor of Down syndrome, and in inhibiting DYRK1A in vivo, confirmed by in vivo experiments. Therefore, the compound represented by chemical formula 1 according to the present invention, an optical isomer thereof or a pharmaceutically acceptable salt thereof can be effectively used for the treatment or prevention of DYRK1A related disease (see Experimental Examples 1~5).

The compound represented by chemical formula 1 according to the present invention, an optical isomer thereof or a pharmaceutically acceptable salt thereof has the activity of inhibiting not only DYRK1A kinase but also other kinases such as ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK or YSK4, so that it can be effectively used for the treatment of ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK or YSK4 related disease as well (see Experimental Example 6).

The compound represented by chemical formula 1 of the present invention displays an effect of alleviating Alzheimer's disease, so that it can be effectively used for the treatment of Alzheimer's dementia (see Experimental Examples 7~9).

The compound represented by chemical formula 1 of the present invention can improve the short term cognitive decline caused by Alzheimer's disease, so that it can be effectively used for the treatment of Alzheimer's dementia (see Experimental Example 10).

The compound represented by chemical formula 1 of the present invention can also improve the long term cognitive decline caused by Alzheimer's disease, so that it can be effectively used for the treatment of Alzheimer's dementia (see Experimental Example 11).

In addition, the present invention provides a preparation method of a compound represented by chemical formula 1 comprising the following steps, as shown in reaction formula 1 below:

preparing a compound represented by chemical formula 4 by reacting a compound represented by chemical formula 2 with a compound represented by chemical formula 3 (step 1); and preparing a compound represented by chemical formula 1 by reacting the compound represented by chemical formula 4 prepared in step 1 above in the presence of an acid (step 2):

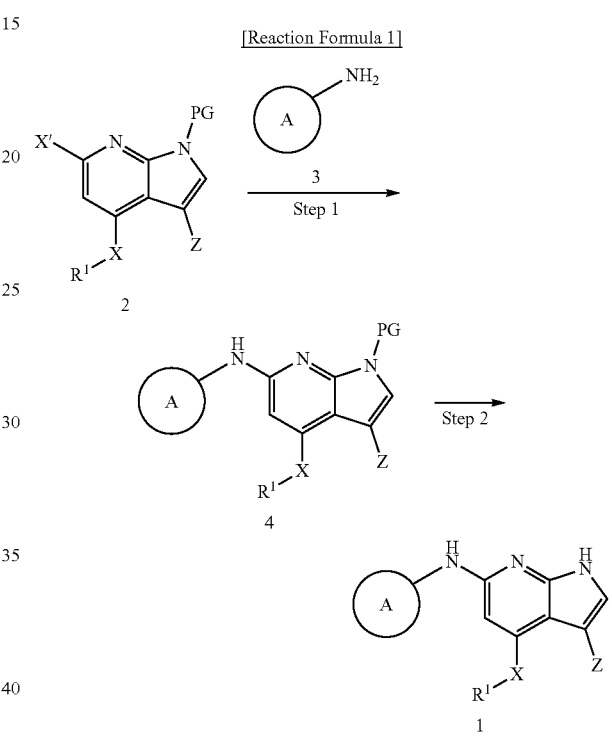

[Reaction Formula 1]

In reaction formula 1, X, Z, $R^1$ and

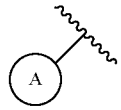

are as defined in chemical formula 1 above;

X' is halogen; and

PG is (2-(trimethylsilyl)methoxy)methyl (SEM), t-butyloxycarbonyl (BOC), carbobenzyloxy (Cbz), 9-fluorenylmethyloxycarbonyl (Fmoc), acetyl (Ac), benzoyl (Bz), benzyl (Bn), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), aryloxycarbonyl (Alloc) or p-methoxybenzyl (PMB).

Hereinafter, the preparation method according to the present invention is described in more detail.

In the preparation method of the present invention, step 1 is to prepare a compound represented by chemical formula 4 by reacting a compound represented by formula 2 with a compound represented by chemical formula 3.

As a preferable example of step 1, a compound represented by chemical formula 2 and a compound represented by chemical formula 3 are dissolved in a solvent in the presence of a base and then gas is eliminated by ultrasonic treatment. A palladium catalyst and Xphos are added to the prepared reaction mixture at 100° C., followed by reaction for 2 hours.

At this time, the base herein can be selected from the group consisting of such inorganic bases as cesium carbonate, sodium t-butoxide, potassium t-butoxide, sodium hydroxide, sodium carbonate, potassium carbonate and sodium hydride; and such organic bases as N,N-diaisopropylethylamine (DIPEA), 1,8-diazabicyclo[5.4.0]-7-undecene (DBU), pyridine and triethylamine. The selected base can be used in an equivalent amount or excess amount, alone or in combination. Herein, it is preferable to use potassium carbonate.

The palladium catalyst can be exemplified by tris(dibenzylideneacetone)palladium ($Pd_2(dba)_3$), tetrakis(triphenylphosphine)palladium ($Pd(Ph_3P)_4$), palladium charcoal (Pd—C), bis(triphenylphosphine)palladium dichloride ($PdCl_2$ $(PPh_3)_2$), [1,1-bis(diphenylphosphino)ferrocene]dichloropalladium ($PdCl_2$(dppf)), allylpalladium chloride dimer ([PdCl(allyl)]$_2$), palladium acetate (Pd(OAc)$_2$) and palladium chloride ($PdCl_2$), among which tris(dibenzylideneacetone)palladium ($Pd_2(dba)_3$) is preferred.

The reaction solvent usable herein is exemplified by toluene, dimethylacetamide (DMA), dimethylformamide (DMF), dimethylsulfoxide (DMSO), methylenechloride, dichloroethane, water, ethylacetate, acetonitrile; lower alcohols including isopropanol, methanol, ethanol, propanol and butanol; and ether solvents including tetrahydrofuran (THF), dioxane, ethylether and 1,2-dimethoxyethane, which can be used independently or together, and sec-butanol is more preferred herein.

After the reaction, the reaction mixture can be filtered with a filtration membrane and washed with an organic solvent. The solid compound 4 obtained after the concentration of the filtrate can be used in the next step without further purification.

At this time, the reaction solvent is exemplified by toluene, dimethylacetamide (DMA), dimethylformamide (DMF), dimethylsulfoxide (DMSO), methylenechloride, dichloroethane, water, ethylacetate, acetonitrile; lower alcohols including isopropanol, methanol, ethanol, propanol and butanol; and ether solvents including tetrahydrofuran (THF), dioxane, ethylether and 1,2-dimethoxyethane, which can be used independently or together, and EtOAc (ethyl acetate) and MeOH (methanol) are more preferred herein.

Next step (step 2) is to prepare a compound represented by chemical formula 1 by reacting the compound represented by chemical formula 4 prepared in step 1 above in the presence of an acid.

As a preferable example of step 2, a compound represented by chemical formula 3 was dissolved in dichloromethane, to which TFA (trifluoroacetic acid) was added at room temperature. After 4 hours of the reaction, the solvent was removed. Then, the concentrated mixture was dissolved in an organic solvent again. A base was added thereto at room temperature, followed by reaction for 14 hours.

At this time, the base herein can be selected from the group consisting of such inorganic bases as cesium carbonate, sodium t-butoxide, potassium t-butoxide, sodium hydroxide, sodium carbonate, potassium carbonate and sodium hydride; and such organic bases as N,N-diaisopropylethylamine (DIPEA), 1,8-diazabicyclo[5.4.0]-7-undecene (DBU), pyridine and triethylamine. The selected base can be used in an equivalent amount or excess amount, alone or in combination. Herein, it is preferable to use saturated potassium carbonate.

Upon completion of the reaction, the reaction product was diluted in EtOAc (ethyl acetate), followed by washing with water and brine stepwise. The organic layer was dried over $MgSO_4$ (magnesium sulfate). Then, the reaction mixture was purified by prep-HPLC and as a result a solid compound 1 was obtained.

The present invention also provides a pharmaceutical composition comprising a compound represented by chemical formula 1, an optical isomer thereof or a pharmaceutically acceptable salt thereof as an active ingredient for preventing or treating a disease selected from the group consisting of cancer, degenerative brain disease and metabolic disease.

The compound represented by chemical formula 1 above can inhibit the protein kinase activity.

At this time, the protein kinase can be ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK or YSK4.

The degenerative brain disease herein can be Alzheimer's disease, Down syndrome, Parkinson's disease, Lou Gehrig's disease, dementia, Huntington's disease, multiple sclerosis, proximal lateral sclerosis, apoplexy, stroke or mild cognitive impairment.

The said dementia can be Alzheimer's dementia, cerebrovascular dementia, dementia caused by head injury, multi-infarct dementia, Alzheimer's/multi-infarction dementia or alcoholic dementia.

The metabolic disease herein can be diabetes, hypoglycemia, hypercholesterolemia, hyperlipidemia, hemochromatosis, amyloidosis or porphyria.

The cancer can be brain cancer, brain tumor, benign astrocytoma, malignant astrocytoma, pituitary adenoma, meningioma, brain lymphoma, oligodendroglioma, intracranial carcinoma, ependymoma, brainstem tumor, head and neck tumor, larynx cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cell cancer, female urethral cancer or skin cancer. The degenerative brain disease can be Alzheimer's disease, Down syndrome, Parkinson's disease, Lou Gehrig's disease, dementia, Huntington's disease, multiple sclerosis, proximal lateral sclerosis, apoplexy, stroke or mild cognitive impairment. In addition, the metabolic disease herein can be diabetes, hypoglycemia, hypercholesterolemia, hyperlipidemia, hemochromatosis, amyloidosis or porphyria.

The compound represented by chemical formula 1 or the pharmaceutically acceptable salt thereof included in the pharmaceutical composition of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

The pharmaceutical composition comprising the compound represented by chemical formula 1 or the pharmaceutically acceptable salt thereof as an active ingredient can be administered by parenterally and the parenteral administration includes subcutaneous injection, intravenous injection, intramuscular injection, or intrathoracic injection.

To prepare the compound represented by chemical formula 1 or the pharmaceutically acceptable salt thereof as a formulation for parenteral administration, the compound represented by chemical formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the pharmaceutical composition comprising the compound represented by chemical formula 1 or the pharmaceutically acceptable salt thereof as an active ingredient can be determined according to age, weight, gender, administration method, health condition, and severity of disease. The dosage is generally 0.1~1000 mg/day, and preferably 1~500 mg/day based on an adult patient weighing 70 kg, which can be administered once or several times a day at intervals of a certain time depending on the judgment of a doctor or a pharmacist.

The pharmaceutical composition comprising the compound represented by chemical formula 1 or the pharmaceutically acceptable salt thereof as an active ingredient can be administered alone or together with surgical operation, hormone therapy, chemo-therapy and biological regulators to prevent and treat DYRK1A related disease.

The compound represented by chemical formula 1 of the present invention, the optical isomer thereof or the pharmaceutically acceptable salt thereof was confirmed to have excellent activity to inhibit DYRK1A kinase in Experimental Examples 1 and 2. In addition, the compound represented by chemical formula 1 of the present invention, the optical isomer thereof or the pharmaceutically acceptable salt thereof was confirmed to have excellent activity to inhibit DYRK1A phosphorylation at the cellular level in Experimental Example 3. It was also confirmed in Experimental Example 4 that the compound represented by chemical formula 1 of the present invention, the optical isomer thereof or the pharmaceutically acceptable salt thereof was excellent in inhibiting phosphorylation of Tau, an important factor of Down syndrome. Further, it was also confirmed in Experimental Example 5 that the compound represented by chemical formula 1 of the present invention, the optical isomer thereof or the pharmaceutically acceptable salt thereof had DYRK1A kinase activity inhibiting effect in vivo.

The compound represented by chemical formula 1 of the present invention, the optical isomer thereof or the pharmaceutically acceptable salt thereof was confirmed to have excellent activity to inhibit Tau phosphorylation in the Alzheimer's disease animal model in Experimental Example 7. It was also confirmed in Experimental Example 8 that the compound represented by chemical formula 1 of the present invention, the optical isomer thereof or the pharmaceutically acceptable salt thereof was excellent in inhibiting DYRK1A protein activity. In Experimental Example 9, the compound represented by chemical formula 1 of the present invention, the optical isomer thereof or the pharmaceutically acceptable salt thereof was confirmed to reduce amyloid plaque, one of causes of Alzheimer's disease. In Experimental Example 10, the compound represented by chemical formula 1 of the present invention, the optical isomer thereof or the pharmaceutically acceptable salt thereof was confirmed to improve the short term cognitive decline caused by Alzheimer's disease, and also confirmed to improve the long term cognitive decline caused by Alzheimer's disease in Experimental Example 11.

Therefore, a pharmaceutical composition and a health functional food composition comprising the compound represented by chemical formula 1 of the present invention, the optical isomer thereof or the pharmaceutically acceptable salt thereof can be effectively used for the treatment or prevention of DYRK1A related disease. In particular, they can be effectively used for the prevention, treatment or amelioration of Alzheimer's disease, dementia or Alzheimer's dementia.

The present invention also provides a health functional food composition comprising a compound represented by chemical formula 1, an optical isomer thereof or a pharmaceutically acceptable salt thereof as an active ingredient for preventing or ameliorating a disease selected from the group consisting of cancer, degenerative brain disease and metabolic disease.

The compound represented by chemical formula 1 above can inhibit the protein kinase activity.

At this time, the protein kinase can be ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK or YSK4.

The degenerative brain disease herein can be Alzheimer's disease, Down syndrome, Parkinson's disease, Lou Gehrig's disease, dementia, Huntington's disease, multiple sclerosis, proximal lateral sclerosis, apoplexy, stroke or mild cognitive impairment.

The said dementia can be Alzheimer's dementia, cerebrovascular dementia, dementia caused by head injury, multi-infarct dementia, Alzheimer's/multi-infarction dementia or alcoholic dementia.

The metabolic disease herein can be diabetes, hypoglycemia, hypercholesterolemia, hyperlipidemia, hemochromatosis, amyloidosis or porphyria.

The cancer can be brain cancer, brain tumor, benign astrocytoma, malignant astrocytoma, pituitary adenoma, meningioma, brain lymphoma, oligodendroglioma, intracranial carcinoma, ependymoma, brainstem tumor, head and neck tumor, larynx cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cell cancer, female urethral cancer or skin cancer. The degenerative brain disease can be Alzheimer's disease, Down syndrome, Parkinson's disease, Lou Gehrig's disease, dementia, Huntington's disease, multiple sclerosis, proximal lateral sclerosis, apoplexy, stroke or mild cognitive impairment. In addition, the metabolic disease herein can be diabetes, hypoglycemia, hypercholesterolemia, hyperlipidemia, hemochromatosis, amyloidosis or porphyria.

The compound represented by chemical formula 1 of the present invention can be used as a food additive. In that case, the compound represented by chemical formula 1 of the present invention can be added as it is or as mixed with other food components according to the conventional method. The mixing ratio of active ingredients can be regulated according to the purpose of use (prevention or amelioration). In general, the compound of the present invention is preferably added to food or beverages by 0.1~90 weight part for the total weight of the food or beverages. However, if long term administration is required for health and hygiene or regulating health condition, the content can be lower than the above but higher content can be accepted as well since the compound of the present invention has been proved to be very safe.

The health beverage composition of the present invention can additionally include various flavors or natural carbohydrates, etc, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the invention.

In addition to the ingredients mentioned above, the compound represented by chemical formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by chemical formula 1 of the present invention can also include natural fruit juice, fruit beverages and fruit flesh addable to vegetable beverages.

The present invention also provides a method for preventing or treating a disease selected from the group consisting of cancer, degenerative brain disease and metabolic disease, which comprises the step of administering a pharmaceutical composition or a health functional food composition comprising a compound represented by chemical formula 1 or a pharmaceutically acceptable salt thereof as an active ingredient to a subject in need.

In addition, the present invention provides a use of the pharmaceutical composition or the health functional food composition above comprising a compound represented by chemical formula 1 or a pharmaceutically acceptable salt thereof as an active ingredient for preventing or treating a disease selected from the group consisting of cancer, degenerative brain disease and metabolic disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Preparative Example 1-1> Preparation of 6-chloro-4-(methylamino)-1-((2-(trimethylsilyl) ethoxy)methyl)-1H-pyrrolo[2,3-b]pyridine-3-carbonitrile 6-Chloro-4-(methylamino)-1-((2-(trimethylsilyl)ethoxy)methyl)-1H-pyrrolo[2,3-b]pyridine-3-carbonitrile was prepared by the method shown in reaction formula 2 below.

[Reaction Formula 2]

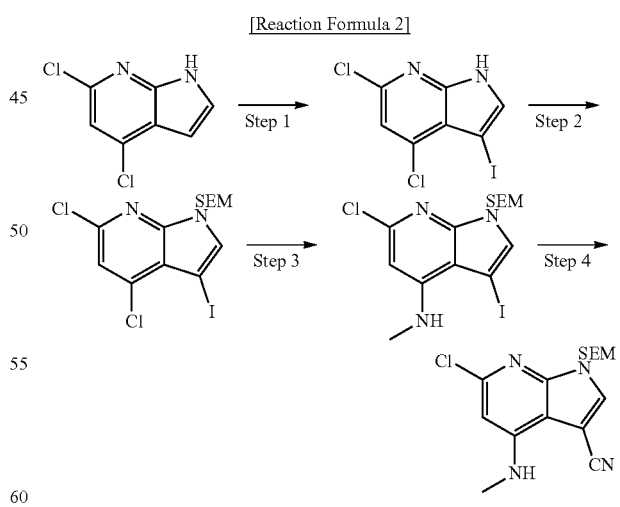

Step 1: 4,6-Dichloro-1H-pyrrolo[2,3-b]pyridine (1.0 e.q.) was dissolved in DMF, followed by lowering the temperature to −10° C. N-iodosuccinimide (1.1 e.g.) was added to the mixture, followed by raising the temperature to room temperature. The mixture was stirred for 1 hour. Upon completion of the reaction, iced water was added thereto to induce precipitation. The formed precipitate was filtered and as a result a white target compound was obtained (yield: 100%).

Step 2: 4,6-Dichloro-3-iodo-1H-pyrrolo[2,3-b]pyridine (1.0 e.q.) was dissolved in DMF (0.5 M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over MgSO$_4$. The mixture was purified by MPCL (EtOAc:Hex) and as a result a white solid target compound was obtained (yield: 100%).

Step 3: 4,6-Dichloro-3-iodo-1-((2-(trimethylsilyl)ethoxy)methyl)-1H-pyrrolo[2,3-b]pyridine (1.0 e.q.) was dissolved in EtOH, to which methylamine (5.0 e.q., 35 wt % in ethanol) was added at room temperature, followed by stirring at 100° C. for 14 hours. Upon completion of the reaction, water was added thereto to induce precipitation. The formed precipitate was filtered and as a result a target compound was obtained (yield: 86%).

Step 4: 6-Chloro-3-iodo-N-methyl-1-((2-(trimethylsilyl)ethoxy)methyl)-1H-pyrrolo[2,3-b]pyridine-4-amine (1.0 e.q.) was dissolved in DMF (0.2 M), to which Pd(PPh$_3$)$_4$ (0.15 e.q.) and Zn(CN)$_2$ (2.0 e.q.) were added stepwise under nitrogen atmosphere, followed by raising the temperature to 80° C. After reacting for 14 hours, the reaction mixture was cooled to room temperature and diluted with EtOAc. The organic layer was washed with sat. NaHCO$_3$ and brine stepwise and the remaining water was dried over MgSO$_4$. The mixture was purified by MPCL (EtOAc:Hex) and as a result a yellow solid target compound (6-chloro-4-(methylamino)-1-((2-(trimethylsilyl)ethoxy)methyl)-1H-pyrrolo[2,3-b]pyridine-3-carbonitrile) was obtained (yield: 57%).

<Preparative Example 1-2> Preparation of 6-chloro-4-(ethylamino)-1-((2-(trimethylsilyl)ethoxy)methyl)-1H-pyrrolo[2,3-b]pyridine-3-carbonitrile 6-Chloro-4-(ethylamino)-1-((2-(trimethylsilyl)ethoxy)methyl)-1H-pyrrolo[2,3-b]pyridine-3-carbonitrile was prepared by the similar manner to the method described in <Preparative Example 1-1> (yield: 56%).

<Preparative Example 1-3> Preparation of 6-chloro-4-(propylamino)-1-((2-(trimethylsilyl)ethoxy)methyl)-1H-pyrrolo[2,3-b]pyridine-3-carbonitrile 6-Chloro-4-(propylamino)-1-((2-(trimethylsilyl)ethoxy)methyl)-1H-pyrrolo[2,3-b]pyridine-3-carbonitrile was prepared by the similar manner to the method described in <Preparative Example 1-1> (yield: 67%).

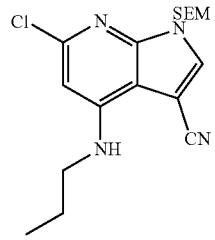 [SMILES: CCCNc1cc(Cl)nc2c1c(C#N)cn2COCC[Si](C)(C)C]

<Preparative Example 1-4> Preparation of 6-chloro-4-(2-methoxyethylamino)-1-((2-(trimethylsilyl)ethoxy)methyl)-1H-pyrrolo[2,3-b]pyridine-3-carbonitrile 6-Chloro-4-(2-methoxyethylamino)-1-((2-(trimethylsilyl)ethoxy)methyl)-1H-pyrrolo[2,3-b]pyridine-3-carbonitrile was prepared by the similar manner to the method described in <Preparative Example 1-1> (yield: 67%).

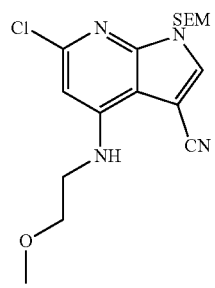 [SMILES: COCCNc1cc(Cl)nc2c1c(C#N)cn2COCC[Si](C)(C)C]

<Preparative Example 1-5> Preparation of 6-chloro-4-((2-methoxyethyl)(methyl)amino)-1-((2-(trimethylsilyl)ethoxy)methyl)-1H-pyrrolo[2,3-b]pyridine-3-carbonitrile 6-Chloro-4-((2-methoxyethyl)(methyl)amino)-1-((2-(trimethylsilyl)ethoxy)methyl)-1H-pyrrolo[2,3-b]pyridine-3-carbonitrile was prepared by the similar manner to the method described in <Preparative Example 1-1> (yield: 67%).

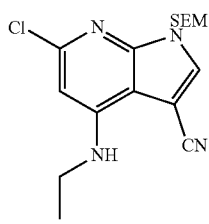

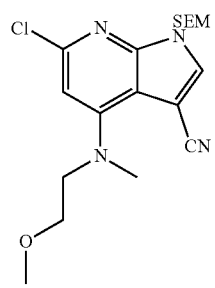 [SMILES: COCCN(C)c1cc(Cl)nc2c1c(C#N)cn2COCC[Si](C)(C)C]

<Preparative Example 2-1> Preparation of 6-chloro-4-methoxy-1-((2-(trimethylsilyl)ethoxy)methyl)-1H-pyrrolo[2,3-b]pyridine-3-carbonitrile 6-Chloro-4-methoxy-1-((2-(trimethylsilyl)ethoxy)methyl)-1H-pyrrolo[2,3-b]pyridine-3-carbonitrile was prepared by the method shown in reaction formula 3 below.

[Reaction Formula 3]

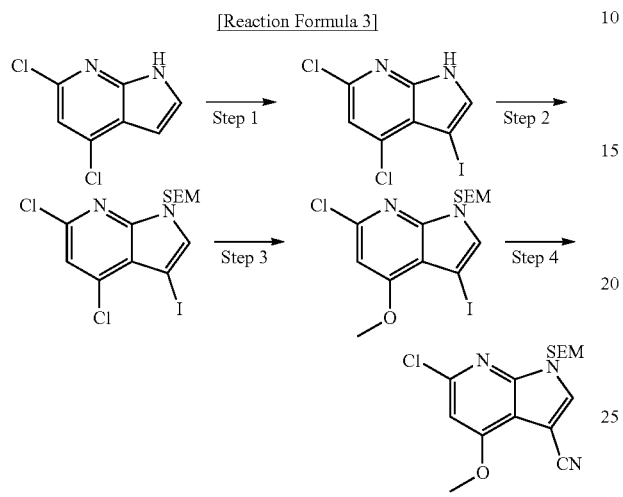

Step 1: 4,6-Dichloro-1H-pyrrolo[2,3-b]pyridine (1.0 e.q.) was dissolved in DMF, followed by lowering the temperature to −10° C. N-iodosuccinimide (1.1 e.q.) was added to the mixture, followed by raising the temperature to room temperature. The mixture was stirred for 1 hour. Upon completion of the reaction, iced water was added thereto to induce precipitation. The formed precipitate was filtered and as a result a white target compound was obtained (yield: 100%).

Step 2: 4,6-Dichloro-3-iodo-1H-pyrrolo[2,3-b]pyridine (1.0 e.q.) was dissolved in DMF (0.5 M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over MgSO$_4$. The mixture was purified by MPCL (EtOAc:Hex) and as a result a white solid target compound was obtained (yield: 100%).

Step 3: 4,6-Dichloro-1H-pyrrolo[2,3-b]pyridine (1.0 e.q.) was dissolved in methanol (0.1 M), to which Na fragments were added at room temperature. The temperature of the mixture was raised to 90° C., and then refluxed for 14 hours. Upon completion of the reaction, the temperature of the reaction mixture was lowered to room temperature and water was added thereto to induce precipitation. The formed precipitate was filtered and as a result a white target compound was obtained (yield: 80%).

Step 4: 6-Chloro-3-iodo-4-methoxy-1-((2-(trimethylsilyl)ethoxy)methyl)-1H-pyrrolo[2,3-b]pyridine (1.0 e.g.) was dissolved in DMF (0.2 M) at room temperature, to which Pd(PPh$_3$)$_4$ (0.15 e.q.) and Zn(CN)$_2$ (2.0 e.q.) were added stepwise under nitrogen atmosphere, followed by raising the temperature to 80° C. After reacting for 14 hours, the reaction mixture was cooled to room temperature and diluted with EtOAc. The organic layer was washed with sat. NaHCO$_3$ and brine stepwise and the remaining water was dried over MgSO$_4$. The mixture was purified by MPCL (EtOAc:Hex) and as a result a yellow solid target compound (6-chloro-4-(methylamino)-1-((2-(trimethylsilyl)ethoxy)methyl)-1H-pyrrolo[2,3-b]pyridine-3-carbonitrile) was obtained (yield: 57%).

<Preparative Example 2-2> Preparation of 6-chloro-4-ethoxy-1-((2-(trimethylsilyl)ethoxy)methyl)-1H-pyrrolo[2,3-b]pyridine-3-carbonitrile 6-Chloro-4-ethoxy-1-((2-(trimethylsilyl)ethoxy)methyl)-1H-pyrrolo[2,3-b]pyridine-3-carbonitrile was prepared by the similar manner to the method described in <Preparative Example 2-1> (yield: 67%).

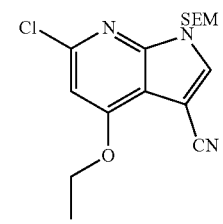 [SMILES: CCOc1cc(Cl)nc2c1c(C#N)cn2COCC[Si](C)(C)C]

<Preparative Example 2-3> Preparation of 6-chloro-4-(1-methylcyclopropoxy)-1-((2-(trimethylsilyl)ethoxy)methyl)-1H-pyrrolo[2,3-b]pyridine-3-carbonitrile 6-Chloro-4-(1-methylcyclopropoxy)-1-((2-(trimethylsilyl)ethoxy)methyl)-1H-pyrrolo[2,3-b]pyridine-3-carbonitrile was prepared by the similar manner to the method described in <Preparative Example 2-1> (yield: 67%).

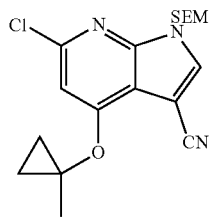 [SMILES: CC1(Oc2cc(Cl)nc3c2c(C#N)cn3COCC[Si](C)(C)C)CC1]

<Preparative Example 3-1> Preparation of 6-chloro-N-methyl-3-(trifluoromethyl)-1-((2-(trimethylsilyl)ethoxy)methyl)-1H-pyrrolo[2,3-b]pyridine-4-amine 6-Chloro-4-methoxy-1-((2-(trimethylsilyl)ethoxy)methyl)-1H-pyrrolo[2,3-b]pyridine-3-carbonitrile was prepared by the method shown in reaction formula 4 below.

[Reaction Formula 4]

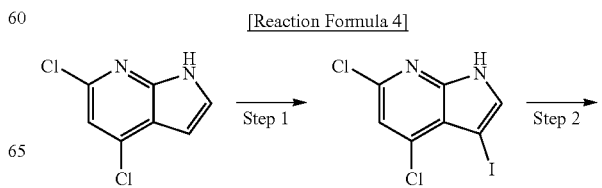

-continued

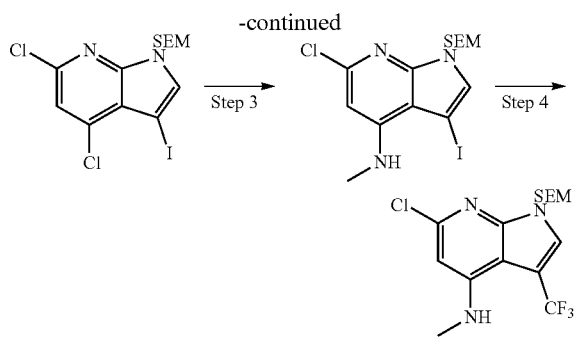

Step 1: 4,6-Dichloro-1H-pyrrolo[2,3-b]pyridine (1.0 e.q.) was dissolved in DMF, followed by lowering the temperature to −10° C. N-iodosuccinimide (1.1 e.q.) was added to the mixture, followed by raising the temperature to room temperature. The mixture was stirred for 1 hour. Upon completion of the reaction, iced water was added thereto to induce precipitation. The formed precipitate was filtered and as a result a white target compound was obtained (yield: 100%).

Step 2: 4,6-Dichloro-3-iodo-1H-pyrrolo[2,3-b]pyridine (1.0 e.q.) was dissolved in DMF (0.5 M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over MgSO$_4$. The mixture was purified by MPCL (EtOAc:Hex) and as a result a white solid target compound was obtained (yield: 100%).

Step 3: 4,6-Dichloro-3-iodo-1-((2-(trimethylsilyl)ethoxy)methyl)-1H-pyrrolo[2,3-b]pyridine (1.0 e.q.) was dissolved in EtOH, to which methyl amine (5.0 e.q., 35 wt % in ethanol) was added at room temperature. The mixture was stirred at 100° C. for hours. Upon completion of the reaction, water was added thereto to induce precipitation. The formed precipitate was filtered and as a result a target compound was obtained (yield: 86%).

Step 4: A two-necked round-bottom flask was filled with nitrogen gas, to which CuI (5.0 e.q.) and KF (5.0 e.q.) were added. The temperature of the mixture was raised to 150° C., followed by stirring under reduced pressure for 2 hours. Upon completion of the reaction, the temperature was lowered to room temperature. Trimethyl(trifluoromethyl)silane (5.0 e.q.) dissolved in DMF/NMP (1:1) was added thereto using a syringe in the presence of nitrogen. After reacting for 30 minutes, 6-chloro-3-iodo-N-methyl-1-((2-(trimethylsilyl)ethoxy)methyl)-1H-pyrrolo[2,3-b]pyridine-4-amine (1.0 e.q.) dissolved in DMF/NMP (1:1) was added thereto using a syringe, followed by reaction at 45° C. for 48 hours. Upon completion of the reaction, water was added to the reactant to induce precipitation, and the formed precipitate was removed by filtration. Organic materials were extracted from the collected filtrate with EtOAc (×3). The collected organic layer was washed with brine and the remaining water was dried over Na$_2$SO$_4$. The mixture was purified by MPCL (EtOAc:Hex) and as a result a white solid target compound was obtained (yield: 58%).

<Preparative Example 3-2> Preparation of 6-chloro-N-ethyl-3-(trifluoromethyl)-1-((2-(trimethylsilyl)ethoxy)methyl)-1H-pyrrolo[2,3-b]pyridine-4-amine 6-Chloro-N-ethyl-3-(trifluoromethyl)-1-((2-(trimethylsilyl)ethoxy)methyl)-1H-pyrrolo[2,3-b]pyridine-4-amine was prepared by the similar manner to the method described in <Preparative Example 3-1> (yield: 67%).

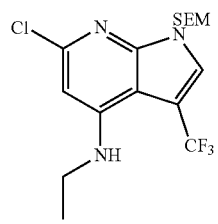 [SMILES: CCNc1cc(Cl)nc2c1c(C(F)(F)F)cn2COCC[Si](C)(C)C]

<Preparative Example 3-3> Preparation of 6-chloro-N-(2-methoxyethyl)-3-(trifluoromethyl)-1-((2-(trimethylsilyl)ethoxy)methyl)-1H-pyrrolo[2,3-b]pyridine-4-amine 6-Chloro-N-(2-methoxyethyl)-3-(trifluoromethyl)-1-((2-(trimethylsilyl)ethoxy)methyl)-1H-pyrrolo[2,3-b]pyridine-4-amine was prepared by the similar manner to the method described in <Preparative Example 3-1>.

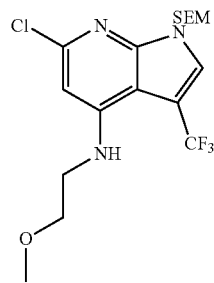 [SMILES: COCCNc1cc(Cl)nc2c1c(C(F)(F)F)cn2COCC[Si](C)(C)C]

<Example 1> Preparation 1 of the Compound According to the Present Invention

The pyrrolo-pyridine derivative compound according to the present invention was prepared by the method shown in reaction formula 5 below.

[Reaction Formula 5]

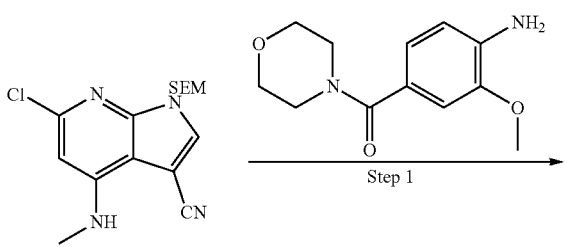

-continued

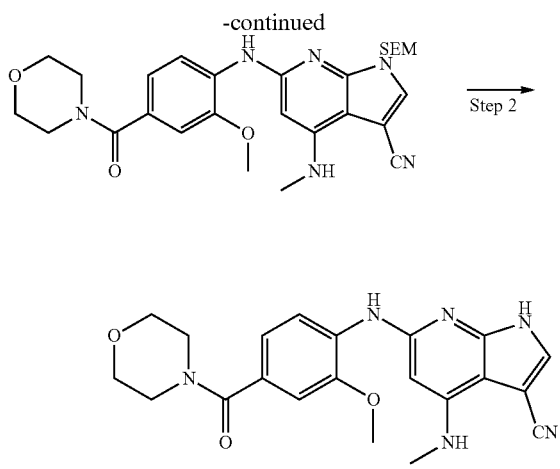

Step 1: The 6-chloro-4-(methylamino)-1-((2-(trimethylsilyl)ethoxy)methyl)-1H-pyrrolo[2,3-b]pyridine-3-carbonitrile (1.0 e.q.) prepared in <Preparative Example 1-1>, (4-amino-3-methoxyphenyl) (morpholino)methanone (1.0 e.q.) and $K_2CO_3$ (5.0 e.q.) were dissolved in sec-BuOH (0.1 M), followed by ultrasonication for 1 minute to eliminate gas. $Pd_2(dba)_3$ (0.1 e.q.) and Xphos (0.1 e.q.) were added to the reaction mixture at 100° C., followed by reaction for 2 hours. Upon completion of the reaction, the reaction mixture was filtered with celite and then washed with EtOAc and MeOH. The obtained filtrate was concentrated and as a result a yellow solid target compound (6-(2-methoxy-4-(morpholine-4-carbonyl)phenylamino)-4-(methylamino)-1-((2-(trimethylsilyl)ethoxy)methyl)-1H-pyrrolo[2,3-b]pyridine-3-carbonitrile) was obtained.

Step 2: The 6-(2-methoxy-4-(morpholine-4-carbonyl)phenylamino)-4-(methylamino)-1-((2-(trimethylsilyl)ethoxy)methyl)-1H-pyrrolo[2,3-b]pyridine-3-carbonitrile (1.0 e.q.) prepared in step 1 above was dissolved in $CH_2Cl_2$ (0.05 M), to which TFA (100 e.q.) was added at room temperature. After reacting 4 hours, the solvent was eliminated. The concentrated reaction mixture was dissolved in THF (0.03 M) again, to which sat. $Na_2CO_3$ (0.03 M) was added at room temperature, followed by reaction for 14 hours. Upon completion of the reaction, the resulting product was diluted in EtOAc, and then washed with water and brine stepwise. The organic layer was dried over $MgSO_4$. The mixture was purified by prep-HPLC and as a result a yellow solid target compound (6-(2-methoxy-4-(morpholine-4-carbonyl)phenylamino)-4-(methylamino)-1H-pyrrolo[2,3-b]pyridine-3-carbonitrile) was obtained (yield: 67%).

<Example 2>~<Example 105> Preparation 2 of the Compound According to the Present Invention The pyrrolo-pyridine derivatives of the present invention were prepared by the similar manner to the method described in Example 1 using the compounds of <Preparative Example 1-1>~<Preparative Example 1-5>, <Preparative Example 2-1>~<Preparative Example 2-3> and <Preparative Example 3-1>~<Preparative Example 3-3>. Chemical structural formulas of the compounds of Examples 1~105 are shown in Tables 1~3 below. Compound names, $H^1$ NMR data, yields and HPLC results are summarized in Table 4 below.

TABLE 1

| Example | Chemical Structure |
|---|---|
| 1 | 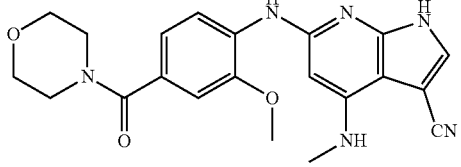 |
| 2 | 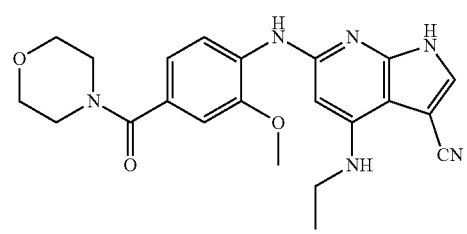 [SMILES: CCNc1cc(Nc2ccc(C(=O)N3CCOCC3)cc2OC)nc2[nH]cc(C#N)c12] |
| 3 | 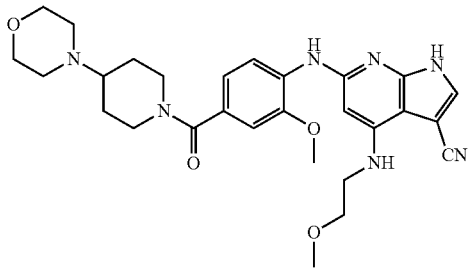 [SMILES: COCCNc1cc(Nc2ccc(C(=O)N3CCC(N4CCOCC4)CC3)cc2OC)nc2[nH]cc(C#N)c12] |
| 4 | 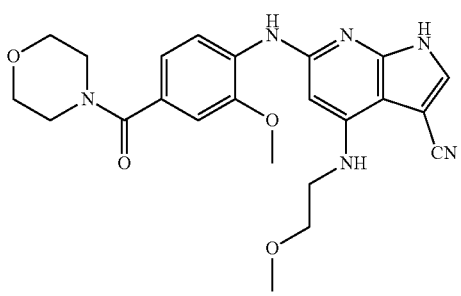 [SMILES: COCCNc1cc(Nc2ccc(C(=O)N3CCOCC3)cc2OC)nc2[nH]cc(C#N)c12] |
| 5 | 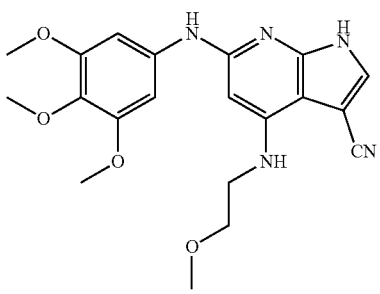 [SMILES: COCCNc1cc(Nc2cc(OC)c(OC)c(OC)c2)nc2[nH]cc(C#N)c12] |
| 6 | 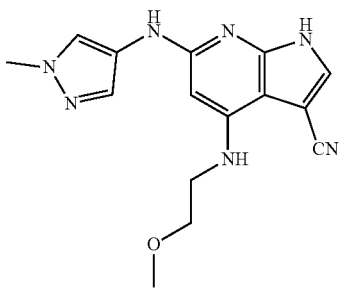 [SMILES: COCCNc1cc(Nc2cnn(C)c2)nc2[nH]cc(C#N)c12] |

TABLE 1-continued
| Example | Chemical Structure |
|---|---|
| 7 | 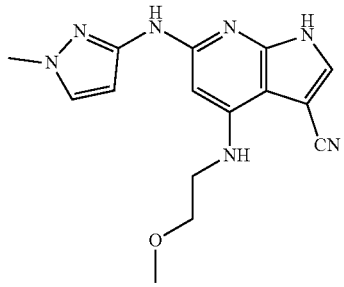 [SMILES: COCCNc1cc(Nc2ccn(C)n2)nc2[nH]cc(C#N)c12] |
| 8 | 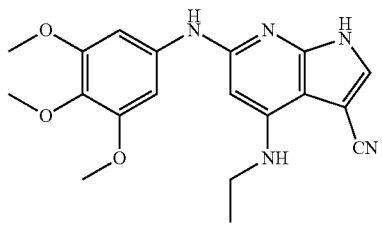 [SMILES: CCNc1cc(Nc2cc(OC)c(OC)c(OC)c2)nc2[nH]cc(C#N)c12] |
| 9 | 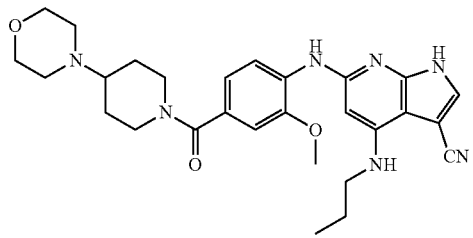 [SMILES: CCCNc1cc(Nc2ccc(C(=O)N3CCC(N4CCOCC4)CC3)cc2OC)nc2[nH]cc(C#N)c12] |
| 10 | 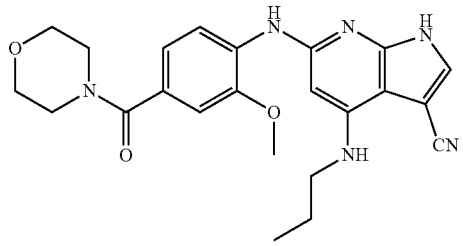 [SMILES: CCCNc1cc(Nc2ccc(C(=O)N3CCOCC3)cc2OC)nc2[nH]cc(C#N)c12] |
| 11 | 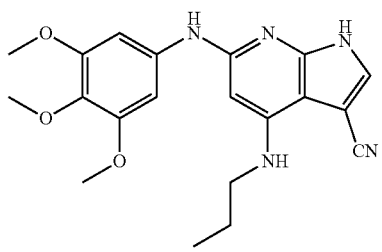 [SMILES: CCCNc1cc(Nc2cc(OC)c(OC)c(OC)c2)nc2[nH]cc(C#N)c12] |
| 12 | 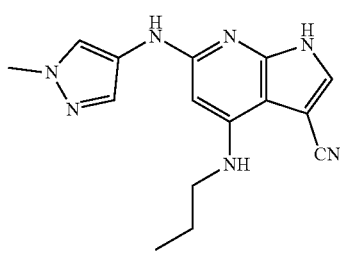 [SMILES: CCCNc1cc(Nc2cnn(C)c2)nc2[nH]cc(C#N)c12] |
TABLE 1-continued
| Example | Chemical Structure |
|---|---|
| 13 | 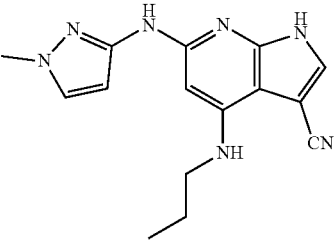 [SMILES: CCCNc1cc(Nc2ccn(C)n2)nc2[nH]cc(C#N)c12] |
| 14 | 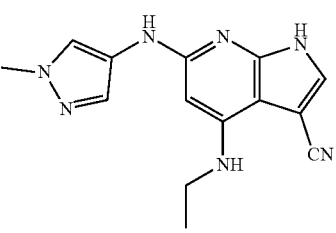 [SMILES: CCNc1cc(Nc2cnn(C)c2)nc2[nH]cc(C#N)c12] |
| 15 | 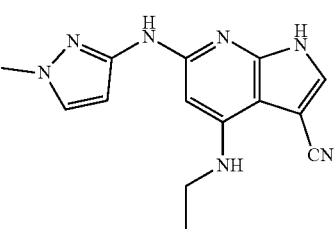 [SMILES: CCNc1cc(Nc2ccn(C)n2)nc2[nH]cc(C#N)c12] |
| 16 | 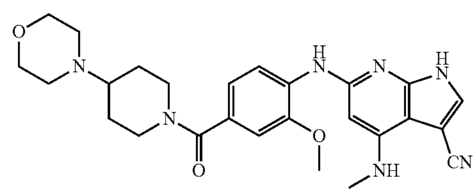 [SMILES: CNc1cc(Nc2ccc(C(=O)N3CCC(N4CCOCC4)CC3)cc2OC)nc2[nH]cc(C#N)c12] |
| 17 | 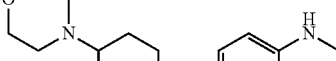 |
| 18 | 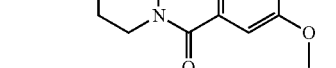 |
| 19 | 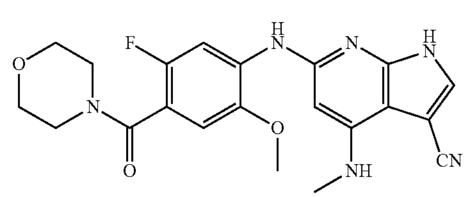 [SMILES: CNc1cc(Nc2cc(F)c(C(=O)N3CCOCC3)cc2OC)nc2[nH]cc(C#N)c12] |

TABLE 1-continued
| Example | Chemical Structure |
|---|---|
| 20 | 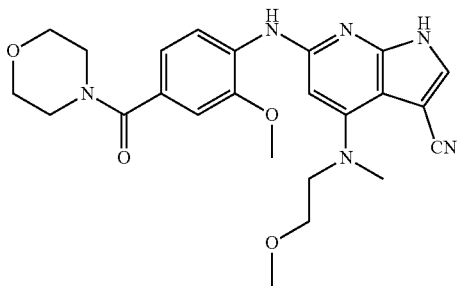 [SMILES: COCCN(C)c1cc(Nc2ccc(C(=O)N3CCOCC3)cc2OC)nc2[nH]cc(C#N)c12] |
| 21 | 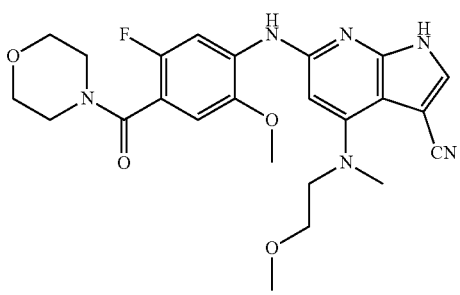 [SMILES: COCCN(C)c1cc(Nc2cc(F)c(C(=O)N3CCOCC3)cc2OC)nc2[nH]cc(C#N)c12] |
| 22 | 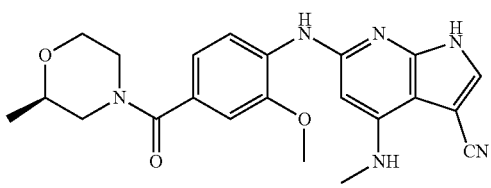 [SMILES: CNc1cc(Nc2ccc(C(=O)N3CCO[C@H](C)C3)cc2OC)nc2[nH]cc(C#N)c12] |
| 23 | 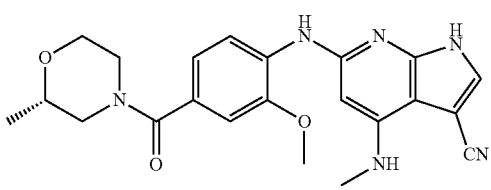 [SMILES: CNc1cc(Nc2ccc(C(=O)N3CCO[C@@H](C)C3)cc2OC)nc2[nH]cc(C#N)c12] |
| 24 | 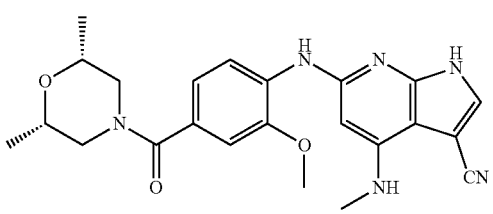 [SMILES: CNc1cc(Nc2ccc(C(=O)N3C[C@@H](C)O[C@@H](C)C3)cc2OC)nc2[nH]cc(C#N)c12] |
| 25 | 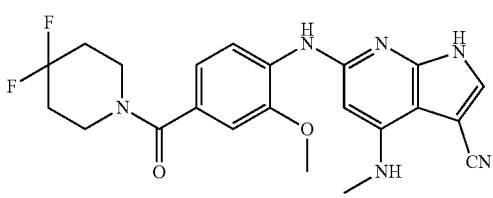 [SMILES: CNc1cc(Nc2ccc(C(=O)N3CCC(F)(F)CC3)cc2OC)nc2[nH]cc(C#N)c12] |
| 26 | 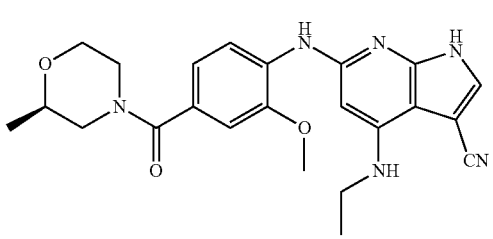 [SMILES: CCNc1cc(Nc2ccc(C(=O)N3CCO[C@H](C)C3)cc2OC)nc2[nH]cc(C#N)c12] |
| 27 | 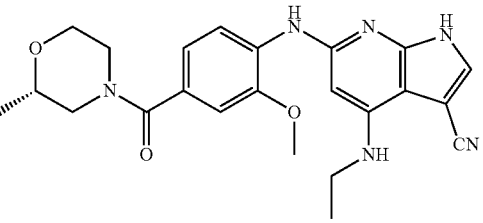 [SMILES: CCNc1cc(Nc2ccc(C(=O)N3CCO[C@@H](C)C3)cc2OC)nc2[nH]cc(C#N)c12] |
| 28 | 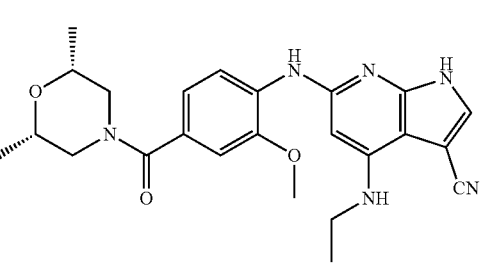 [SMILES: CCNc1cc(Nc2ccc(C(=O)N3C[C@@H](C)O[C@@H](C)C3)cc2OC)nc2[nH]cc(C#N)c12] |
| 29 | 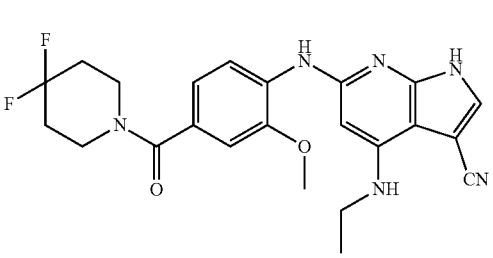 [SMILES: CCNc1cc(Nc2ccc(C(=O)N3CCC(F)(F)CC3)cc2OC)nc2[nH]cc(C#N)c12] |
| 30 | 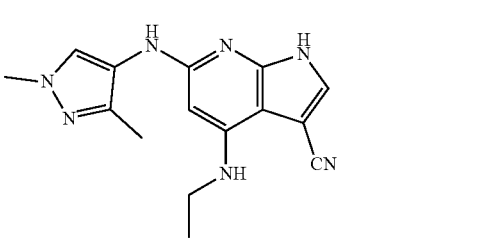 [SMILES: CCNc1cc(Nc2cn(C)nc2C)nc2[nH]cc(C#N)c12] |
| 31 | 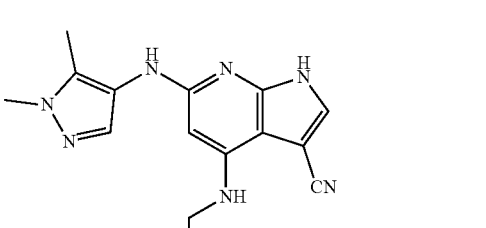 |
| 32 | 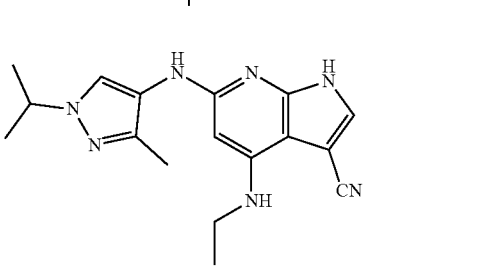 |

TABLE 1-continued
| Example | Chemical Structure |
|---|---|
| 33 | 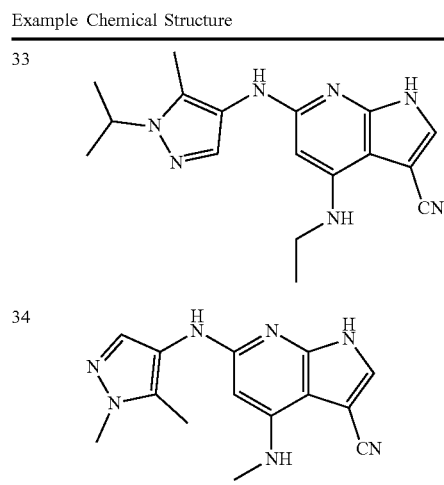 |
| 34 | 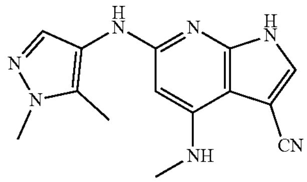 [SMILES: CNc1cc(Nc2cnn(C)c2C)nc2[nH]cc(C#N)c12] |
| 35 | 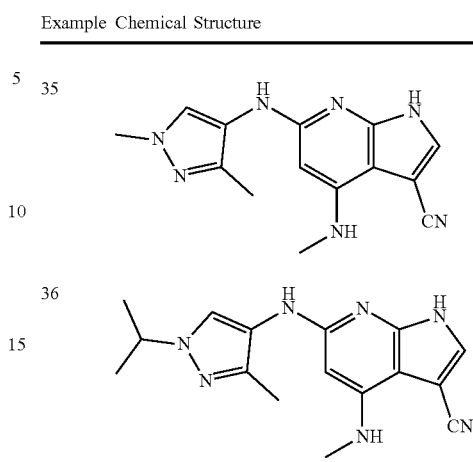 |
| 36 | |
TABLE 2
| Example | Chemical Structure |
|---|---|
| 37 | 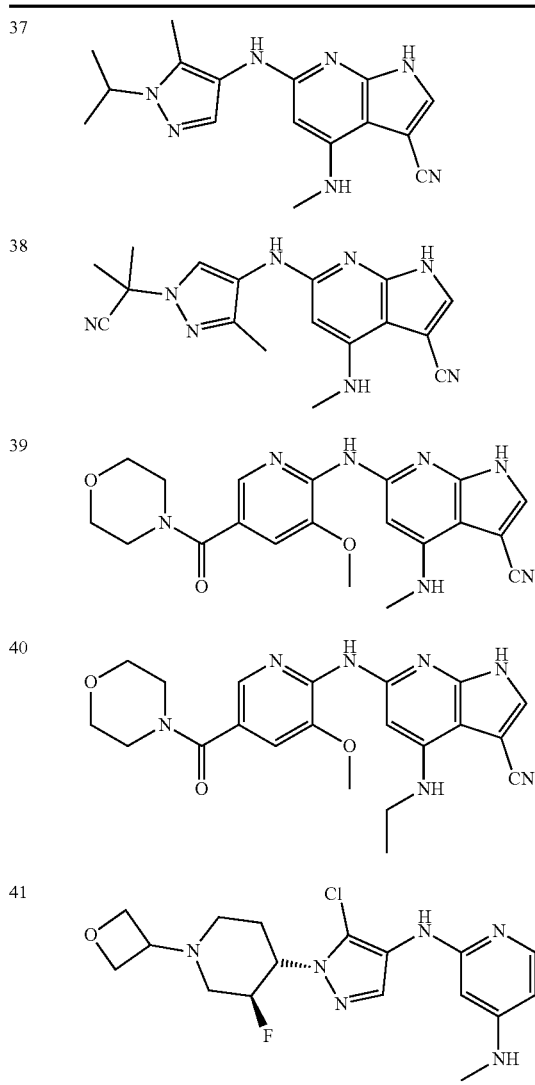 |
| 38 | 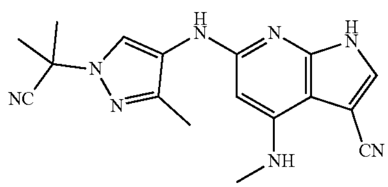 [SMILES: CNc1cc(Nc2cn(C(C)(C)C#N)nc2C)nc2[nH]cc(C#N)c12] |
| 39 | 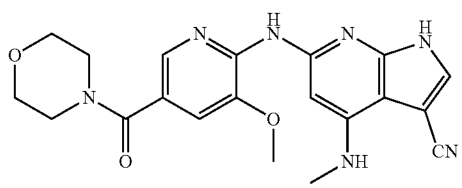 [SMILES: CNc1cc(Nc2ncc(C(=O)N3CCOCC3)cc2OC)nc2[nH]cc(C#N)c12] |
| 40 | 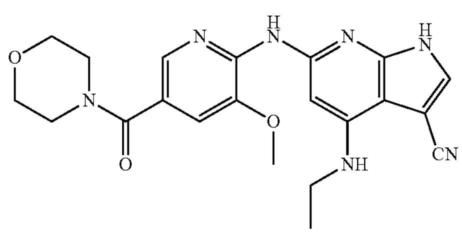 [SMILES: CCNc1cc(Nc2ncc(C(=O)N3CCOCC3)cc2OC)nc2[nH]cc(C#N)c12] |
| 41 | 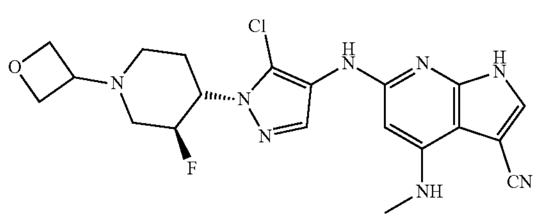 |

TABLE 2-continued
| Example | Chemical Structure |
|---|---|
| 42 | 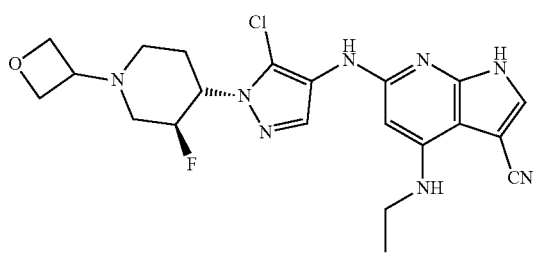 |
| 43 | 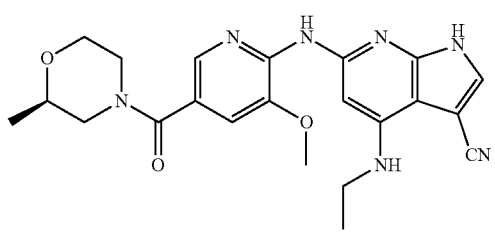 [SMILES: CCNc1cc(Nc2ncc(C(=O)N3CCO[C@H](C)C3)cc2OC)nc2[nH]cc(C#N)c12] |
| 44 | 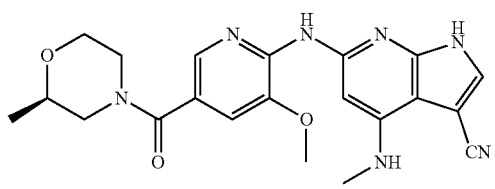 [SMILES: CNc1cc(Nc2ncc(C(=O)N3CCO[C@H](C)C3)cc2OC)nc2[nH]cc(C#N)c12] |
| 45 | 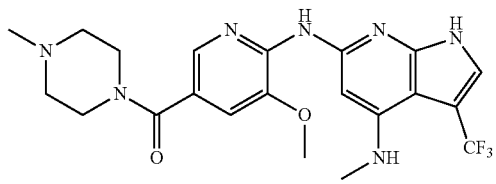 |
| 46 | 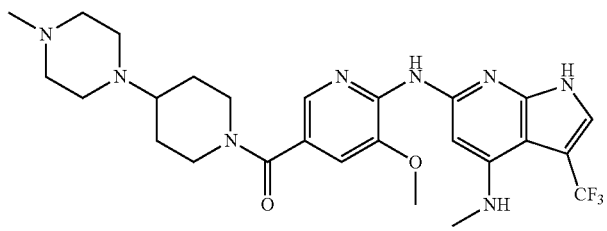 [SMILES: CNc1cc(Nc2ncc(C(=O)N3CCC(N4CCN(C)CC4)CC3)cc2OC)nc2[nH]cc(C(F)(F)F)c12] |
| 47 | 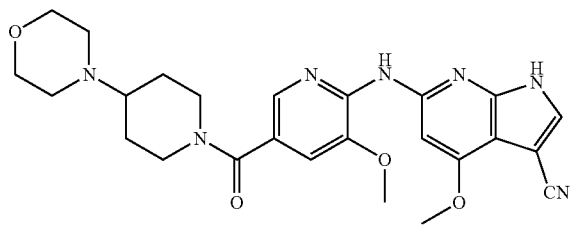 [SMILES: COc1cc(C(=O)N2CCC(N3CCOCC3)CC2)cnc1Nc1cc(OC)c2c(C#N)c[nH]c2n1] |
| 48 | 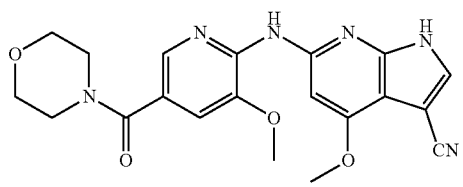 [SMILES: COc1cc(C(=O)N2CCOCC2)cnc1Nc1cc(OC)c2c(C#N)c[nH]c2n1] |

TABLE 2-continued
| Example | Chemical Structure |
|---|---|
| 49 | 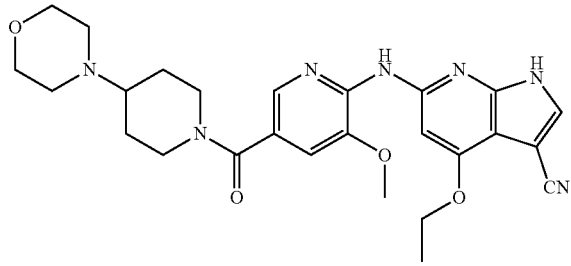 [SMILES: CCOc1cc(Nc2ncc(C(=O)N3CCC(N4CCOCC4)CC3)cc2OC)nc2[nH]cc(C#N)c12] |
| 50 | 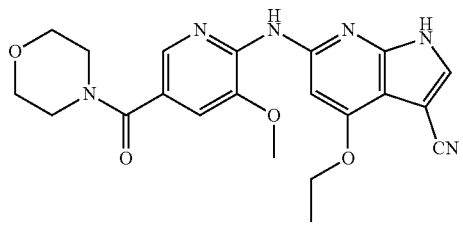 [SMILES: CCOc1cc(Nc2ncc(C(=O)N3CCOCC3)cc2OC)nc2[nH]cc(C#N)c12] |
| 51 | 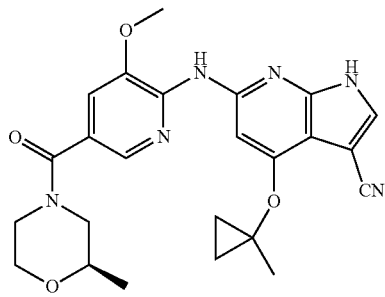 [SMILES: COc1cc(C(=O)N2CCO[C@H](C)C2)cnc1Nc1cc(OC2(C)CC2)c2c(C#N)c[nH]c2n1] |
| 52 | 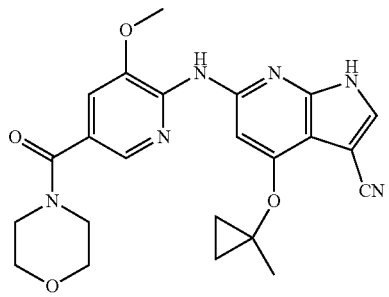 [SMILES: COc1cc(C(=O)N2CCOCC2)cnc1Nc1cc(OC2(C)CC2)c2c(C#N)c[nH]c2n1] |
| 53 | 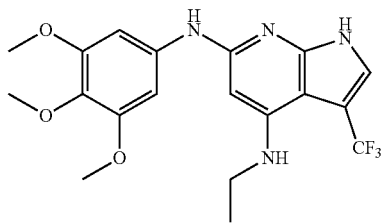 [SMILES: CCNc1cc(Nc2cc(OC)c(OC)c(OC)c2)nc2[nH]cc(C(F)(F)F)c12] |
| 54 | 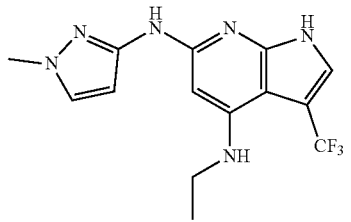 [SMILES: CCNc1cc(Nc2ccn(C)n2)nc2[nH]cc(C(F)(F)F)c12] |

TABLE 2-continued

| Example | Chemical Structure |
|---|---|
| 55 | 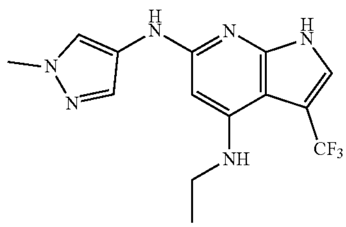 [SMILES: CCNc1cc(Nc2cnn(C)c2)nc2[nH]cc(C(F)(F)F)c12] |
| 56 | 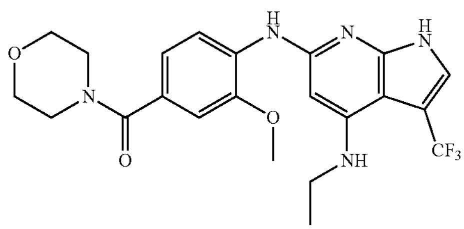 [SMILES: CCNc1cc(Nc2ccc(C(=O)N3CCOCC3)cc2OC)nc2[nH]cc(C(F)(F)F)c12] |
| 57 | 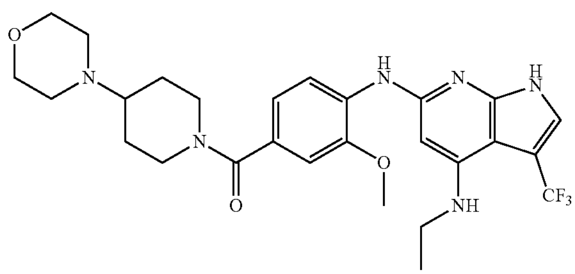 [SMILES: CCNc1cc(Nc2ccc(C(=O)N3CCC(N4CCOCC4)CC3)cc2OC)nc2[nH]cc(C(F)(F)F)c12] |
| 58 | 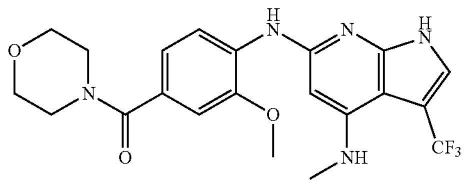 [SMILES: CNc1cc(Nc2ccc(C(=O)N3CCOCC3)cc2OC)nc2[nH]cc(C(F)(F)F)c12] |
| 59 | 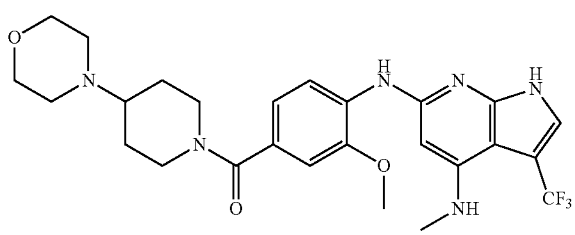 [SMILES: CNc1cc(Nc2ccc(C(=O)N3CCC(N4CCOCC4)CC3)cc2OC)nc2[nH]cc(C(F)(F)F)c12] |
| 60 | 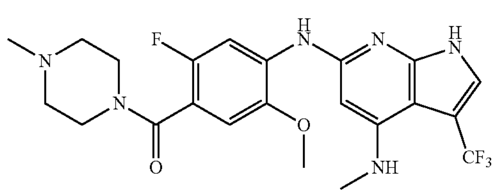 [SMILES: CNc1cc(Nc2cc(F)c(C(=O)N3CCN(C)CC3)cc2OC)nc2[nH]cc(C(F)(F)F)c12] |
| 61 | 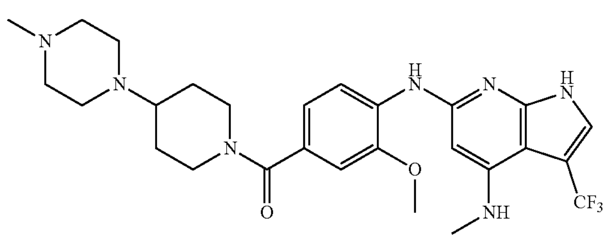 [SMILES: CNc1cc(Nc2ccc(C(=O)N3CCC(N4CCN(C)CC4)CC3)cc2OC)nc2[nH]cc(C(F)(F)F)c12] |

TABLE 2-continued
| Example | Chemical Structure |
|---|---|
| 62 | 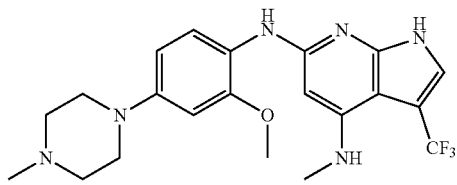 [SMILES: CNc1cc(Nc2ccc(N3CCN(C)CC3)cc2OC)nc2[nH]cc(C(F)(F)F)c12] |
| 63 | 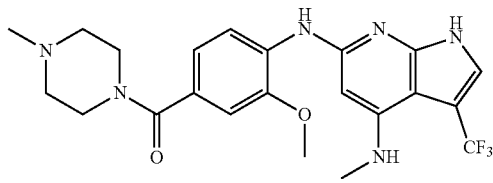 [SMILES: CNc1cc(Nc2ccc(C(=O)N3CCN(C)CC3)cc2OC)nc2[nH]cc(C(F)(F)F)c12] |
| 64 | 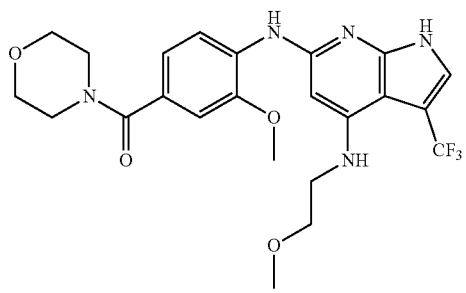 [SMILES: COCCNc1cc(Nc2ccc(C(=O)N3CCOCC3)cc2OC)nc2[nH]cc(C(F)(F)F)c12] |
| 65 | 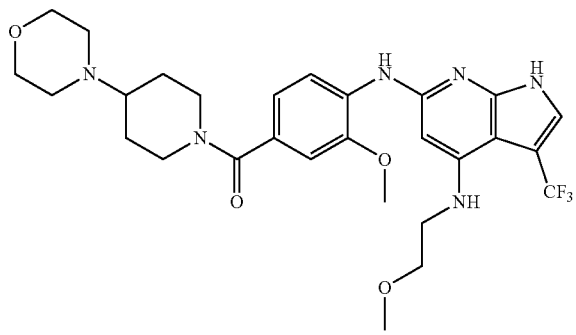 [SMILES: COCCNc1cc(Nc2ccc(C(=O)N3CCC(N4CCOCC4)CC3)cc2OC)nc2[nH]cc(C(F)(F)F)c12] |
| 66 | 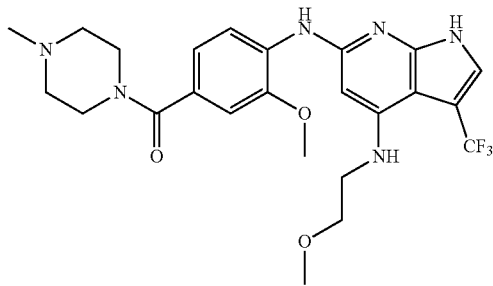 [SMILES: COCCNc1cc(Nc2ccc(C(=O)N3CCN(C)CC3)cc2OC)nc2[nH]cc(C(F)(F)F)c12] |

TABLE 2-continued
Example Chemical Structure
67 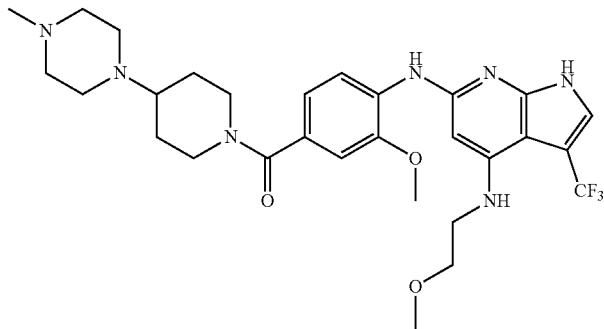 [SMILES: COCCNc1cc(Nc2ccc(C(=O)N3CCC(N4CCN(C)CC4)CC3)cc2OC)nc2[nH]cc(C(F)(F)F)c12]
68 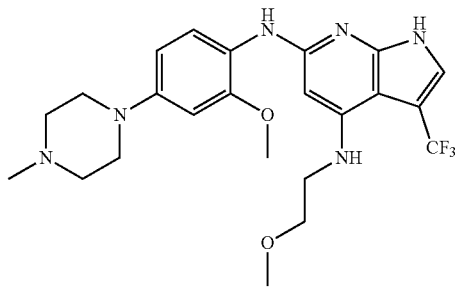 [SMILES: COCCNc1cc(Nc2ccc(N3CCN(C)CC3)cc2OC)nc2[nH]cc(C(F)(F)F)c12]
69 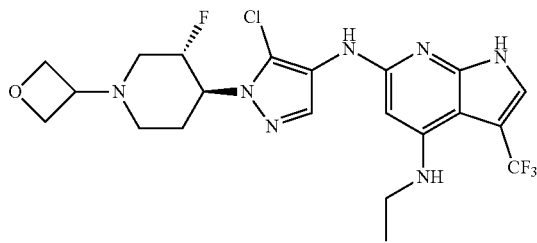 [SMILES: CCNc1cc(Nc2cnn([C@H]3CCN(C4COC4)C[C@@H]3F)c2Cl)nc2[nH]cc(C(F)(F)F)c12]
70 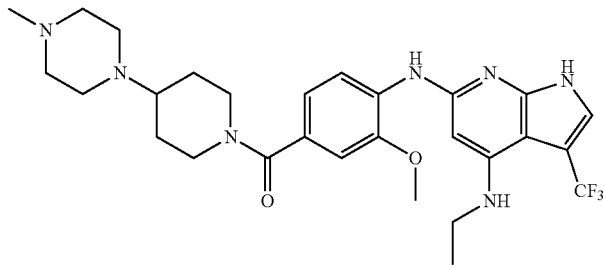 [SMILES: CCNc1cc(Nc2ccc(C(=O)N3CCC(N4CCN(C)CC4)CC3)cc2OC)nc2[nH]cc(C(F)(F)F)c12]
71 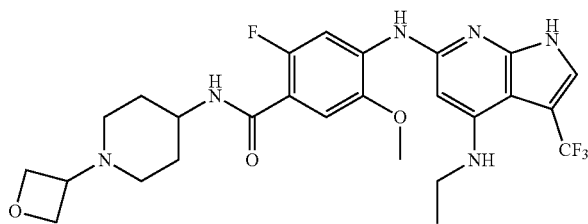 [SMILES: CCNc1cc(Nc2cc(F)c(C(=O)NC3CCN(C4COC4)CC3)cc2OC)nc2[nH]cc(C(F)(F)F)c12]

TABLE 2-continued
| Example | Chemical Structure |
|---|---|
| 72 | 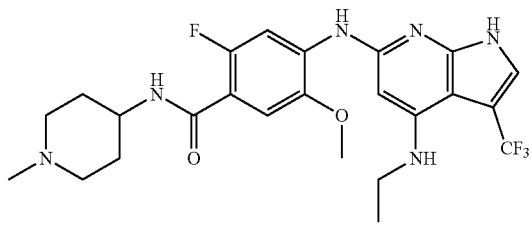 [SMILES: CCNc1cc(Nc2cc(F)c(C(=O)NC3CCN(C)CC3)cc2OC)nc2[nH]cc(C(F)(F)F)c12] |
TABLE 3
| Example | Chemical Structure |
|---|---|
| 73 | 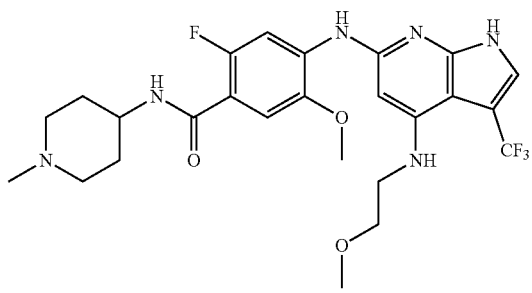 [SMILES: COCCNc1cc(Nc2cc(F)c(C(=O)NC3CCN(C)CC3)cc2OC)nc2[nH]cc(C(F)(F)F)c12] |
| 74 | 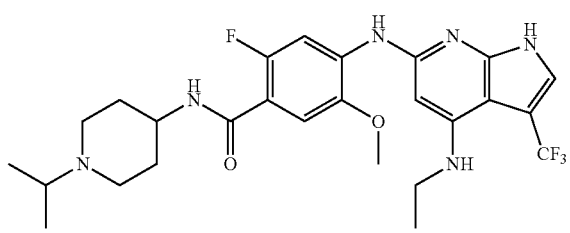 [SMILES: CCNc1cc(Nc2cc(F)c(C(=O)NC3CCN(C(C)C)CC3)cc2OC)nc2[nH]cc(C(F)(F)F)c12] |
| 75 | 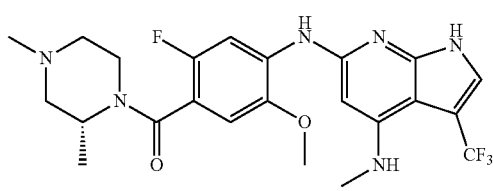 [SMILES: CNc1cc(Nc2cc(F)c(C(=O)N3CCN(C)C[C@H]3C)cc2OC)nc2[nH]cc(C(F)(F)F)c12] |
| 76 | 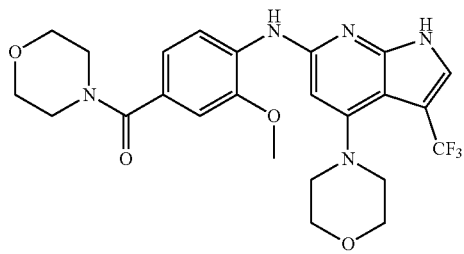 [SMILES: COc1cc(C(=O)N2CCOCC2)ccc1Nc1cc(N2CCOCC2)c2c(C(F)(F)F)c[nH]c2n1] |

TABLE 3-continued
| Example | Chemical Structure |
|---|---|
| 77 | 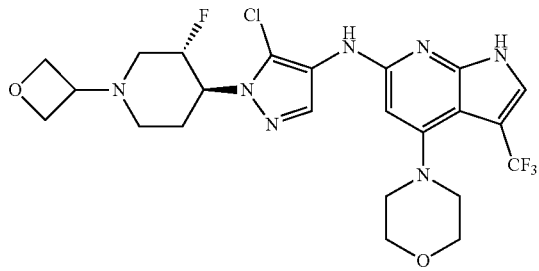 [SMILES: F[C@H]1CN(C2COC2)CC[C@@H]1n1ncc(Nc2cc(N3CCOCC3)c3c(C(F)(F)F)c[nH]c3n2)c1Cl] |
| 78 | 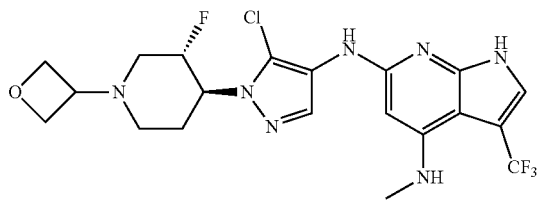 [SMILES: CNc1cc(Nc2cnn([C@H]3CCN(C4COC4)C[C@@H]3F)c2Cl)nc2[nH]cc(C(F)(F)F)c12] |
| 79 | 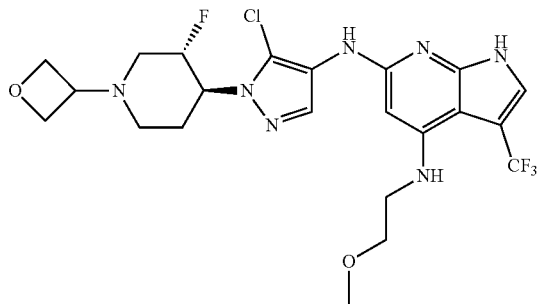 [SMILES: COCCNc1cc(Nc2cnn([C@H]3CCN(C4COC4)C[C@@H]3F)c2Cl)nc2[nH]cc(C(F)(F)F)c12] |
| 80 | 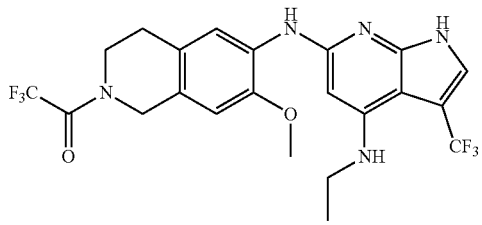 [SMILES: CCNc1cc(Nc2cc3c(cc2OC)CN(C(=O)C(F)(F)F)CC3)nc2[nH]cc(C(F)(F)F)c12] |
| 81 | 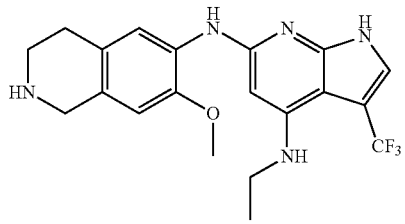 [SMILES: CCNc1cc(Nc2cc3c(cc2OC)CNCC3)nc2[nH]cc(C(F)(F)F)c12] |
| 82 | 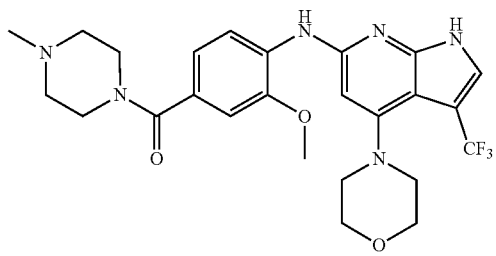 [SMILES: COc1cc(C(=O)N2CCN(C)CC2)ccc1Nc1cc(N2CCOCC2)c2c(C(F)(F)F)c[nH]c2n1] |

TABLE 3-continued
| Example | Chemical Structure |
|---|---|
| 83 | 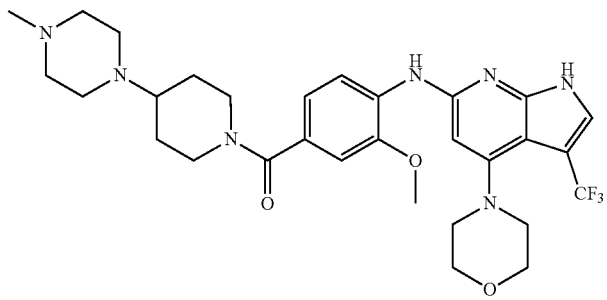 [SMILES: COc1cc(C(=O)N2CCC(N3CCN(C)CC3)CC2)ccc1Nc1cc(N2CCOCC2)c2c(C(F)(F)F)c[nH]c2n1] |
| 84 | 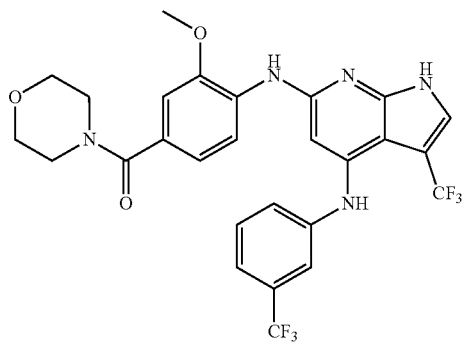 [SMILES: COc1cc(C(=O)N2CCOCC2)ccc1Nc1cc(Nc2cccc(C(F)(F)F)c2)c2c(C(F)(F)F)c[nH]c2n1] |
| 85 | 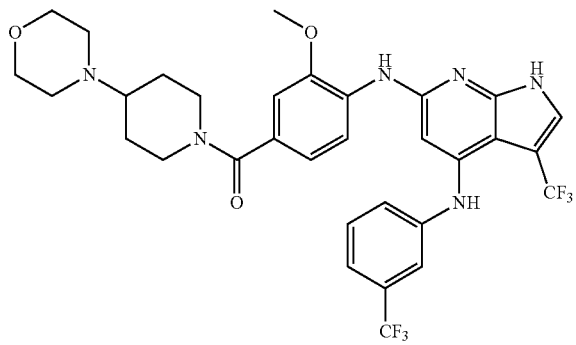 [SMILES: COc1cc(C(=O)N2CCC(N3CCOCC3)CC2)ccc1Nc1cc(Nc2cccc(C(F)(F)F)c2)c2c(C(F)(F)F)c[nH]c2n1] |
| 86 | 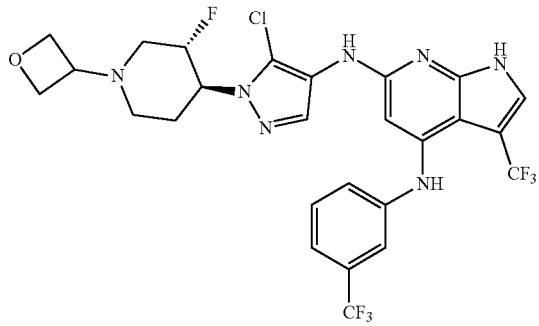 [SMILES: F[C@H]1CN(C2COC2)CC[C@@H]1n1ncc(Nc2cc(Nc3cccc(C(F)(F)F)c3)c3c(C(F)(F)F)c[nH]c3n2)c1Cl] |
| 87 | 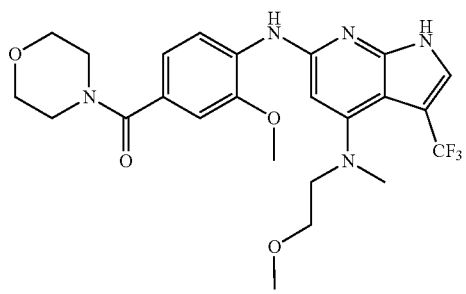 [SMILES: COCCN(C)c1cc(Nc2ccc(C(=O)N3CCOCC3)cc2OC)nc2[nH]cc(C(F)(F)F)c12] |

TABLE 3-continued
| Example | Chemical Structure |
|---|---|
| 88 | 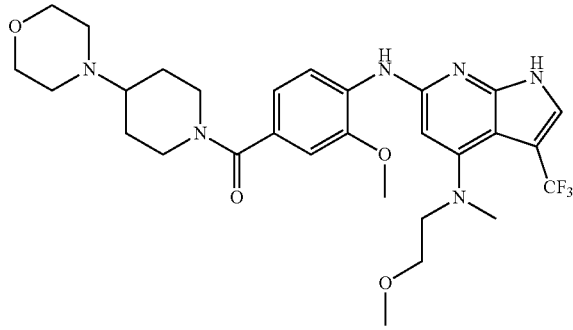 [SMILES: COCCN(C)c1cc(Nc2ccc(C(=O)N3CCC(N4CCOCC4)CC3)cc2OC)nc2[nH]cc(C(F)(F)F)c12] |
| 89 | 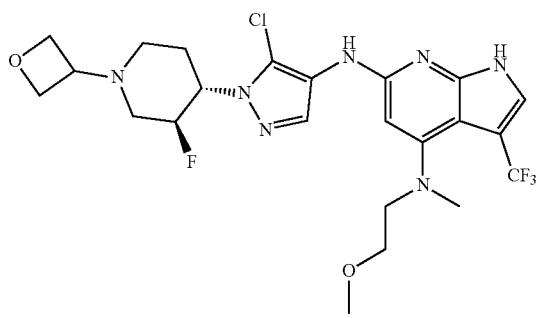 [SMILES: COCCN(C)c1cc(Nc2cnn([C@H]3CCN(C4COC4)C[C@@H]3F)c2Cl)nc2[nH]cc(C(F)(F)F)c12] |
| 90 | 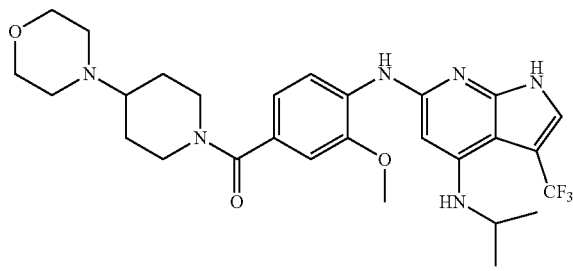 [SMILES: COc1cc(C(=O)N2CCC(N3CCOCC3)CC2)ccc1Nc1cc(NC(C)C)c2c(C(F)(F)F)c[nH]c2n1] |
| 91 | 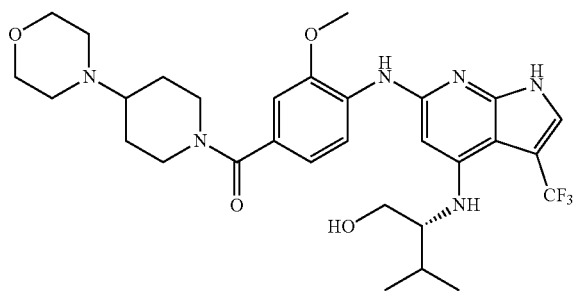 [SMILES: COc1cc(C(=O)N2CCC(N3CCOCC3)CC2)ccc1Nc1cc(N[C@@H](CO)C(C)C)c2c(C(F)(F)F)c[nH]c2n1] |
| 92 | 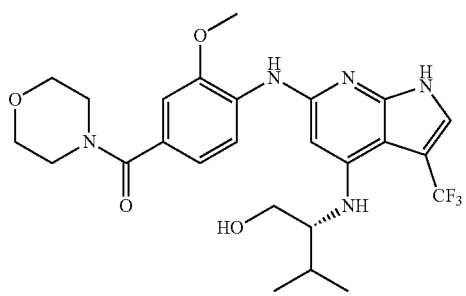 [SMILES: COc1cc(C(=O)N2CCOCC2)ccc1Nc1cc(N[C@@H](CO)C(C)C)c2c(C(F)(F)F)c[nH]c2n1] |

TABLE 3-continued
| Example | Chemical Structure |
|---|---|
| 93 | 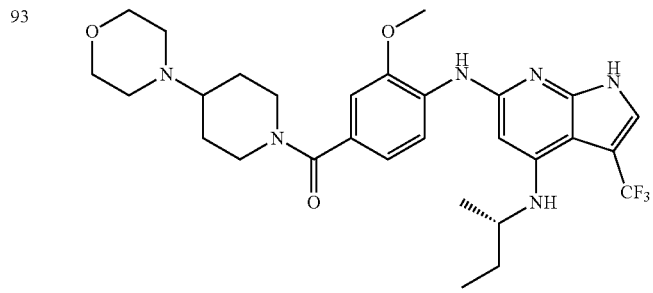 |
| 94 | 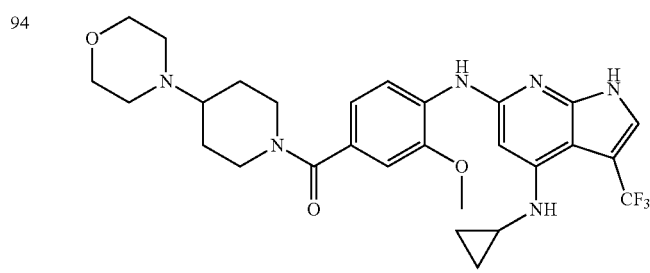 |
| 95 | 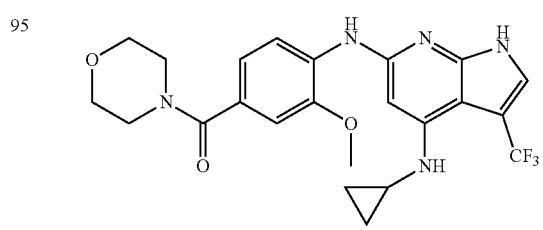 |
| 96 | 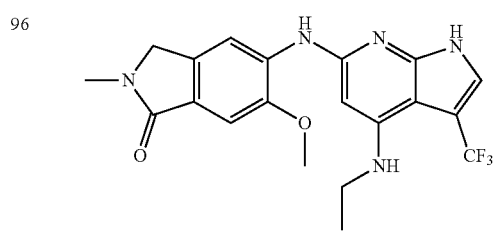 |
| 97 | 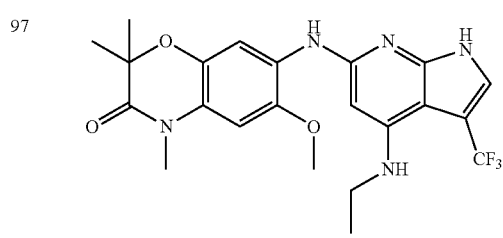 |
| 98 | 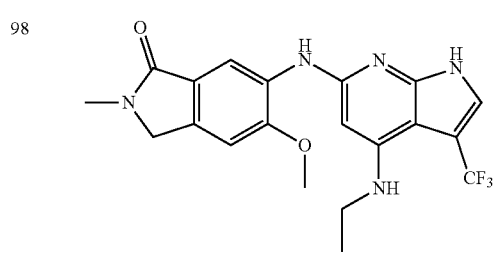 |

TABLE 3-continued
| Example | Chemical Structure |
|---|---|
| 99 | 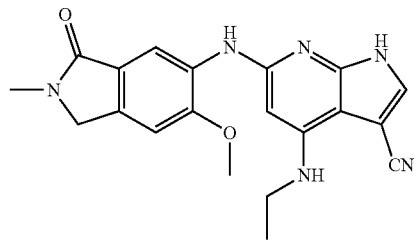 [SMILES: CCNc1cc(Nc2cc3c(cc2OC)CN(C)C3=O)nc2[nH]cc(C#N)c12] |
| 100 | 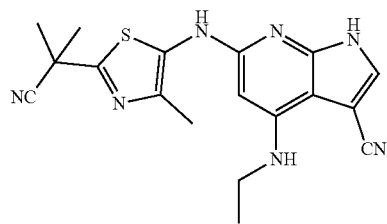 [SMILES: CCNc1cc(Nc2sc(C(C)(C)C#N)nc2C)nc2[nH]cc(C#N)c12] |
| 101 | 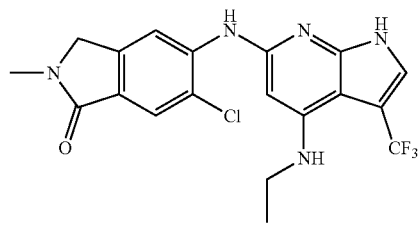 [SMILES: CCNc1cc(Nc2cc3c(cc2Cl)C(=O)N(C)C3)nc2[nH]cc(C(F)(F)F)c12] |
| 102 | 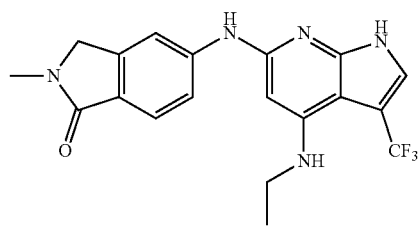 [SMILES: CCNc1cc(Nc2ccc3c(c2)CN(C)C3=O)nc2[nH]cc(C(F)(F)F)c12] |
| 103 | 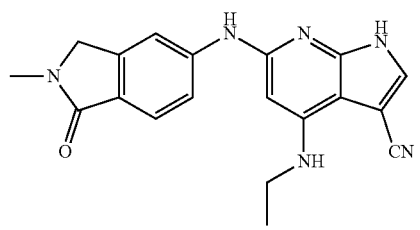 [SMILES: CCNc1cc(Nc2ccc3c(c2)CN(C)C3=O)nc2[nH]cc(C#N)c12] |
| 104 | 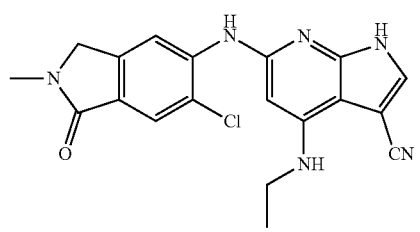 [SMILES: CCNc1cc(Nc2cc3c(cc2Cl)C(=O)N(C)C3)nc2[nH]cc(C#N)c12] |

TABLE 3-continued

| Example | Chemical Structure |
|---|---|
| 105 | 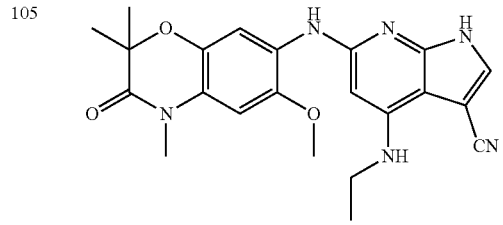 |

TABLE 4

| Example | Name | ¹H NMR; MS(ESI) m/z | Yield (%) | HPLC r.t. (min) (method) |
|---|---|---|---|---|
| 1 | 6-((2-methoxy-4-(morpholine-4-carbonyl)phenyl)amino)-4-(methylamino)-1H-pyrrolo[2,3-b]pyridine-3-carbonitrile | ¹H NMR (400 MHz, TFA salt, DMSO-d₆) δ 12.15 (br s, 1H), 8.49 (br s, 1H), 8.31 (br s, 1H), 7.87 (d, J = 2.1 Hz, 1H), 7.07 (s, 1H), 6.99 (dd, J = 1.5, 8.2 Hz, 1H), 6.14 (s, 1H), 3.89 (s, 3H), 3.62 (br s, 4H), 3.54 (br s, 4H), 2.89 (s, 3H); 407 [M + H]⁺ | 67 | 1.762 (B) |
| 2 | 4-(ethylamino)-6-((2-methoxy-4-(morpholine-4-carbonyl)phenyl)amino)-1H-pyrrolo[2,3-b]pyridine-3-carbonitrile | ¹H NMR (400 MHz, TFA salt, DMSO-d6) δ 12.10 (s, 1H), 8.47 (br s, 1H), 8.34 (br s, 1H), 7.85 (s, 1H), 7.04 (s, 1H), 6.96 (d, J = 8.2 Hz, 1H), 6.24 (s, 1H), 5.51 (br s, 1H), 3.89 (s, 3H), 3.67-3.44 (m, 8H), 3.27 (m, 2H), 1.24 (t, J = 7.1 Hz, 3H); 421 [M + H]⁺ | 82 | 4.75 |
| 3 | 6-((2-methoxy-4-(4-morpholino-piperidine-1-carbonyl)phenyl)amino)-4-((2-methoxyethyl)amino)-1H-pyrrolo[2,3-b]pyridine-3-carbonitrile | 534 [M + H]⁺ | 48 | 3.984 |
| 4 | 6-((2-methoxy-4-(morpholine-4-carbonyl)phenyl)amino)-4-((2-methoxyethyl)amino)-1H-pyrrolo[2,3-b]pyridine-3-carbonitrile | ¹H NMR (400 MHz, DMSO-d6) δ 12.11 (s, 1H), 8.63 (d, J = 8.6 Hz, 1H), 8.07 (s, 1H), 7.84 (s, 1H), 7.02 (s, 1H), 6.95 (d, J = 8.3 Hz, 1H), 6.33 (s, 1H), 5.38 (t, J = 5.4 Hz, 1H), 3.90 (s, 3H), 3.62-3.59 (m, 12H), 3.32 (s, 3H); 451 [M + H]⁺ CH₂Cl₂ Hexrecrystallization | 81 | 4.768 |
| 5 | 4-((2-methoxyethyl)amino)-6-((3,4,5-trimethoxyphenyl)amino)-1H-pyrrolo[2,3-b]pyridine-3-carbonitrile | ¹H NMR (400 MHz, DMSO-d6) δ 11.99 (s, 1H), 8.76 (s, 1H), 7.83 (s, 1H), 7.14 (s, 2H), 5.84 (s, 1H), 5.35 (m, 1H), 3.76 (s, 6H), 3.59 (m, 7H), 3.31 (s, 3H); 398 [M + H]⁺ CH₂Cl₂ Hexrecrystallization | 66 | 5.071 |
| 6 | 4-((2-methoxyethyl)amino)-6-((1-methyl-1H-pyrazol-4-yl)amino)-1H-pyrrolo[2,3-b]pyridine-3-carbonitrile | 312 [M + H]⁺ | 36 | 4.271 |
| 7 | 4-((2-methoxyethyl)amino)-6-((1-methyl-1H-pyrazol-3-yl)amino)-1H-pyrrolo[2,3-b]pyridine-3-carbonitrile | ¹H NMR (400 MHz, TFA salt, DMSO-d6) δ 12.04 (s, 1H), 9.04 (s, 1H), 7.92 (s, 1H), 7.83 (s, 1H), 5.96 (br s, 1H), 5.76 (s, 2H), 3.82 (s, 3H), 3.59 (br s, 2H), 3.40 (br s, 2H), 3.31 (s, 3H); 312 [M + H]⁺ | 57 | 4.071 |
| 8 | 4-(ethylamino)-6-((3,4,5-trimethoxyphenyl)amino)-1H-pyrrolo[2,3-b]pyridine-3-carbonitrile | ¹H NMR (400 MHz, DMSO-d6) δ 11.97 (S, 1H), 8.75 (s, 1H), 7.82 (s, 1H), 7.14 (s, 2H), 5.82 (s, 1H), 5.26 (br t, J = 5.3 Hz, 1H), 3.76 (s, 6H), 3.59 (s, 3H), 3.22 (m, 2H), 1.24 (t, J = 7.1 Hz, 3H); 398 [M + H]⁺ CH₂Cl₂, Hexrecrystallization | 68 | 5.148 |
| 9 | 6-((2-methoxy-4-(4-morpholino-piperidine-1-carbonyl)phenyl)amino)-4-(propylamino)-1H-pyrrolo[2,3-b]pyridine-3-carbonitrile | ¹H NMR (400 MHz, TFA salt, DMSO-d6) δ 12.09 (s, 1H), 9.90 (s, 1H), 8.55 (d, J = 8.0 Hz, 1H), 8.21 (br s, 1H), 7.84 (s, 1H), 7.01 (s, 1H), 6.96 (d, J = 8.2 Hz, 1H), 6.27 (s, 1H), 5.42 (br s, 1H), 4.02 (br d, J = 11.6 Hz, 2H), 3.89 (s, 3H), 3.60-3.42 (m, 7H), 3.19 (br t, J = 6.8 Hz, 2H), 3.13 (m, 2H), 2.96 (m, 2H), 3.09 (m, 2H), 1.67 (m, 2H), 1.58 (m, 2H), 0.98 (t, J = 7.3 Hz, 3H); 518 [M + H]⁺ | 50 | 4.336 |
| 10 | 6-((2-methoxy-4-(morpholine-4-carbonyl)phenyl)amino)-4- | ¹H NMR (400 MHz, TFA salt, DMSO-d6) δ 12.11 (s, 1H), 8.44 (br s, 1H), 8.37 (br s, 1H), | 36 | 5.134 |

TABLE 4-continued

| Example | Name | ¹H NMR; MS(ESI) m/z | Yield (%) | HPLC r.t. (min) (method) |
|---|---|---|---|---|
|  | (propylamino)-1H-pyrrolo[2,3-b]pyridine-3-carbonitrile | 7.85 (s, 1H), 7.04 (s, 1H), 6.96 (d, J = 8.2 Hz, 1H), 6.24 (s, 1H), 5.53 (br s, 1H), 3.60 (m, 4H), 3.52 (m, 4H), 3.19 (t, J = 7.0 Hz, 2H), 1.65 (m, 2H), 0.97 (t, J = 7.3 Hz, 3H): 435 [M + H]⁺ |  |  |
| 11 | 4-(propylamino)-6-((3,4,5-trimethoxyphenyl)amino)-1H-pyrrolo[2,3-b]pyridine-3-carbonitrile | ¹H NMR (400 MHz, TFA salt, DMSO-d6) δ 11.99 (s, 1H), 8.85 (br s, 1H), 7.84 (s, 1H), 7.09 (s, 2H), 5.83 (s, 1H), 5.45 (br s, 1H), 3.77 (s, 6H), 3.60 (s, 3H), 3.16 (br t, J = 6.5 Hz, 2H), 1.66 (m, 2H), 0.97 (t, J = 7.3 Hz, 3H): 382 [M + H]⁺ | 35 | 5.307 |
| 12 | 6-((1-methyl-1H-pyrazol-4-yl)amino)-4-(propylamino)-1H-pyrrolo[2,3-b]pyridine-3-carbonitrile | ¹H NMR (400 MHz, TFA salt, DMSO-d6) δ 11.92 (s, 1H), 8.90 (br s, 1H), 7.92 (s, 1H), 7.80 (s, 1H), 7.48 (s, 1H), 5.74 (s, 1H), 3.81 (s, 3H), 3.18 (t, J = 7.0 Hz, 2H), 1.66 (m, 2H), 0.95 (t, J = 7.3 Hz, 3H): 296 [M + H]⁺ | 51 | 4.697 |
| 13 | 6-((1-methyl-1H-pyrazol-3-yl)amino)-4-(propylamino)-1H-pyrrolo[2,3-b]pyridine-3-carbonitrile | ¹H NMR (400 MHz, TFA salt, DMSO-d6) δ 12.76 (br s, 1H), 10.35 (s, 1H), 7.95 (s, 1H), 7.69 (d, J = 1.8 Hz, 1H), 6.35 (br s, 1H), 6.14 (d, J = 1.8 Hz, 1H), 6.13 (s, 1H), 3.82 (s, 3H), 3.24 (br s, 2H), 1.67 (m, 2H), 0.97 (t, J = 7.2 Hz, 3H): 296 [M + H]⁺ | 52 | 4.973 |
| 14 | 4-(ethylamino)-6-((1-methyl-1H-pyrazol-4-yl)amino)-1H-pyrrolo[2,3-b]pyridine-3-carbonitrile | ¹H NMR (400 MHz, TFA salt, DMSO-d6) δ 11.85 (s, 1H), 8.89 (s, 1H), 7.75 (s, 1H), 7.47 (s, 1H), 6.50 (s, 1H), 6.16 (s, 1H), 5.18 (t, J = 5.2 Hz, 1H), 3.71 (s, 3H), 3.20 (m, 2H), 1.24 (t, J = 7.1 Hz, 3H): 282 [M + H]⁺ | 34 | 4.696 |
| 15 | 4-(ethylamino)-6-((1-methyl-1H-pyrazol-3-yl)amino)-1H-pyrrolo[2,3-b]pyridine-3-carbonitrile | ¹H NMR (400 MHz, TFA salt, DMSO-d6) δ 11.85 (s, 1H), 8.54 (s, 1H), 7.90 (s, 1H), 7.72 (s, 1H), 7.42 (s, 1H), 5.67 (s, 1H), 5.15 (t, J = 5.3 Hz, 1H), 3.77 (s, 3H), 3.19 (m, 2H), 1.23 (t, J = 7.1 Hz, 3H): 282 [M + H]⁺ | 46 | 4.415 |
| 16 | 6-((2-methoxy-4-(4-morpholino-piperidine-1-carbonyl)phenyl)amino)-4-(methylamino)-1H-pyrrolo[2,3-b]pyridine-3-carbonitrile | ¹H NMR (400 MHz, TFA salt, DMSO-d6) δ 12.15 (br s, 1H), 9.98 (br s, 1H), 8.39 (br s, 2H), 7.85 (d, J = 2.6 Hz, 1H), 7.02 (s, 1H), 6.96 (dd, J = 1.6, 8.2 Hz, 1H), 6.15 (s, 1H), 4.01 (d, J = 11.6 Hz, 4H), 3.88 (s, 3H), 3.66 (t, J = 11.9 Hz, 3H), 3.49-3.41 (m, 4H), 3.12 (br s, 2H), 2.09-2.07 (m, 2H), 1.62-1.54 (m, 2H); 490 [M + H]⁺ | 50 | 4.128 |
| 17 | 6-((5-fluoro-2-methoxy-4-(4-morpholino-piperidine-1-carbonyl)phenyl)amino)-4-(methylamino)-1H-pyrrolo[2,3-b]pyridine-3-carbonitrile | ¹H NMR (400 MHz, TFA salt, DMSO-d6) δ 12.16 (br s, 1H), 9.95 (br s, 1H), 8.64 (d, J = 12.9 Hz, 1H), 8.35 (br s, 1H), 7.86 (s, 1H), 6.90 (d, J = 6.4 Hz, 1H), 6.30 (s, 1H), 4.62 (d, J = 12.0 Hz, 1H), 4.01 (d, J = 12.0 Hz, 2H), 3.87 (s, 3H), 3.68-3.62 (m, 3H), 3.44 (br s, 3H), 3.10 (br s, 3H), 2.85 (s, 3H), 2.78-2.72 (m, 1H), 2.16-2.05 (m, 2H), 1.56-1.54 (m, 2H); 508 [M + H]⁺ | 50 | 4.273 |
| 18 | 4-(ethylamino)-6-((2-methoxy-4-(4-morpholino-piperidine-1-carbonyl)phenyl)amino)-1H-pyrrolo[2,3-b]pyridine-3-carbonitrile | 504 [M + H]⁺ | 69 | 4.112 |
| 19 | 6-((5-fluoro-2-methoxy-4-(morpholine-4-carbonyl)phenyl)amino)-4-(methylamino)-1H-pyrrolo[2,3-b]pyridine-3-carbonitrile | ¹H NMR (400 MHz, TFA salt, DMSO-d₆) δ 12.18 (br s, 1H), 8.58 (d, J = 12.8 Hz, 1H), 8.40 (br s, 1H), 7.86 (s, 1H), 6.94 (d, J = 6.4 Hz, 1H), 6.28 (s, 1H), 3.88 (s, 3H), 3.63 (br s, 4H), 3.55 (br s, 2H), 3.31 (br s, 2H), 2.86 (s, 3H); 425 [M + H]⁺ | 82 | 1.839 (B) |
| 20 | 6-((2-methoxy-4-(morpholine-4-carbonyl)phenyl)amino)-4-((2-methoxyethyl)(methyl)amino)-1H-pyrrolo[2,3-b]pyridine-3-carbonitrile | ¹H NMR (400 MHz, TFA salt, DMSO-d6) δ 12.4 (s, 1H), 8.59 (d, J = 8.28 Hz, 1H), 8.29 (s, 1H), 7.96 (s, 1H), 7.03 (s, 1H), 6.96 (d, J = 8.28 Hz, 1H), 6.57 (s, 1H), 3.90 (s, 3H), 3.61-3.53 (m, 12H), 3.21 (s, 3H), 2.98 (s, 3H); 465 [M + H]⁺ | 3 | 5.013 |
| 21 | 6-((5-fluoro-2-methoxy-4-(morpholine-4-carbonyl)phenyl)amino)-4-((2-methoxyethyl)(methyl)amino)-1H-pyrrolo[2,3-b]pyridine-3-carbonitrile | ¹H NMR (400 MHz, TFA salt, DMSO-d₆) δ 12.32 (s, 1H), 8.68 (d, J = 12.92 Hz, 1H), 8.46 (s, 1H), 8.00 (s, 1H), 6.94 (d, J = 6.4 Hz, 1H), 6.66 (s, 1H), 3.89 (s, 3H), 3.63-3.57 (m, 10H), 3.32 (s, 2H), 3.20 (s, 3H), 2.98 (s, 3H); 483 [M + H]⁺ | 2 | 5.655 |
| 22 | (R)-6-((2-methoxy-4-(2-methylmorpholine-4-carbonyl)phenyl)amino)-4-(methylamino)-1H-pyrrolo[2,3-b]pyridine-3-carbonitrile | ¹H NMR (400 MHz, TFA salt, DMSO-d₆) δ 12.07 (s, 1H), 8.55 (br, 1H), 8.13 (s, 1H), 7.83 (d, J = 2.8 Hz, 1H), 7.02 (s, 1H), 6.96-6.94 (m, 1H), 6.20 (s, 1H), 3.89 (s, 3H), 3.85-3.78 (m, 2H), 2.86 (s, 3H), 2.67-2.66 (m, 1H), 2.33-2.32 (m, 4H), 1.08 (d, J = 4.4 Hz 3H); 421 [M + H]⁺ | 17 | 4.724 |

TABLE 4-continued

| Example | Name | ¹H NMR; MS(ESI) m/z | Yield (%) | HPLC r.t. (min) (method) |
|---|---|---|---|---|
| 23 | (S)-6-((2-methoxy-4-(2-methylmorpholine-4-carbonyl)phenyl)amino)-4-(methylamino)-1H-pyrrolo[2,3-b]pyridine-3-carbonitrile | ¹H NMR (400 MHz, TFA salt, DMSO-$d_6$) δ 12.07 (s, 1H), 8.48 (br, 1H), 8.28 (s, 1H), 7.83 (d, J = 2.6 Hz, 1H), 7.03 (s, 1H), 6.97-6.94 (m, 1H), 6.18 (s, 1H), 3.89 (s, 3H), 3.85-3.78 (m, 2H), 2.87 (s, 3H), 2.73-2.32 (m, 4H), 2.34-2.30 (m, 3H); 421 [M + H]⁺ | 19 | 5.033 |
| 24 | 6-((4-((2R,6S)-2,6-dimethyl-morpholine-4-carbonyl)-2-methoxyphenyl)amino)-4-(methylamino)-1H-pyrrolo[2,3-b]pyridine-3-carbonitrile | ¹H NMR (400 MHz, TFA salt, DMSO-$d_6$) δ 12.07 (s, 1H), 8.54 (br, 1H), 8.18 (s, 1H), 7.83 (d, J = 2.9 Hz, 1H), 7.02 (d, J = 1.6 Hz, 1H), 6.96-6.93 (m, 1H), 6.19 (s, 1H), 3.89 (s, 3H), 3.57-3.52 (m, 2H), 2.86 (s, 3H), 2.70-2.32 (m, 4H), 1.19-0.97 (m, 6H); 435 [M + H]⁺ | 18 | 5.234 |
| 25 | 6-((4-(4,4-difluoro-piperidine-1-carbonyl)-2-methoxyphenyl)amino)-4-(methylamino)-1H-pyrrolo[2,3-b]pyridine-3-carbonitrile | ¹H NMR (400 MHz, TFA salt, DMSO-$d_6$) δ 12.07 (s, 1H), 8.60 (br, 1H), 8.09 (s, 1H), 7.82 (d, J = 2.9 Hz, 1H), 7.06 (d, J = 1.4 Hz, 1H), 7.00-6.97 (m, 1H), 6.21 (s, 1H), 3.90 (s, 3H), 3.66-3.57 (m, 4H), 2.90 (s, 3H), 2.08-2.00 (m, 4H); 441 [M + H]⁺ | 19 | 5.478 |
| 26 | (R)-4-(ethylamino)-6-((2-methoxy-4-(2-methylmorpholine-4-carbonyl)phenyl)amino)-1H-pyrrolo[2,3-b]pyridine-3-carbonitrile | ¹H NMR (400 MHz, TFA salt, DMSO-$d_6$) δ 12.12 (s, 1H), 8.38 (NH, 2H), 7.85 (s, 1H), 7.05 (s, 1H), 6.98 (d, J = 8.2 Hz, 1H), 6.22 (s, 1H), 5.33-4.52 (m, 4H), 3.89 (s, 3H), 3.86-3.77 (m, 1H), 3.56-3.43 (m, 2H), 3.32-3.23 (m, 2H), 1.27 (t, J = 7.1 Hz, 3H), 1.08 (s, 3H); 435 [M + H]⁺ | 48 | 4.986 |
| 27 | (S)-4-(ethylamino)-6-((2-methoxy-4-(2-methylmorpholine-4-carbonyl)phenyl)amino)-1H-pyrrolo[2,3-b]pyridine-3-carbonitrile | ¹H NMR (400 MHz, TFA salt, DMSO-$d_6$) δ 12.14 (s, 1H), 8.38 (NH, 2H), 7.87 (s, 1H), 7.07 (s, 1H), 6.99 (d, J = 8.2 Hz, 1H), 6.22 (s, 1H), 5.33-4.52 (m, 4H), 3.90 (s, 3H), 3.86-3.78 (m, 1H), 3.56-3.43 (m, 2H), 3.32-3.23 (m, 2H), 1.28 (t, J = 7.1 Hz, 3H), 1.10 (s, 3H); 435 [M + H]⁺ | 47 | 4.992 |
| 28 | 6-((4-((2R,6S)-2,6-dimethyl-morpholine-4-carbonyl)-2-methoxyphenyl)amino)-4-(ethylamino)-1H-pyrrolo[2,3-b]pyridine-3-carbonitrile | ¹H NMR (400 MHz, TFA salt, DMSO-$d_6$) δ 12.14 (s, 1H), 8.36 (NH, 2H), 7.84 (s, 1H), 7.04 (s, 1H), 6.97 (d, J = 8.2 Hz, 1H), 6.20 (s, 1H), 5.33-4.52 (m, 4H), 3.90 (s, 3H), 3.59-3.48 (m, 2H), 3.31-3.22 (m, 2H), 1.25 (t, J = 1.1 Hz, 3H), 1.07 (s, 6H); 449 [M + H]⁺ | 27 | 5.158 |
| 29 | 6-((4-(4,4-difluoropiperidine-1-carbonyl)-2-methoxyphenyl)amino)-4-(ethylamino)-1H-pyrrolo[2,3-b]pyridine-3-carbonitrile | ¹H NMR (400 MHz, TFA salt, DMSO-$d_6$) δ 12.18 (s, 1H), 8.46 (NH, 2H), 7.87 (s, 1H), 7.11 (s, 1H), 7.04 (d, J = 8.2 Hz, 1H), 6.21 (s, 1H), 3.90 (s, 3H), 3.70-3.55 (m, 4H), 3.32-3.26 (m, 2H), 2.09-2.01 (m, 4H), 1.28 (t, J = 7.1 Hz, 3H); 455 [M + H]⁺ | 34 | 5.356 |
| 30 | 6-((1,3-dimethyl-1H-pyrazol-4-yl)amino)-4-(ethylamino)-1H-pyrrolo[2,3-b]pyridine-3-carbonitrile | ¹H NMR (400 MHz, TFA salt, Methanol-$d_4$) δ 7.63 (s, 1H), 7.56 (s, 1H), 5.67 (s, 1H), 3.79 (s, 3H), 3.36-3.30 (m, 2H), 2.07 (s, 3H), 1.28 (t, J = 7.2 Hz, 3H); 296 [M + H]⁺ | 37 | 4.559 |
| 31 | 6-((1,5-dimethyl-1H-pyrazol-4-yl)amino)-4-(ethylamino)-1H-pyrrolo[2,3-b]pyridine-3-carbonitrile | ¹H NMR (400 MHz, TFA salt, Methanol-$d_4$) δ 7.56 (s, 1H), 7.40 (s, 1H), 5.67 (s, 1H), 3.77 (s, 3H), 3.36-3.30 (m, 2H), 2.14 (s, 3H), 1.28 (t, J = 7.2 Hz, 3H); 296 [M + H]⁺ | 38 | 4.546 |
| 32 | 4-(ethylamino)-6-((1-isopropyl-3-methyl-1H-pyrazol-4-yl)amino)-1H-pyrrolo[2,3-b]pyridine-3-carbonitrile | ¹H NMR (400 MHz, TFA salt, Methanol-$d_4$) δ 7.71 (s, 1H), 7.58 (s, 1H), 5.64 (s, 1H), 4.43-4.36 (m, 1H), 3.35-3.29 (m, 2H), 2.07 (s, 3H), 1.44 (d, J = 6.7 Hz, 6H), 1.28 (t, J = 7.2 Hz, 3H); 324 [M + H]⁺ | 36 | 4.892 |
| 33 | 4-(ethylamino)-6-((1-isopropyl-5-methyl-1H-pyrazol-4-yl)amino)-1H-pyrrolo[2,3-b]pyridine-3-carbonitrile | ¹H NMR (400 MHz, TFA salt, Methanol-$d_4$) δ 7.56 (s, 1H), 7.45 (s, 1H), 5.64 (s, 1H), 4.55-4.48 (m, 1H), 3.34-3.29 (m, 2H), 2.15 (s, 3H), 1.41 (d, J = 6.6 Hz, 6H), 1.27 (t, J = 7.2 Hz, 3H); 324 [M + H]⁺ | 33 | 4.862 |
| 34 | 6-((1,5-dimethyl-1H-pyrazol-4-yl)amino)-4-(methylamino)-1H-pyrrolo[2,3-b]pyridine-3-carbonitrile | ¹H NMR (400 MHz, TFA salt, Methanol-d4) δ 7.64 (s, 1H), 7.49 (s, 1H), 5.73 (s, 1H), 3.85 (s, 3H), 3.03 (s, 3H), 2.23 (s, 3H); 282 [M + H]⁺ | 5 | 4.302 |
| 35 | 6-((1,3-dimethyl-1H-pyrazol-4-yl)amino)-4-(methylamino)-1H-pyrrolo[2,3-b]pyridine-3-carbonitrile | ¹H NMR (400 MHz, TFA salt, Methanol-$d_4$) δ 7.72 (s, 1H), 7.65 (s, 1H), 5.72 (s, 1H), 3.87 (s, 3H), 3.03 (s, 3H), 2.14 (s, 3H); 282 [M + H]⁺ | 15 | 4.242 |
| 36 | 6-((1-isopropyl-3-methyl-1H-pyrazol-4-yl)amino)-4-(methylamino)-1H-pyrrolo[2,3-b]pyridine-3-carbonitrile | ¹H NMR (400 MHz, TFA salt, Methanol-$d_4$) δ 7.79 (s, 1H), 7.66 (s, 1H), 5.70 (s, 1H), 4.51-4.44 (m, 1H), 3.02 (s, 3H), 2.16 (s, 3H), 1.52 (d, J = 6.7 Hz, 6H); 310 [M + H]⁺ | 12 | 4.612 |
| 37 | 6-((1-isopropyl-5-methyl-1H-pyrazol-4-yl)amino)-4-(methylamino)-1H-pyrrolo[2,3- | ¹H NMR (400 MHz, TFA salt, Methanol-$d_4$) δ 7.65 (s, 1H), 7.54 (s, 1H), 5.70 (s, 1H), 4.62-4.59 (m, 1H), 3.02 (s, 3H), 2.24 (s, 3H), | 8 | 4.644 |

TABLE 4-continued

| Example | Name | ¹H NMR; MS(ESI) m/z | Yield (%) | HPLC r.t. (min) (method) |
|---|---|---|---|---|
|  | b]pyridine-3-carbonitrile | 1.50 (d, J = 6.7 Hz, 6H); 310 [M + H]⁺ |  |  |
| 38 | 6-((1-(2-cyanopropan-2-yl)-3-methyl-1H-pyrazol-4-yl)amino)-4-(methylamino)-1H-pyrrolo[2,3-b]pyridine-3-carbonitrile | ¹H NMR (400 MHz, TFA salt, Methanol-d₄) δ 8.08 (s, 1H), 7.69 (s, 1H), 5.75 (s, 1H), 3.05 (s, 3H), 2.22 (s, 3H), 2.04 (s, 6H); 335 [M + H]⁺ | 22 | 4.671 |
| 39 | 6-((3-methoxy-5-(morpholine-4-carbonyl)pyridin-2-yl)amino)-4-(methylamino)-1H-pyrrolo[2,3-b]pyridine-3-carbonitrile | ¹H NMR (400 MHz, TFA salt, Methanol-d₄) δ 7.90 (s, 1H), 7.75 (s, 1H), 7.47 (s, 1H), 6.44 (s, 1H), 3.97 (s, 3H), 3.76-3.41 (m, 8H), 2.99 (s, 3H); 408 [M + H]⁺ | 13 | 4.562 |
| 40 | 4-(ethylamino)-6-((3-methoxy-5-(morpholine-4-carbonyl)pyridin-2-yl)amino)-1H-pyrrolo[2,3-b]pyridine-3-carbonitrile | ¹H NMR (400 MHz, TFA salt, Methanol-d₄) δ 7.90 (s, 1H), 7.74 (s, 1H), 7.47 (s, 1H), 6.48 (s, 1H), 3.97 (s, 3H), 3.71-3.47 (m, 8H), 3.40-3.35 (m, 2H), 1.29 (t, J = 7.2 Hz, 3H); 422 [M + H]⁺ | 20 | 4.810 |
| 41 | 6-((5-chloro-1-((3S,4S)-3-fluoro-1-(oxetan-3-yl)piperidin-4-yl)-1H-pyrazol-4-yl)amino)(methylamino)-1H-pyrrolo[2,3-b]pyridine-3-carbonitrile | ¹H NMR (400 MHz, TFA salt, Methanol-d₄) δ 7.83 (s, 1H), 7.70 (s, 1H), 5.71 (s, 1H), 5.23-5.08 (m, 1H), 4.88-4.82 (m, 2H), 4.79-4.74 (m, 2H), 4.22-4.19 (m, 1H), 3.71-3.64 (m, 1H), 3.35-3.32 (m, 2H), 3.01 (s, 3H), 2.94-2.80 (m, 2H), 2.49-2.32 (m, 2H); 445 [M + H]⁺ | 12 | 4.177 |
| 42 | 6-((5-chloro-1-((3S,4S)-3-fluoro-1-(oxetan-3-yl)piperidin-4-yl)-1H-pyrazol-4-yl)amino)(ethylamino)-1H-pyrrolo[2,3-b]pyridine-3-carbonitrile | ¹H NMR (400 MHz, TFA salt, Methanol-d₄) δ 7.69 (s, 1H), 7.56 (s, 1H), 5.59 (s, 1H), 5.10-4.95 (m, 1H), 4.74-4.61 (m, 4H), 4.12-4.05 (m, 1H), 3.59-3.52 (m, 1H), 3.29-3.21 (m, 3H), 2.85-2.79 (m, 1H), 2.74-2.69 (m, 1H), 2.39-2.29 (m, 1H), 2.24-2.19 (m, 1H), 1.21 (t, J = 7.2 Hz, 3H); 459 [M + H]⁺ | 29 | 4.406 |
| 43 | (R)-4-(ethylamino)-6-((3-methoxy-5-(2-methylmorpholine-4-carbonyl)pyridin-2-yl)amino)-1H-pyrrolo[2,3-b]pyridine-3-carbonitrile | ¹H NMR (400 MHz, TFA salt, Methanol-d₄) δ 7.90 (s, 1H), 7.75 (s, 1H), 7.47 (s, 1H), 6.50 (s, 1H), 4.51-4.20 (m, 1H), 3.98 (s, 3H), 3.93-3.70 (m, 3H), 3.68-3.44 (m, 3H), 3.41-3.36 (m, 2H), 3.07-2.81 (m, 1H), 2.78-2.51 (m, 1H), 1.30 (t, J = 7.2 Hz, 3H), 1.07 (s, 3H); 436 [M + H]⁺ | 34 | 4.938 |
| 44 | (R)-6-((3-methoxy-5-(2-methylmorpholine-4-carbonyl)pyridin-2-yl)amino)-4-(methylamino)-1H-pyrrolo[2,3-b]pyridine-3-carbonitrile | ¹H NMR (400 MHz, TFA salt, Methanol-d₄) δ 7.87 (s, 1H), 7.71 (s, 1H), 7.44 (s, 1H), 6.39 (s, 1H), 4.47-4.16 (m, 1H), 3.94 (s, 3H), 3.88-3.67 (m, 1H), 3.65-3.37 (m, 3H), 3.32-3.08 (m, 1H), 2.96 (s, 3H), 2.83-2.48 (m, 1H), 1.05 (s, 3H); 422 [M + H]⁺ | 26 | 4.727 |
| 45 | 3-methoxy-4-((4-morpholino-3-(trifluoromethyl)-1H-pyrrolo[2,3-b]pyridin-6-yl)amino)phenyl)(4-methylpiperazin-1-yl)methanone | ¹H NMR (400 MHz, TFA salt, Methanol-d₄) δ 8.51 (d, J = 8.24 Hz, 1H), 7.55 (s, 1H), 7.18 (d, J = 1.68 Hz, 1H), 7.15 (dd, J = 8.24, 1.76 Hz, 1H), 6.57 (s, 1H), 4.49 (br s, 2H), 4.00 (s, 3H), 3.90 (t, J = 4.32 Hz, 4H), 3.57 (br s, 2H), 3.44 (br s, 2H), 3.22 (br s, 2H), 3.18 (t, J = 4.32, 4H), 2.99 (s, 3H); 519 [M + H]⁺ | 35 | 4.128 |
| 46 | (3-methoxy-4-((4-morpholino-3-(trifluoromethyl)-1H-pyrrolo[2,3-b]pyridin-6-yl)amino)phenyl)(4-(4-methylpiperazin-1-yl)piperidin-1-yl)methanone | 602 [M + H]⁺ | 41 | 4.795 |
| 47 | 4-methoxy-6-((2-methoxy-4-(4-morpholino-piperidine-1-carbonyl)phenyl)amino)-1H-pyrrolo[2,3-b]pyridine-3-carbonitrile | ¹H NMR (400 MHz, TFA salt, DMSO-d₆) δ 12.26 (br s, 1H), 8.64 (d, J = 8.3 Hz, 1H), 8.40 (s, 1H), 7.91 (d, J = 2.9 Hz, 1H), 7.02 (d, J = 1.6 Hz, 1H), 6.97 (dd, J = 1.6, 8.3 Hz, 1H), 6.79 (s, 1H), 4.02 (d, J = 11.6 Hz, 2H), 3.93 (s, 3H), 3.91 (s, 3H), 3.43 (d, J = 12.1 Hz, 4H), 3.15-3.11 (m, 3H), 2.09 (d, J = 9.0 Hz, 2H), 1.62-1.53 (m, 2H); 491 [M + H]⁺ | 33 | 2.219 (B) |
| 48 | 4-methoxy-6-((2-methoxy-4-(morpholine-4-carbonyl)phenyl)amino)-1H-pyrrolo[2,3-b]pyridine-3-carbonitrile | ¹H NMR (400 MHz, TFA salt, DMSO-d₆) δ 12.28 (br s, 1H), 8.63 (d, J = 8.3 Hz, 1H), 8.38 (s, 1H), 7.90 (d, J = 2.9 Hz, 1H), 7.04 (d, J = 1.8 Hz, 1H), 6.97 (dd, J = 1.8, 8.3 Hz, 1H), 6.79 (s, 1H), 3.92 (s, 3H), 3.90 (s, 3H), 3.60 (br s, 4H), 3.52 (br s, 4H); 408 [M + H]⁺ | 17 | 2.442 (B) |
| 49 | 4-ethoxy-6-((2-methoxy-4-(4-morpholino-piperidine-1-carbonyl)phenyl)amino)-1H-pyrrolo[2,3-b]pyridine-3-carbonitrile | ¹H NMR (400 MHz, TFA salt, DMSO-d₆) δ 12.24 (br s, 1H), 8.65 (d, J = 8.3 Hz, 1H), 8.39 (s, 1H), 7.91 (d, J = 2.9 Hz, 1H), 7.03 (d, J = 1.8 Hz, 1H), 6.98 (dd, J = 1.7, 8.3 Hz, 1H), 6.78 (s, 1H), 4.21 (q, J = 14.0 Hz, 2H), 4.03 (d, J = 11.8 Hz, 4H), 3.92 (s, 3H), 3.73-3.64 (m, 4H), 3.51-3.39 (m, 3H), 3.17-3.12 (m, 2H), | 51 | 2.282 (B) |

TABLE 4-continued

| Example | Name | ¹H NMR; MS(ESI) m/z | Yield (%) | HPLC r.t. (min) (method) |
|---|---|---|---|---|
| 50 | 4-ethoxy-6-((2-methoxy-4-(morpholine-4-carbonyl)phenyl)amino)-1H-pyrrolo[2,3-b]pyridine-3-carbonitrile | ¹H NMR (400 MHz, TFA salt, DMSO-$d_6$) δ 12.26 (br s, 1H), 8.64 (d, J = 8.3 Hz, 1H), 8.36 (s, 1H), 7.90 (d, J = 2.9 Hz, 1H), 6.98 (dd, J = 1.8, 8.3 Hz, 1H), 6.77 (s, 1H), 4.21 (q, J = 14.0 Hz, 2H), 3.91 (s, 3H), 3.61 (br s, 4H), 3.54 (br s, 4H), 1.43 (t, J = 7.0 Hz, 3H); 422 [M + H]⁺ | 51 | 2.525 (B) |
| 51 | (R6-((3-methoxy-5-(2-methylmorpholine-4-carbonyl)pyridin-2-yl)amino)-4-(1-methylcyclopropoxy)-1H-pyrrolo[2,3-b]pyridine-3-carbonitrile | ¹H NMR (400 MHz, TFA salt, Methanol-$d_4$) δ 8.40 (s, 1H), 7.85 (s, 1H), 7.62 (s, 1H), 7.19 (s, 1H), 3.90 (s, 3H), 3.85-3.74 (m, 1H), 3.55-3.44 (m, 2H), 2.12-2.02 (m, 1H), 1.97-1.88 (m, 1H), 1.62 (s, 3H), 1.55-0.44 (m, 1H), 1.17 (s, 3H), 1.10-0.98 (m, 5H); 463 [M + H]⁺ | 30 | 5.055 |
| 52 | 6-((3-methoxy-5-(morpholine-4-carbonyl)pyridin-2-yl) amino)-4-(1-methylcyclopropoxy)-1H-pyrrolo[2,3-b]pyridine-3-carbonitrile | ¹H NMR (400 MHz, TFA salt, Methanol-$d_4$) δ 8.01 (s, 1H), 7.95 (s, 1H), 7.77 (s, 1H), 7.48 (s, 1H), 4.18 (s, 3H), 3.88-3.60 (m, 8H), 1.73 (s, 3H), 1.23-1.11 (m, 2H), 1.02-0.87 (m, 2H); 449 [M + H]⁺ | 5 | 5.202 |
| 53 | $N^4$-ethyl-3-(trifluoromethyl)-$N^6$-(3,4,5-trimethoxyphenyl)-1H-pyrrolo[2,3-b]pyridine-4,6-diamine | ¹H NMR (400 MHz, TFA salt, DMSO-d6) δ 11.76 (s, 1H), 8.99 (br s, 1H), 7.55 (s, 1H), 7.09 (br s, 2H), 5.85 (s, 1H), 5.01 (br s, 1H), 3.77 (s, 6H), 3.61 (s, 3H), 3.27 (m, 2H), 1.24 (t, J = 7.1 Hz, 3H): 411 [M + H]⁺ | 25 | 5.552 |
| 54 | $N^4$-ethyl-$N^6$-(1-methyl-1H-pyrazol-3-yl)-3-(trifluoromethyl)-1H-pyrrolo[2,3-b]pyridine-4,6-diamine | 325 [M + H]⁺ | — | — |
| 55 | $N^4$-ethyl-$N^6$-(1-methyl-1H-pyrazol-4-yl)-3-(trifluoromethyl)-1H-pyrrolo[2,3]-b]pyridine-4,6-diamine | ¹H NMR (400 MHz, TFA salt, DMSO-d6) δ 11.64 (s, 1H), 8.86 (br s, 1H), 7.93 (s, 1H), 7.49 (s, 2H), 5.71 (s, 1H), 5.21 (br s, 1H), 3.82 (s, 3H), 3.27 (m, 2H), 1.22 (t, J = 7.1 Hz, 3H): 325 [M + H]⁺ | 41 | 4.986 |
| 56 | (4-((4-(ethylamino)-3-(trifluoromethyl)-1H-pyrrolo[2,3-b]pyridin-6-yl)amino)-3-methoxyphenyl)(morpholino)methanone | ¹H NMR (400 MHz, TFA salt, DMSO-d6) δ 11.85 (s, 1H), 8.38 (br s, 1H), 7.55 (s, 1H), 7.06 (s, 1H), 6.98 (d, J = 8.2 Hz, 1H), 6.20 (s, 1H), 5.06 (br s, 1H), 3.89 (s, 3H), 3.61 (m, 4H), 3.52 (m, 4H), 3.30 (m, 2H), 1.23 (t, J = 7.1 Hz, 3H): 464 [M + H]⁺ | 25 | 5.228 |
| 57 | (4-((4-(ethylamino)-3-(trifluoromethyl)-1H-pyrrolo[2,3-b]pyridin-6-yl)amino)-3-methoxyphenyl)(4-morpholino-piperidin-1-yl)methanone | ¹H NMR (400 MHz, HCl salt, DMSO) δ 11.99 (s, 1H), 11.29 (s, 1H), 9.01 (br s, 1H), 8.20 (br s, 1H), 7.59 (s, 1H), 7.11 (s, 1H), 7.02 (d, J = 8.1 Hz, 1H), 6.12 (s, 1H), 5.41 (br s, 1H), 4.59-3.91 (m, 4H), 3.89 (s, 3H), 3.87-3.80 (m, 2H), 3.38-3.19 (m, 1H), 3.15-2.79 (m, 4H), 2.25-2.12 (m, 2H), 1.76-1.66 (m, 2H), 1.25 (d, J = 7.1 Hz, 3H); 547 [M + H]⁺ | 24 | 4.595 |
| 58 | (3-methoxy-4-((4-(methylamino)-3-(trifluoromethyl)-1H-pyrrolo[2,3-b]pyridin-6-yl)amino)phenyl)(morpholino)methanone | ¹H NMR (400 MHz, TFA salt, Methanol-$d_4$) δ 7.52 7.47 (m, 2H), 7.24 (d, J = 1.4 Hz, 1H), 7.12 (dd, J = 8.0, 1.6 Hz, 1H), 5.94 (s, 1H), 3.93 (s, 6H), 3.85 3.64 (m, 6H), 3.64 3.45 (m, 2H), 3.05 (s, 3H); 450 [M + H]⁺ | 45 | 1.93 (B) |
| 59 | (3-methoxy-4-((4-(methylamino)-3-(trifluoromethyl)-1H-pyrrolo[2,3-b]pyridin-6-yl)amino)phenyl)(4-morpholino-piperidin-1-yl)methanone | ¹H NMR (400 MHz, TFA salt, Methanol-$d_4$) δ 7.55 7.46 (m, 2H), 7.23 (d, J = 1.4 Hz, 1H), 7.13 (dd, J = 8.0, 1.5 Hz, 1H), 5.94 (s, 1H), 4.17 4.00 (m, 2H), 3.93 (s, 3H), 3.87 3.75 (m, 2H), 3.63 3.44 (m, 4H), 3.30 3.15 (m, 4H), 3.04 (s, 4H), 3.02 2.85 (m, 1H), 2.36 2.13 (m, 2H), 1.85 1.70 (m, 2H); 533 [M + H]⁺ | 48 | 1.710 (B) |
| 60 | (2-fluoro-5-methoxy-4-((4-(methylamino)-3-(trifluoromethyl)-1H-pyrrolo[2,3-b]pyridin-6-yl)amino)phenyl)(4-methylpiperazin-1-yl)methanone | ¹H NMR (400 MHz, TFA salt, Methanol-$d_4$) δ 7.70 (t, J = 9.5 Hz, 2H), 7.51 (s, 2H), 7.15 (d, J = 5.9 Hz, 2H), 6.06 (s, 1H), 3.93 (s, 3H), 3.70 3.45 (m, 4H), 3.28 3.15 (m, 4H), 3.06 (s, 3H), 2.98 (s, 3H); 481 [M + H]⁺ | 50 | 1.71 (B) |
| 61 | (3-methoxy-4-((4-(methylamino)-3-(trifluoromethyl)-1H-pyrrolo[2,3-b]pyridin-6-yl)amino)phenyl)(4-(4-methylpiperazin-1-yl)piperidin-1-yl)methanone | ¹H NMR (400 MHz, TFA salt, Methanol-$d_4$) δ 7.52 7.47 (m, 2H), 7.22 (d, J = 1.2 Hz, 1H), 7.12 (dd, J = 8.0, 1.4 Hz, 1H), 5.94 (s, 1H), 4.82 4.65 (m, 1H), 4.05 3.95 (m, 1H), 3.92 (s, 3H), 3.50 3.42 (m, 4H), 3.25 3.11 (m, 4H), 3.05 3.02 2.93 (m, 1H) 2.92 (s, 3H), 2.20 1.95 (m, 2H), 1.75 1.62 (m, 2H); 546 [M + H]⁺ | 56 | 1.63 (B) |
| 62 | $N^6$-(2-methoxy-4-(4-methylpiperazin-1-yl)phenyl)-$N^4$-methyl-3- | ¹H NMR (400 MHz, TFA salt, Methanol-$d_4$) δ 7.42 (d, J = 1.2 Hz, 1H), 7.25 (d, J = 8.6 Hz, 1H), 6.81 (d, J = | 57 | 1.740 (B) |

TABLE 4-continued

| Example | Name | ¹H NMR; MS(ESI) m/z | Yield (%) | HPLC r.t. (min) (method) |
|---|---|---|---|---|
| | (trifluoromethyl)-1H-pyrrolo[2,3-b]pyridine-4,6-diamine | 2.4 Hz, 1H), 6.70 (dd, J = 8.6, 2.5 Hz, 1H), 5.73 (s, 1H), 3.95 (m, 2H), 3.86 (s, 3H), 3.64 (m, 2H), 3.54 3.47 (m, 1H), 3.43 3.38 (m, 1H), 3.28 (m, 2H), 3.19 3.05 (m, 2H), 3.00 (s, 3H), 2.99 (s, 3H); 435 [M + H]⁺ | | |
| 63 | (3-methoxy-4-((4-(methylamino)-3-(trifluoromethyl)-1H-pyrrolo[2,3-b]pyridin-6-yl)amino)phenyl)(4-methylpiperazin-1-yl)methanone | ¹H NMR (400 MHz, TFA salt, Methanol-d₄) δ 7.53 (d, J = 8.0 Hz, 1H), 7.51 7.49 (m, 1H), 7.28 (d, J = 1.5 Hz, 1H), 7.17 (dd, J = 8.0, 1.6 Hz, 1H), 5.96 (s, 1H), 3.94 (s, 3H), 3.75 3.40 (m, 4H), 3.40 3.11 (m, 4H), 3.05 (s, 3H), 2.97 (s, 3H); 463 [M + H]⁺ | 27 | 1.670 (B) |
| 64 | (3-methoxy-4-((4-((2-methoxyethyl)amino)-3-(trifluoromethyl)-1H-pyrrolo[2,3-b]pyridine-6yl)amino)phenyl)(morpholino)methanone | ¹H NMR (400 MHz, TFA salt, Methanol-d₄) δ 7.51 7.47 (m, 2H), 7.23 (d, J = 1.2 Hz, 1H), 7.11 (dd, J = 8.0, 1.4 Hz, 1H), 5.99 (s, 1H), 3.92 (s, 3H), 3.83 3.76 (m, 4H), 3.68 (t, J = 5.0 Hz, 2H), 3.63 3.47 (m, 4H), 3.52 (t, J = 5.1 Hz, 2H), 3.42 (s, 3H); 494 [M + H]⁺ | 42 | 2.03 (B) |
| 65 | (3-methoxy-4-((4-((2-methoxyethyl)amino)-3-(trifluoromethyl)-1H-pyrrolo[2,3-b]pyridin-6-yl)amino)phenyl)(4-morpholino-piperidin-1-yl)methanone | ¹H NMR (400 MHz, TFA salt, Methanol-d₄) δ 7.55 7.48 (m, 2H), 7.22 (d, J = 1.4 Hz, 1H), 7.12 (dd, J = 8.0, 1.6 Hz, 1H), 6.00 (s, 1H), 4.15 4.00 (m, 5H), 3.92 (s, 3H), 3.87 3.75 (m, 4H), 3.68 (t, J = 5.2 Hz, 2H), 3.60 3.52 (m, 2H), 3.68 (t, J = 5.2 Hz, 2H), 3.42 (s, 3H), 3.27 3.15 (m, 4H), 3.02 2.85 (m, 1H), 2.35 2.10 (m, 2H), 1.85 1.70 (m, 2H)); 577 [M + H]⁺ | 64 | 1.81 (B) |
| 66 | (3-methoxy-4-((4-((2-methoxyethyl)amino)-3-(trifluoromethyl)-1H-pyrrolo[2,3-b]pyridin-6-yl)amino)phenyl)(4-methylpiperazin-1-yl)-methanone | ¹H NMR (400 MHz, TFA salt, Methanol-d₄) δ 7.58 (t, J = 7.9 Hz, 1H), 7.51 (d, J = 1.1 Hz, 1H), 7.27 (d, J = 1.6 Hz, 1H), 7.16 (dd, J = 8.0, 1.7 Hz, 1H), 6.01 (s, 1H), 4.38 (m, 1H), 3.94 (s, 3H), 3.68 (t, J = 5.2 Hz, 2H), 3.60 (m, 4H), 3.52 (t, J = 5.2 Hz, 2H), 3.48 (m, 4H), 3.42 (s, 3H), 3.35 (m, 2H), 3.25 (m, 2H), 2.96 (s, 3H); 507 [M + H]⁺ | 57 | 1.76 (B) |
| 67 | (3-methoxy-4-((4-((2-methoxyethyl)amino)-3-(trifluoromethyl)-1H-pyrrolo[2,3-b]pyridin-6-yl)amino)phenyl)(4-methylpiperazin-1-yl)piperidin-1-yl)methanone | ¹H NMR (400 MHz, TFA salt, Methanol-d₄) δ 7.54 7.48 (m, 2H), 7.22 (d, J = 1.3 Hz, 1H), 7.11 (dd, J = 8.0, 1.6 Hz, 1H), 6.00 (s, 1H), 4.70 (br s, 1H), 3.92 (s, 3H), 3.69 (t, J = 5.2 Hz, 2H), 3.52 (t, J = 5.2 Hz, 2H), 3.43 (s, 3H), 3.41 3.32 (m, 4H), 3.27 3.12 (m, 4H), 3.11 2.95 (m, 4H), 2.90 (s, 3H), 2.00 (m, 2H), 1.63 (m, 2H); 590 [M + H]⁺ | 8 | 4.399 |
| 68 | N⁶-(2-methoxy-4-(4-methylpiperazin-1-yl)phenyl)-N⁴-(2-methoxyethyl)-3-(trifluoromethyl)-1H-pyrrolo[2,3-b]pyridine-4,6-diamine | ¹H NMR (400 MHz, TFA salt, Methanol-d₄) δ 7.44 (d, J = 1.1 Hz, 1H), 7.26 (d, J = 8.6 Hz, 1H), 6.81 (d, J = 2.2 Hz, 1H), 6.70 (dd, J = 8.6, 2.4 Hz, 1H), 5.77 (s, 1H), 4.02 3.87 (m, 2H), 3.86 (s, 3H), 3.67 (t, J = 5.1 Hz, 2H), 3.65 3.55 (m, 1H), 3.52 3.48 (m, 1H), 3.46 (t, J = 5.1 Hz, 2H), 3.44 3.38 (m, 5H), 3.22 3.05 (m, 2H), 2.99 (s, 3H); 479 [M + H]⁺ | 56 | 4.686 |
| 69 | N⁶-(5-chloro-1-((3S,4S)-3-fluoro-1-(oxetan-3-yl)piperidin-4-yl)-1H-pyrazol-4-yl)-N⁴-ethyl-3-(trifluoromethyl)-1H-pyrrolo[2,3-b]pyridine-4,6-diamine | ¹H NMR (400 MHz, TFA salt, Methanol-d₄) δ 7.84 (s, 1H), 7.51 (s, 1H), 5.74 (s, 1H), 5.11-5.27 (m, 1H), 4.88 (m, 5H), 4.28 (m, 1H), 3.76 (m, 1H), 3.43 (m, 3H), 3.00 (m, 1H), 2.92 (m, 1H), 2.55 (m, 1H), 2.39 (m, 1H), 1.34 (t, J = 6.9 Hz, 3H); 502 [M + H]⁺ | 82 | 4.877 |
| 70 | (4-(ethylamino)-3-(trifluoromethyl)-1H-pyrrolo[2,3-b]pyridin-6-yl)amino)-3-methoxyphenyl)(4-(4-methylpiperazin-1-yl)piperidin-1-yl)methanone | 560 [M + H]⁺ | 14 | 4.501 |
| 71 | 4-((4-(ethylamino)-3-(trifluoromethyl)-1H-pyrrolo[2,3-b]pyridin-6-yl)amino)-2-fluoro-5methoxy-N-(1-(oxetanepiperidin-4-yl)benzamide | ¹H NMR (400 MHz, TFA salt, Methanol-d₄) δ 7.67 (d, J = 12.0 Hz, 1H), 7.54 (s, 1H), 7.41 (d, J = 6.5 Hz, 1H), 6.01 (s, 1H), 4.88 (m, 2H), 4.45 (br s, 1H), 4.24 (br s, 1H), 3.96 (s, 3H), 3.58 (br s, 2H), 3.46 (q, J = 7.2 Hz, 2H), 3.08 (br s, 2H), 2.33 (m, 2H), 2.05 (br s, 2H), 1.37 (t, J = 7.2 Hz, 3H); 551 [M + H]⁺ | 68 | 4.991 |
| 72 | 4-((4-(ethylamino)-3-(trifluoromethyl)-1H-pyrrolo[2,3-b]pyridin-6-yl)amino)-2-fluoro-5-methoxy-N-(1-methylpiperidin-4-yl)benzylamide | ¹H NMR (400 MHz, TFA salt, DMSO-d₆) δ 11.90 (s, 1H), 9.49 (d, J = 71.8 Hz, 1H), 8.75 8.65 (m, 1H), 8.34 (s, 1H), 8.17 7.95 (m, 1H), 7.57 (br s, 1H), 7.16 (dd, J = 12.6, 6.9 Hz, 1H), 6.38 (s, 1H), 4.82 (br s, 1H), 3.91 (s, 3H), 3.52 3.42 (m, 2H), 3.32 3.23 (m, 2H), 3.16 3.02 | 59 | 4.994 |

TABLE 4-continued

| Example | Name | ¹H NMR; MS(ESI) m/z | Yield (%) | HPLC r.t. (min) (method) |
|---|---|---|---|---|
| 73 | 2-fluoro-5-methoxy-4-((4-((2-methoxyethyl)amino)-3-(trifluoromethyl)-1H-pyrrolo[2,3-b]pyridin-6-yl)amino)(1-methylpiperidin-4-yl)benzamide | ¹H NMR (400 MHz, TFA salt, DMSO-d₆) δ 11.93 (d, J = 2.3 Hz, 1H), 9.52 (d, J = 70.3 Hz, 1H), 8.77 8.67 (m, 1H), 8.36 8.29 (m, 1H), 8.09 7.98 (m, 2H), 7.59 (s, 1H), 7.15 (dd, J = 12.8, 6.9 Hz, 1H), 6.41 (s, 1H), 5.09 (br s, 1H), 4.20 3.94 (m, 2H), 3.91 (d, J = 3.3 Hz, 3H), 3.61 (t, J = 5.3 Hz, 2H), 3.40 3.36 (m, 2H), 3.32 (s, 3H), 3.21 3.03 (m, 2H), 2.80 2.75 (m, 3H), 2.08 2.00 (m, 2H), 1.81 1.67 (m, 2H); 539 [M + H]⁺ | 50 | 4.910 |
| 74 | 4-((4-(ethylamino-3-(trifluoromethyl)-1H-pyrrolo[2,3-b]pyridin-6-yl)amino)-2-fluoro-N-(1-isopropylpiperidin-4-yl)-5-methoxybenzamide | ¹H NMR (400 MHz, TFA salt, DMSO-d₆) δ 11.91 11.87 (m, 1H), 9.07 (d, J = 42.5 Hz, 1H), 8.77 8.67 (m, 1H), 8.34 (s, 1H), 8.22 8.00 (m, 1H), 7.57 (s, 1H), 7.15 7.10 (m, 1H), 6.38 (s, 1H), 4.81 (br s, 1H), 4.11 3.98 (m, 1H), 3.91 (s, 3H), 3.51 3.45 (m, 1H), 3.45 3.36 (m, 2H), 3.32 3.25 (m, 2H), 3.17 3.05 (m, 2H), 2.15 2.05 (m, 2H), 1.85 1.73 (m, 2H), 1.33 1.17 (m, 9H); 537 [M + H]⁺ | 49 | 5.085 |
| 75 | (R)-(2,4-dimethylpiperazin-1-yl)(2-fluoro-5-methoxy-4-((4-(methylamino)-3-(trifluoromethyl)-1H-pyrrolo[2,3-b]pyridin-6-yl)amino)phenyl)methanone | ¹H NMR (400 MHz, TFA salt, DMSO) δ 11.86 (s, 1H), 9.60 (br s, 1H), 8.76 (br s, 1H), 8.33 (s, 1H), 7.55 (s, 1H), 6.92 (br s, 1H), 6.31 (s, 1H), 5.12 (br s, 1H), 4.96 (br s, 1H), 4.18-4.11 (m, 1H), 3.90 (s, 3H), 3.22-3.17 (m, 2H), 3.16-2.92 (m, 2H), 2.89 (s, 3H), 2.84 (s, 3H), 1.47-1.23 (m, 3H); 495 [M + H]⁺ | 47 | 1.762 (B) |
| 76 | (3-methoxy-4-((4-morpholino-3-(trifluoromethyl)-1H-pyrrolo[2,3-b]pyridin-6-yl)amino)phenyl)(morpholino)methanone | ¹H NMR (400 MHz, TFA salt, DMSO) δ 8.24 (d, J = 8.16 Hz, 1H), 7.55 (s, 1H), 7.16 (s, 1H), 7.29 (d, J = 6.48 Hz, 1H), 3.97 (s, 3H), 3.89 (m, 4H), 3.73 (brs, 8H), 3.20 (m, 4H); 506 [M + H]⁺ | 60 | 6.108 |
| 77 | N-(5-chloro-1-((3S,4S)-3-fluoro-1-(oxetane-3-yl)piperidin-4-yl)-1H-pyrazol-4-yl)-4-morpholino-3-(trifluoromethyl)-1H-pyrrolo[2,3-b]pyridine-6-amine | ¹H NMR (400 MHz, TFA salt, DMSO) δ 8.02 (s, 1H), 7.54 (s, 1H), 6.23 (s, 1H), 5.29-5.12 (m, 1H), 4.89-4.86 (m, 2H), 4.86-4.81 (m, 2H), 4.34-4.29 (m, 1H), 3.88-3.86 (m, 4H), 3.79-3.72 (m, 1H), 3.48-3.33 (m, 2H), 3.22-3.20 (m, 4H), 3.09-2.94 (m, 2H), 2.49-2.37 (m, 2H); 544 [M + H]⁺ | 44 | 5.121 |
| 78 | N6-(5-chloro-1-((3S,4S)-3-fluoro-1-(oxetan-3-yl)piperidin-4-yl)-1H-pyrazol-4-yl)-N4-methyl-3-(trifluoromethyl)-1H-pyrrolo[2,3-b]pyridine-4,6-diamine | ¹H NMR (400 MHz, TFA salt, DMSO) δ 7.86 (s, 1H), 7.50 (s, 1H), 5.73 (s, 1H), 5.27-5.10 (m, 1H), 4.75-4.83 (m, 2H), 4.81-4.77 (m, 2H), 4.22-4.19 (m, 2H), 3.71-3.65 (m, 1H), 3.39-3.33 (m, 1H), 3.04 (s, 3H), 2.95-2.79 (m, 2H) 2.54-2.33 (m, 2H); 488 [M + H]⁺ | 48 | 4.593 |
| 79 | N6-(5-chloro-1-((3S,4S)-3-fluoro-1-(oxetan-3-yl)piperidin-4-yl)-1H-pyrazol-4-yl)-3-methoxyethyl-3-(trifluoromethyl)-1H-pyrrolo[2,3-b]pyridine-4,6-diamine | ¹H NMR (400 MHz, TFA salt, DMSO) δ 7.86 (s, 1H), 7.51 (s, 1H), 5.80 (s, 1H), 5.29-5.17 (m, 1H), 4.89-4.86 (m, 2H), 4.85-4.81 (m, 2H), 4.35-4.32 (m, 1H), 3.82-3.75 (m, 1H), 3.70-3.67 (m, 1H), 3.53-3.50 (m, 4H), 3.43 (s, 3H), 3.13-2.97 (m, 2H), 2.55-2.39 (m, 2H); 532 [M + H]⁺ | 48 | 4.777 |
| 80 | 1-(6-((4-(ethylamino)-3-(trifluoromethyl)-1H-pyrrolo[2,3-b]pyridin-6-yl)amino)-7-methoxy-3,4-dihydroisoquinolin-2(1H)-yl)-2,2,2-trifluoroethan-1-one | ¹H NMR (400 MHz, TFA salt, DMSO) δ 7.51 (s, 1H), 7.28 (s, 1H), 7.09 (s, 1H), 5.90 (s, 1H), 4.90 (s, 2H), 3.96 (t, J = 5.6 Hz, 2H), 3.91 (s, 3H), 3.15 (q, J = 7.12 Hz, 2H), 3.01-3.00 (m, 2H), 1.38 (t, J = 7.16 Hz, 3H); 502 [M + H]⁺ | 88 | 5.920 |
| 81 | N4-ethyl-N6-(7-methoxy-1,2,3,4-tetrahydro-isoquinolin-6-yl)-3-(trifluoromethyl)-1H-pyrrolo[2,3-b]pyridine-4,6-diamine | ¹H NMR (400 MHz, TFA salt, DMSO) δ 7.50 (s, 1H), 7.37 (s, 1H), 7.03 (s, 1H), 5.87 (s, 1H), 4.42 (s, 2H), 3.89 (s, 3H), 3.53 (t, J = 6.32 Hz, 2H), 3.39 (q, J = 7.14 Hz, 2H), 3.10 (t, J = 6.16 Hz, 2H), 1.34 (t, J = 7.16 Hz, 2H); 406 [M + H]⁺ | 41 | 4.632 |
| 82 | (3-methoxy-4-((4-morpholino-3-(trifluoromethyl)-1H-pyrrolo[2,3-b]pyridin-6-yl)amino)phenyl)(4-methylpiperazin-1-yl)methanone | ¹H NMR (400 MHz, TFA salt, MeOD-d₄) δ 8.50 (d, J = 8.24 Hz, 1H), 7.55 (s, 1H), 7.18 (s, 1H), 7.14 (d, J = 8.24 Hz, 1H), 6.57 (s, 1H), 4.49 (brs, 2H), 4.00 (s, 3H), 4.00-3.88 (m, 4H), 3.57 (brs, 2H), 3.49 (brs, 2H), 3.22 (brs, 2H), 3.19-3.15 (m, 4H), 2.99 (s, 3H); 519 [M + H]⁺ | 43 | 5.080 |
| 83 | (3-methoxy-4-((4-morpholino-3-(trifluoromethyl)-1H-pyrrolo[2,3-b]pyridin-6-yl)amino)phenyl)(4-(4-methylpiperazin-1-yl)piperidin-1-yl)methanone | ¹H NMR (400 MHz, TFA salt, MeOD-d₄) δ 8.30 (d, J = 8.2 Hz, 1H), 7.55 (s, 1H), 7.14 (s, 1H), 7.08 (d, J = 8.2 Hz, 1H), 6.52 (s, 1H), 3.97 (s, 3H), 3.90-3.88 (m, 4H), 3.45-3.33 (m, 7H), 3.21-3.14 (m, 4H), 3.13-3.10 (m, 3H), 2.93 (s, 3H), 2.17-1, 99 (m, | 49 | 4.795 |

| Example | Name | ¹H NMR; MS(ESI) m/z | Yield (%) | HPLC r.t. (min) (method) |
|---|---|---|---|---|
| 84 | (3-methoxy-4-(3-(trifluoromethyl)-4-(3-(trifluoromethyl)phenylamino)-1H-pyrrolo[2,3-b]pyridin-6-ylamino)phenyl)(morpholino)methanone | 2H), 1.70-1.61 (m, 2H); 602 M + H]⁺<br>¹H NMR (400 MHz, TFA salt, DMSO) δ 7.71-7.59 (m, 6H), 7.17 (s, 1H), 7.05 (d, J = 7.92 Hz, 1H), 6.17 (s, 1H), 3.90 (s, 3H), 3.72 (br, 8H); 579 [M + H]⁺ | 36 | 6.647 |
| 85 | (3-methoxy-4-(3-(trifluoromethyl)-4-(3-(trifluoromethyl)phenylamino)-1H-pyrrolo[2,3-b]pyridin-6-ylamino)phenyl)(4-morpholino-piperidin-1-yl)methanone | ¹H NMR (400 MHz, TFA salt, DMSO) δ 8.11-8.09 (m, 2H), 7.79-7.76 (m, 2H), 7.68-7.57 (m, 2H), 7.15 (s, 1H), 7.06 (d, J = 9.8 Hz, 1H), 6.28 (s, 1H), 4.10 (br, 2H), 3.92 (s, 3H), 3.82 (br, 2H), 3.56-3.53 (m, 3H), 3.25 (br, 2H), 3.10 (br, 4H), 2.24 (br, 2H), 1.79-1.74 (m, 2H); 662 [M + H]⁺ | 47 | 5.540 |
| 86 | N6-(5-chloro-1-((3S,4S)-3-fluoro-1-(oxetan-3-yl)piperidin-4-yl)-1H-pyrazol-4-yl)-3-(trifluoromethyl)-N4-(3-(trifluoromethyl)phenyl)-1H-pyrrolo[2,3-b]pyridine-4,6-diamine | ¹H NMR (400 MHz, TFA salt, DMSO) δ 7.81 (s, 1H), 7.68-7.60 (m, 5H), 5.93 (s, 1H), 5.20-5.02 (m, 1H), 4.89-4.83 (m, 2H), 4.79-4.74 (m, 2H), 4.20-4.15 (m, 1H), 3.66-3.60 (m, 1H), 3.33-3.32 (m, 1H), 2.85-2.68 (m, 2H), 2.45-2.22 (m, 2H); 618 [M + H]⁺ | 39 | 5.789 |
| 87 | (3-methoxy-4-((4-methoxyethyl)(methyl)amino)-3-(trifluoromethyl)-1H-pyrrolo[2,3-b]pyridin-6-yl)amino)phenyl)(morpholino)methanone | ¹H NMR (400 MHz, TFA salt, MeOD) δ 7.66 (d, J = 8.0 Hz, 1H), 7.59 (s, 1H), 7.23 (s, 1H), 7.14 (d, J = 8.0 Hz, 1H), 6.28 (s, 1H), 3.95 (s, 3H), 3.88-3.52 (m, 12H), 3.28 (s, 3H), 3.12 (s, 3H); 508 [M + H]⁺ | 64 | 5.670 |
| 88 | (3-methoxy-4-((4-methoxyethyl)(methyl)amino)-3-(trifluoromethyl)-1H-pyrrolo[2,3-b]pyridin-6-yl)amino)phenyl)((4-morpholino-piperidin-1-yl)methanone | ¹H NMR (400 MHz, TFA salt, MeOD) δ 7.78 (d, J = 8.1 Hz, 1H), 7.58 (s, 1H), 7.22 (s, 1H), 7.14 (d, J = 8.1 Hz, 1H), 6.32 (s, 1H), 4.20-4.02 (m, 2H), 3.96 (s, 3H), 3.89-3.70 (m, 2H), 3.65 (s, 4H), 3.61-3.50 (m, 2H), 3.25-3.15 (m, 5H), 3.10 (s, 3H), 2.40-2.15 (m, 2H), 1.81-1.69 (m, 2H); 590 [M + H]⁺ | 45 | 4.484 |
| 89 | N6-(5-chloro-1-((3S,4S)-3-fluoro-1-(oxetan-3-yl)piperidin-4-yl)-1H-pyrazol-4-yl)methoxyethyl)-N4-methyl-3-(trifluoromethyl)-1H-pyrrolo[2,3-b]pyridine-4,6-diamine | ¹H NMR (400 MHz, TFA salt, DMSO) δ 7.88 (s, 1H), 7.58 (s, 1H), 6.04 (s, 1H), 5.27-5.10 (m, 1H), 4.86 (m, 2H), 4.381-4.78 (m, 2H), 4.26-4.21 (m, 1H), 3.68-3.67 (m, 3H), 3.65-3.64 (m, 2H), 3.42-3.35 (m, 1H), 3.27 (s, 3H), 3.12 (s, 3H), 2.96-2.83 (m, 2H), 2.54-2.33 (m, 2H); 546 [M + H]⁺ | 54 | 4.959 |
| 90 | (4-(4-(isopropylamino)-3-(trifluoromethyl)-1H-pyrrolo[2,3-b]pyridin-6-ylamino)-3-methoxyphenyl)(4-morpholino-piperidin-1-yl)methanone | ¹H NMR (400 MHz, TFA salt, MeOD-d₄) δ 7.54-7.52 (m, 2H), 7.23 (s, 1H), 7.14 (d, J = 8.04 Hz, 1H), 5.98 (s, 1H), 4.09-3.98 (m, 3H), 3.93 (s, 3H), 3.89-3.84 (m, 3H), 3.55-3.40 (m, 4H), 3.33-3.13 (m, 4H), 2.24-2.15 (m, 2H), 1.77-1.74 (m, 2H), 1.35 (d, J = 6.28 Hz, 6H); 561 [M + H]⁺ | 13 | 4.845 |
| 91 | (R)-(4-((4-((1-hydroxy-3-methylbutan-2-yl)amino)-3-(trifluoromethyl)-1H-pyrrolo[2,3-b]amino)-3-methoxyphenyl)(4-morpholino-piperidin-1-yl)methanone | ¹H NMR (400 MHz, TFA salt, MeOD) δ 7.41 (s, 1H), 7.37 (d, J = 8.0 Hz, 1H), 7.11 (s, 1H), 7.02 (d, J = 8.0 Hz, 1H), 5.93 (s, 1H), 4.05-3.91 (m, 3H), 3.81 (s, 3H), 3.75-3.60 (m, 4H), 3.50-3.46 (m, 4H), 3.23-2.70 (m, 5H), 2.24-1.96 (m, 3H), 1.73-1.59 (m, 2H), 0.97-0.90 (m, 7H); 605 [M + H]⁺ | 37 | 4.724 |
| 92 | (R)-(4-((4-((1-hydroxy-3-methylbutan-2-yl)amino)-3-(trifluoromethyl)-1H-pyrrolo[2,3-b]amino)-3-methoxyphenyl)(morpholino)methanone | ¹H NMR (400 MHz, TFA salt, MeOD) δ 7.42 (s, 1H), 7.39 (d, J = 8.0 Hz, 1H), 7.14 (s, 1H), 7.04 (d, J = 8.0 Hz, 1H), 5.95 (s, 1H), 3.83 (s, 3H), 3.70-3.40 (m, 9H), 2.06-1.99 (m, 1H), 0.96 (t, J = 7.2 Hz, 6H); 522 [M + H]⁺ | 54 | 5.316 |
| 93 | (S)-(4-((4-(2-butylamino)-3-(trifluoromethyl)-1H-pyrrolo[2,3-b]pyridin-6-yl)amino)-3-methoxyphenyl)(4-morpholino-piperidin-1-yl)-methanone | ¹H NMR (400 MHz, TFA salt, MeOD) δ 7.41 (s, 1H), 7.40 (d, J = 8.0 Hz, 1H), 7.12 (s, 1H), 6.75 (d, J = 8.0 Hz, 1H), 5.86 (s, 1H), 4.08-3.96 (m, 2H), 3.82 (s, 3H), 3.79-3.51 (m, 3H), 3,49-3.35 (m, 3H), 3.29-3.04 (m, 4H), 2.25-2.04 (m, 2H), 1.84-1.63 (m, 4H), 1.27-1.18 (m, 4H), 0.96-0.84 (m, 4H); 575 [M + H]⁺ | 45 | 5.034 |
| 94 | (4-((4-(cyclopropylamino)-3-(trifluoromethyl)-1-((2-(trimethylsilyl)ethoxy)methyl)-1H-pyrrolo[2,3-b]pyridin-6-yl)3-methoxyphenyl)(4-morpholino-piperidine-1-yl)methanone | ¹H NMR (400 MHz, TFA salt, MeOD-d₄) δ 7.62 (d, J = 8.18 Hz, 1H), 7.50 (s, 1H), 7.24 (s, 1H), 7.15 (d, J = 7.72 Hz, 1H), 6.42 (s, 1H), 4.10-3.99 (m, 2H), 3.98-3.94 (m, 1H), 3.94 (s, 3H), 3.93-3.79 (m, 2H), 3. 72-3.49 (m, 3H), 3.34-3.13 (m, 5H), 2.70-2.65 (m, 1H), 2.40-2.14 (m, 2H), 1.85-1.60 (m, 2H), 1.00-0.94 (m, 2H), 0.76-0.68 (m, 2H); 559 [M + H]⁺ | 33 | 4.712 |
| 95 | (4-((4-(cyclopropyl-amino)-3-(trifluoromethyl)-1H-pyrrolo[2,3-b]pyridin-6- | ¹H NMR (400 MHz, TFA salt, MeOD) δ 7.61 (J = 8.0 Hz, 1H), 7.49 (s, 1H), 7.23 (s, 1H), 7.14 (J = 8.0 Hz, 1H), 6.41 (s, 1H), 3.94 (s, 1H), | 16 | 5.431 |

TABLE 4-continued

| Example | Name | ¹H NMR; MS(ESI) m/z | Yield (%) | HPLC r.t. (min) (method) |
|---|---|---|---|---|
|  | yl)amino)-3-methoxyphenyl)(morpholino)methanone | 3.86-3.45 (m, 8H), 2.72-2.66 (m, 1H), 0.98-0.90 (m, 2H), 0.85-0.50 (m, 2H); 476 [M + H]⁺ |  |  |
| 96 | 5-((4-(ethylamino)-3-(trifluoromethyl)-1H-pyrrolo[2,3-b]pyridin-6-yl)amino)-6-methoxy-2-methylisoindolin-1-one | ¹H NMR (400 MHz, TFA salt, DMSO) δ 11.88 (br s, 1H), 8.67 (br s, 1H), 8.33 (br s, 1H), 7.56 (br s, 1H), 7.20 (s, 1H), 6.27 (s, 1H), 4.93 (br s, 1H), 4.35 (s, 2H), 3.94 (s, 3H), 3.32-3.26 (m, 2H), 3.05 (s, 3H), 1.23 (t, J = 7.1 Hz, 3H); 420 [M + H]⁺ | 42 | 2.05 (B) |
| 97 | 7-((4-(ethylamino)-3-(trifluoromethyl)-1H-pyrrolo[2,3-b]pyridin-6-yl)amino)-6-methoxy-2,2,4-trimethyl-2H-benzo[1,4]oxazin-3(4H)-1-one | ¹H NMR (400 MHz, TFA salt, MeOD-d₄) δ 7.46 (d, J = 1.16 Hz, 1H), 7.00 (s, 1H), 6.90 (s, 1H), 5.81 (s, 1H), 3.98 (s, 3H), 3.40 (s, 3H), 3.89-3.35 (m, 2H), 1.47 (s, 6H), 1.34-1.30 (m, 3H); 464 [M + H]⁺ | 57 | 5.77 |
| 98 | 6-((4-(ethylamino)-3-(trifluoromethyl)-1H-pyrrolo[2,3-b]pyridin-6-yl)amino)-5-methoxy-2-methylisoindolin-1-one | ¹H NMR (400 MHz, TFA salt, MeOD-d₄) δ 7.75 (s, 1H), 7.48 (d, J = 1.32 Hz, 1H), 7.40 (s, 1H), 5.92 (s, 1H), 4.54 (s, 2H), 3.98 (s, 3H), 3.44-3.39 (m, 2H), 3.20 (s, 3H), 1.35-1.31 (m, 3H); 420 [M + H]⁺ | 8 | 5.19 |
| 99 | 4-(ethylamino)-6-((6-methoxy-2-methyl-3-oxoisoindol-5-yl)amino)-1H-pyrrolo[2,3-b]pyridine-3-carbonitrile | ¹H NMR (400 MHz, TFA salt, MeOD-d₄) δ 7.84 (s, 1H), 7.68 (s, 1H), 7.38 (s, 1H), 5.92 (s, 1H), 4.53 (s, 2H), 3.98 (s, 3H), 3.42-3.39 (m, 2H), 3.20 (s, 3H), 1.37-1.33 (m, 3H); 377 [M + H]⁺ | 3 | 4.76 |
| 100 | 6-((2 (2-cyanopropan-2-yl)-4-methylthiazol-5-yl)amino)-4-(ethylamino)-1H-pyrrolo[2,3-b]pyridine-3-carbonitrile | ¹H NMR (400 MHz, Methanol-d₄) δ 7.45 (s, 1H), 5.86 (s, 1H), 3.24-3.20 (m, 2H), 2.29 (s, 3H), 1.73 (s, 6H), 1.25 (t, J = 7.2 Hz, 3H); 366 [M + H]⁺ | 60 | 5.25 |
| 101 | (6-chloro-5-((4-(ethylamino)-3-(trifluoromethyl)-1H-pyrrolo[2,3-b]pyridin-6-yl)amino)-2-methylisoindolin-1-one | ¹H NMR (400 MHz, TFA salt, DMSO) δ 11.90 (br s, 1H), 8.61 (s, 1H), 8.30 (br s, 1H), 7.65 (s, 1H), 7.57 (br s, 1H), 6.35 (s, 1H), 4.88 (br s, 1H), 4.39 (s, 2H), 3.30-3.28 (m, 2H), 3.04 (s, 3H), 1.24 (t, J = 7.1 Hz, 3H); 424 [M + H]⁺ | 8 | 2.07 |
| 102 | 5-((4-(ethylamino)-3-(trifluoromethyl)-1H-pyrrolo[2,3-b]pyridin-6-yl)amino)-2-methylisoindolin-1-one | ¹H NMR (400 MHz, TFA salt, DMSO) δ 11.86 (br s, 1H), 9.25 (br s, 1H), 8.10 (br s, 1H), 7.66-7.64 (m, 1H), 7.53-7.48 (m, 2H), 5.95 (s, 1H), 4.84 (br s, 1H), 4.39 (s, 2H), 3.29-3.24 (m, 2H), 3.03 (s, 3H), 1.25 (t, J = 7.1 Hz, 3H); 390 [M + H]⁺ | 22 | 1.99 (B) |
| 103 | 4-(ethylamino)-6-((2-methyl-1-oxoisoindol-5-yl)amino)-1H-pyrrolo[2,3-b]pyridine-3-carbonitrile | ¹H NMR (400 MHz, TFA salt, MeOD-d₄) δ 7.78 (d, J = 8.24 Hz, 1H), 7.72 (s, 1H), 7.68 (s, 1H), 7.49-7.47 (m, 1H), 6.01 (s, 1H), 4.51 (s, 2H), 3.45-3.40 (m, 2H), 3.20 (s, 3H), 1.38-1.34 (m, 3H); 347 [M + H]⁺ |  | 4.711 |
| 104 | 6-((6-chloro-2-methyl-1-oxoisoindolin-5-yl)amino)-4-(ethylamino)-1H-pyrrolo[2,3-b]pyridine-3-carbonitrile | ¹H NMR (400 MHz, TFA salt, CDCl₃-d₁) δ 8.11 (d, J = 1.52 Hz, 1H), 7.98 (s, 1H), 7.92 (s, 1H), 5.88 (b, 1H), 5.51 (s, 1H), 4.39 (s, 2H), 3.28-3.25 (m, 2H), 3.22 (s, 3H), 1.36-1.32 (m, 3H); 381 [M + H]⁺ |  | 5.058 |
| 105 | 4-(ethylamino)-6-((6-methoxy-2,2,4-trimethyl-3-oxo-3,4-dihydro-2H-benzo[b][1,4]oxazin-yl)amino)-1H-pyrrolo[2,3-b]pyridine-3-carbonitrile | ¹H NMR (400 MHz, Methanol-d₄) δ 8.08 (s, 1H), 7.44 (s, 1H), 6.64 (s, 1H), 5.87 (s, 1H), 3.83 (s, 3H), 3.27 (s, 3H), 3.27-3.21 (m, 2H), 3.21 (s, 3H), 1.33 (s, 6H), 1.24 (t, J = 7.1 Hz, 3H); 421 [M + H]⁺ | 63 | 5.16 |

<Experimental Example 1> Evaluation 1 of Enzyme Activity Inhibiting Effect of the Compound According to the Present Invention The following experiment was performed to evaluate inhibitory activity of the compound of the present invention against DYRK1A kinase.

Particularly, a substrate was added to a basic reaction buffer (20 mM Hepes (pH 7.5), 10 mM MgCl₂, 1 mM EGTA, 0.02% Brij35, 0.02 mg/ml BSA, 0.1 mM Na₃VO₄, 2 mM DTT, 1% DMSO), to which cofactors necessary for the reaction were added. Then, DYRK1A kinase was added thereto, followed by mixing well. Each compound of Examples was added thereto by using acoustic technology (Echo550; nanoliter range). The mixture was left at room temperature for 20 minutes and then ³³P-ATP (specific activity 10 mCi/ml) was added to initiate the reaction. After reacting at room temperature for 2 hours, spotting was performed on P81 exchange paper. Upon completion of the reaction, kinase activity was detected using a filter-binding method.

The inhibitory activity of the compounds of Examples 1, 2, 4, 5, 10, 23, 27, 53, 56, 57, 59, 60, 61, 63, 65 and 67 against DYRK1A was summarized in Table 5 below.

The calculated IC₅₀ values of kinase were sorted as follows and presented in Table 5 below:

TABLE 5

| Example | DYRK1A(μM) |
|---|---|
| 1 | C |
| 2 | A |
| 4 | C |
| 5 | B |
| 10 | A |
| 23 | C |

TABLE 5-continued

| Example | DYRK1A(μM) |
|---|---|
| 27 | C |
| 53 | B |
| 56 | A |
| 57 | A |
| 59 | A |
| 60 | B |
| 61 | A |
| 63 | A |
| 65 | A |
| 67 | A |

Grade A: less than 10 nM, Grade B: 10~100 nM, and Grade C: more than 100 nM.

As shown in Table 5, when the compounds of the present invention were treated, the concentration of DYRK1A was significantly reduced to 0.01 μM or less. Therefore, since the compounds of the present invention were excellent in inhibiting DYRK1A expression, they can be effectively used for the treatment or prevention of DYRK1A related disease.

<Experimental Example 2> Evaluation 2 of Enzyme Activity Inhibiting Effect of the Compound According to the Present Invention To evaluate inhibitory activity of the compounds of Examples 2, 54, 55, 69, 70, 71, 64, 66, 72, 73, 74, 75, 77, 78, 79, 87, 88, 89, 90, 91, 92, 93, 94 and 95 of the present invention against DYRK1A kinase, DYRK1A kinase binding assay was performed using LanthaSceen™ Eu as follows.

First, 10 concentrations (9 concentrations diluted serially by 3× and DMSO) of each compounds were diluted in 1× kinase buffer A (Invitrogen, PV6135) three times the final concentration. The diluted compounds were added to a 384-well white assay plate (Corning, 4513) (5 μl/well).

Then, LanthaScreen™ Eu-anti-GST Antibody (Invitrogen, PV5594) and DYRK1A (Invitrogen, PV3785) were diluted to make the final concentrations of 6 nM and 15 nM respectively in 1× kinase buffer A, resulting in the preparation of antibody/kinase mixed solution. This antibody/kinase mixed solution was added to the assay plate where the diluted compound was loaded at the concentration of 5 μl/well. At this time, the final concentrations of the antibody and the DYRK1A were 2 nM and 5 nM respectively.

Next, kinase tracer 236 solution (Invitrogen, PV5592) was diluted in 1× kinase buffer A to make the concentration of 45 nM. This diluted solution was added to the assay plate at the concentration of 5 μl/well. At this time, the final concentration of kinase tracer 236 was 15 nM and $K_d$ value of Kinase tracer 236 was determined through tracer titration assay.

Finally, after reacting at room temperature for 1 hour, fluorescence was measured (Excitation 340 nm, Kinase Tracer Emission 665 nm, LanthaScreen™ Eu-anti-GST Antibody Emission 620 nm) using Synergy neo (BioTek). Emission ratio (Kinase Tracer Emission Antibody Emission) was calculated based on the measured values, which was presented as a dose-response curve. Then, $IC_{50}$ was calculated.

$IC_{50}$ values of each compound of Examples 52, 54, 55, 69, 70, 71, 64, 66, 72, 73, 74, 75, 77, 78, 79, 87, 88, 89, 90, 91, 92, 93, 94 and 95 were summarized in Table 6 below.

The calculated $IC_{50}$ values of kinase were sorted as follows and presented in Table 6 below:

TABLE 6

| Example | $IC_{50}$(μM) |
|---|---|
| 2 | A |
| 54 | C |
| 55 | C |
| 69 | B |
| 70 | B |
| 71 | C |
| 64 | B |
| 66 | B |
| 72 | C |
| 73 | B |
| 74 | B |
| 75 | C |
| 77 | C |
| 78 | B |
| 79 | B |
| 87 | B |
| 88 | B |
| 89 | B |
| 90 | B |
| 91 | B |
| 92 | C |
| 93 | C |
| 94 | B |
| 95 | B |

Grade A: less than 10 nM, Grade B: 10~100 nM, and Grade C: more than 100 nM.

As shown in Table 6, $IC_{50}$ values of the compounds of the present invention for DYRK1A were 0.1 μM or less, indicating that the compounds of the present invention had excellent activity to inhibit DYRK1A expression.

Therefore, since the compounds of the present invention were excellent in inhibiting DYRK1A expression, they can be effectively used for the treatment or prevention of DYRK1A related disease.

<Experimental Example 3> Calcineurin/NFAT Signaling Inhibitory Activity of the Compound According to the Present Invention To investigate the intracellular DYRK1A inhibitory effect of the compounds according to the present invention, DYRK1A high dependent calcienurin/NFAT signaling experiment was performed.

NFATc transcription factors usually exist as phosphorylated proteins in the cytoplasm. At this time, as the $Ca^{2+}$ concentration increases, NFATc is dephosphorylated by $Ca^{2+}$ dependent protein phosphatase calcienurin, and NFATc moves into the nucleus.

NFATc in the nucleus can form a transcription complex with the partner protein NFATn and can bind to the target gene promoter to induce the expression of the target gene. At this time, DYRK1A reversely phosphorylates NFATc to inhibit migration of NFATc to the nucleus, resulting in suppression of the target gene expression.

Based on the facts above, the inhibitory effect of candidate compounds on DYRK1A was measured quantitatively using a luciferase reporter containing NFAT responsive element (NFAT-RE) in the promoter which is useful for measuring NFATc transcriptional activity.

Particularly, NFAT-RE-luciferase reporter and DYRK1A were overexpressed in 293T cells. 24 hours later, the cells were treated with IM and PMA (phorbol 12-myristate 13-acetate). 12 hours after the treatment of candidate compounds, luciferase activity was measured using One-Glo reagent (Promega).

FIG. 1a is a graph illustrating the luciferase activity of DYRK1A affected by the compounds of Examples 53, 54, 55, 56 and 57.

Figure 1B:
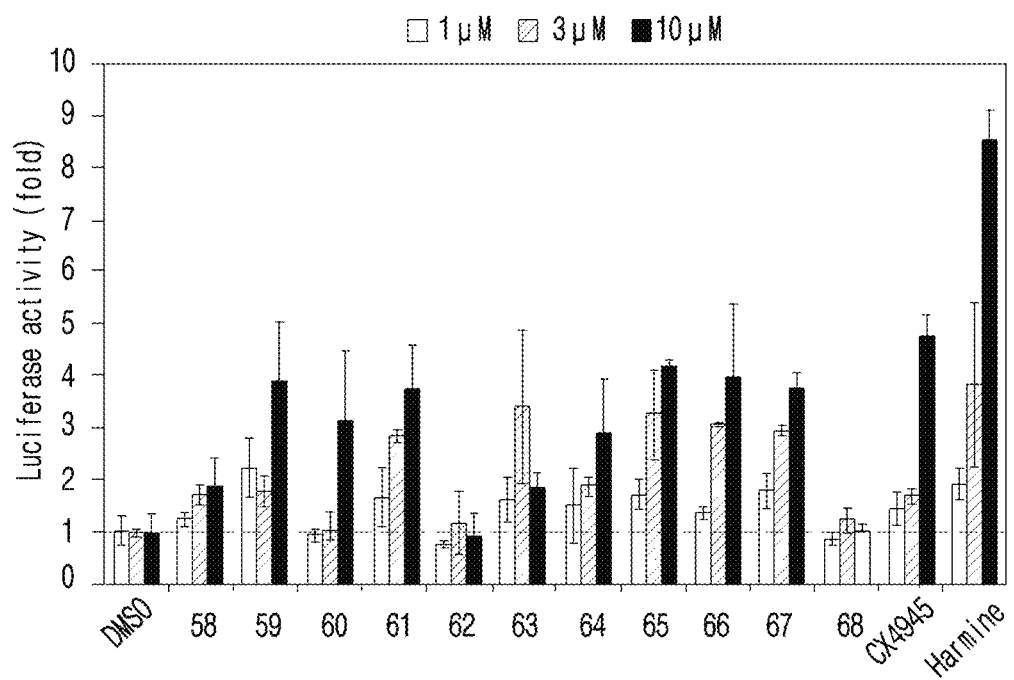
FIG. 1b is a graph illustrating the luciferase activity of DYRK1A affected by the compounds of Examples 58, 59, 60, 61, 62, 63, 64, 65, 66, 67 and 68.

FIG. 1b is a graph illustrating the luciferase activity of DYRK1A affected by the compounds of Examples 58, 59, 60, 61, 62, 63, 64, 65, 66, 67 and 68.

As shown in FIG. 1a and FIG. 1b, when the compounds of the present invention were treated, luciferase activity of DYRK1A was significantly increased, compared with when DMSO alone was treated. Therefore, it was confirmed that the compounds of the present invention were able to inhibit calcienurin/NFAT signaling efficiently, suggesting that they can be effectively used for the treatment or prevention of DYRK1A related disease.

<Experimental Example 4> Inhibitory Effect of the Compound According to the Present Invention on the Phosphorylation of Tau To investigate DYRK1A inhibitory activity of the compounds according to the present invention, phosphorylation of Tau, which is a representative substrate protein of DYRK1A and at the same time a key factor of Alzheimer's disease and Down syndrome, was confirmed through K1.

Tau is a microtubule related protein. DYRK1A phosphorylates mainly Thr212 of Tau protein, and this phosphorylation has been clearly observed in hippocampal tissue of Down syndrome mouse model showing overexpression of DYRK1A.

Particularly, 293T cells were cultured in a 6-well plate at the density of 5×10$^5$ cells for 12 hours, followed by co-transfection with 1 μg of each Tau and DYRK1A expressing DNA. After 24 hours of incubation, the compound of Example 53 was treated thereto at the concentrations of 0.001, 0.01, 0.1 and 1 μM, respectively, followed by culture for 6 hours. Then, the cells were recovered and disrupted to obtain a cell extract containing the total protein of 293T cells.

The total protein was developed on SDS-PAGE and transferred to a 0.45 μm polyvinylidene fluoride transfer membrane; (GE Healthcare, USA), followed by blocking with 5% skim milk. The primary antibodies, anti-Tau antibody (Thermo), anti-pTau (T212) antibody (Invitrogen) and anti-DYRK1A antibody (Santa Cruz) were diluted in tris buffered saline tween-20 (TBST) containing 5% skim milk at the ratio of 1:1000, and treated to the transfer membrane, followed by reaction for overnight.

Then, the membrane was washed with TBST 4 times for 10 minutes, followed by reaction with secondary antibodies. Upon completion of the reaction, the membrane was washed with TBST 4 times for 10 minutes. The phosphorylation level of the protein on the transfer membrane was detected using WEST-ZOL plus western blotting detection system (iNtRON Biotechnology, USA) and LAS-4000 image analyzer (Fuji Film, Japan).

As for the control, the same experiment was performed using other DYRK1A inhibitors harmine and CX-4945. As a control for comparing the expression level, the expressions of hnRNPA1 and GAPDH were confirmed by the same manner as described above using anti-hnRNP A1 antibody (Gideon Dreyfuss, University of Pennsylvania, USA) and anti-GAPDH antibody as the primary antibodies.

Figure 2A:
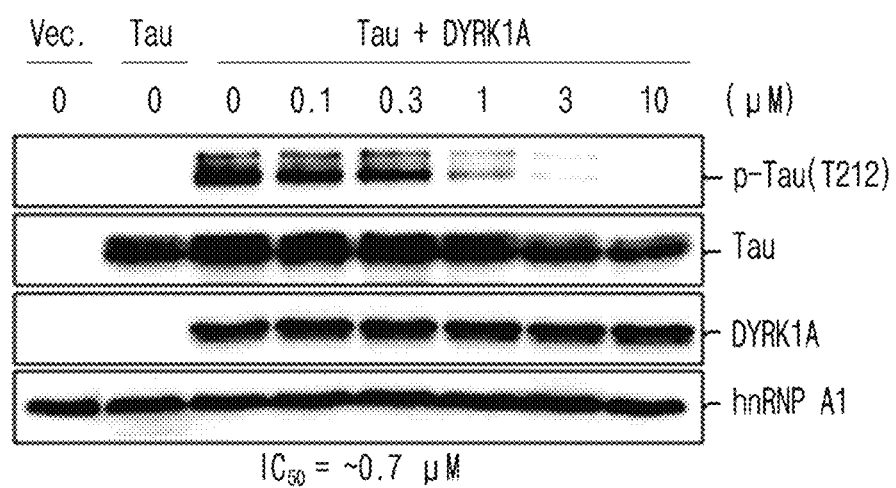
FIG. 2a is a photograph illustrating the results of Tau, hnRNPA1 and GAPDH inhibition experiments for each concentration of the compound of Example 57 in cells.

FIG. 2a is a photograph illustrating the results of Tau, hnRNPA1 and GAPDH inhibition experiments for each concentration of the compound of Example 57 in cells.

Figure 2B:
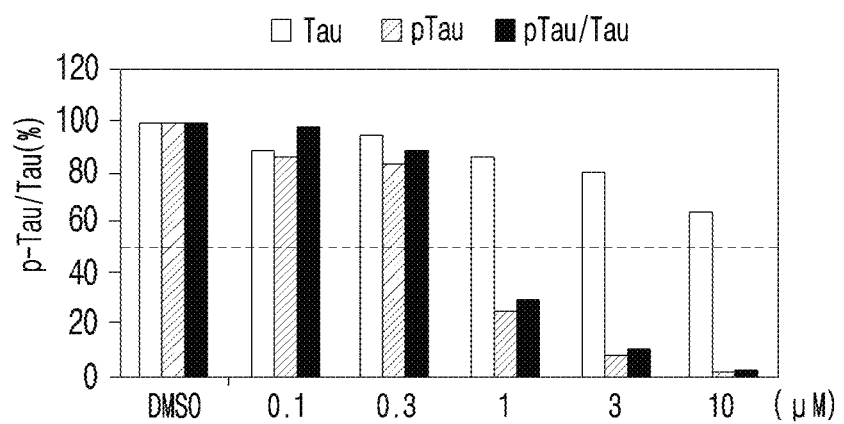
FIG. 2b is a graph illustrating the Tau inhibition rate at each concentration of the compound of Example 57 in cells.

FIG. 2b is a graph illustrating the Tau inhibition rate at each concentration of the compound of Example 57 in cells.

As shown in FIG. 2a and FIG. 2b, when the compound of the present invention was treated to the cells, Tau phosphorylation was efficiently inhibited. Therefore, it was confirmed that the compound of the present invention was able to inhibit Tau phosphorylation efficiently, suggesting that it can be effectively used for the treatment or prevention of DYRK1A related disease.

<Experimental Example 5> Evaluation of DYRK1A Inhibitory Effect of the Compound According to the Present Invention In Vivo 1. Observation of Embryos of Neurodevelopmental Disorder *Drosophila* Model To investigate DYRK1A inhibitory effect of the compound of the present invention in vivo, embryonic nervous system structure analysis was performed using a *Drosophila melanogaster* model over-expressing minibrain gene. Minibrain is a homologous gene of DYRK1A. Mutant *Drosophilas* lacking the minibrain gene are known to exhibit neurodevelopmental disorder, resulting in a smaller brain phenotype.

To confirm DYRK1A inhibitory effect of the compound of the present invention using the *Drosophila* in vivo model, minibrain (mnb) gene, the *Drosophila* homologous gene of DYRK1A, was first cloned, and then tissue specific over-expression was induced using UAS/Gal4 system.

Particularly, Drosophilas transformed with UAS-Minibrain expression vector were prepared through P-element-mediated germ line transformation. These transformed Drosophilas were used to perform mating with various tissue specific promoter lines.

First, minibrain was over-expressed in the nervous system using the *Drosophila* nervous system-specific elav-Gal4 promoter line by using UAS/Gal4 system. F1 generation embryos within 24 hours prior to waking into 1$^{st}$ instar larvae were collected and fixed with 4% formalin. Then, synaptobrevin-GFP, a fluorescent protein that can confirm the structure of the nervous system, was co-expressed and observed with a fluorescence confocal microscope to analyze the structure and morphology of the nervous system.

Figure 3A:
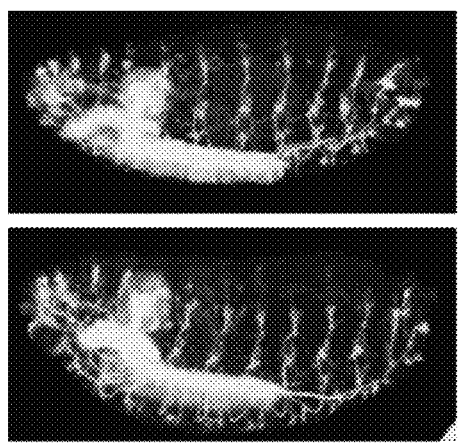
FIG. 3a is a fluorescent confocal photomicrograph of the wild type Drosophila embryo.
Figure 3B:
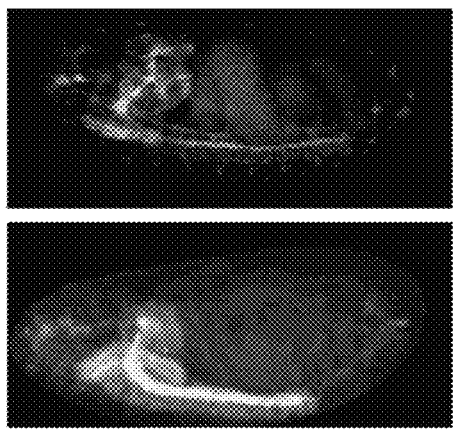
FIG. 3b is a fluorescent confocal photomicrograph of the Drosophila embryo with minibrain overexpressing neurodevelopmental abnormality.
Figure 3C:
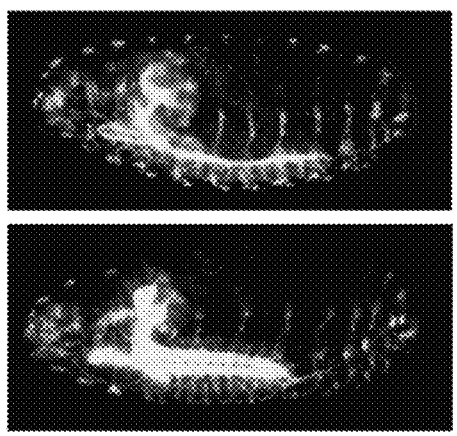
FIG. 3c is a fluorescent confocal photomicrograph of the Drosophila embryo with minibrain overexpressing neurodevelopmental abnormality which was born by the parents that had been treated with the compound of Example 57 for 7 days before mating.

FIG. 3a is a fluorescent confocal photomicrograph of the wild type *Drosophila* embryo, FIG. 3b is a fluorescent confocal photomicrograph of the *Drosophila* embryo with minibrain overexpressing neurodevelopmental abnormality, and FIG. 3c is a fluorescent confocal photomicrograph of the *Drosophila* embryo with minibrain overexpressing neurodevelopmental abnormality which was born by the parents that had been treated with the compound of Example 57 for 7 days before mating.

Compared with the normal wild type *Drosophila* embryo shown in FIG. 3a, dysgenesis of the central and peripheral nervous system was caused by the overexpression of minibrain, as confirmed in FIG. 3b.

On the other hand, compared with the *Drosophila* embryo shown in FIG. 3b, when the compound of the present invention was co-treated, dysgenesis of the peripheral nervous system was significantly reduced, as confirmed in FIG. 3c.

Therefore, it was confirmed that the compound according to the present invention had an excellent inhibitory effect on DYRK1A in vivo. Thus, the compound of the present invention can be effectively used for the prevention or treatment of DYRK1A related disease.

2. Observation of *Drosophila* Wings Showing Vein Developmental Abnormality

To confirm the DYRK1A inhibitory effect of the compound according to the present invention in vivo, wings of the *Drosophila* model over-expressing minibrain gene specifically in wings were observed.

First, in order to produce *Drosophila* over-expressing minibrain specifically in wings, the UAS-Minibrain transformed *Drosophila* was mated with the wing specific promoter MS1096-Gal4 transformed *Drosophila*, resulting in the production of F1 generation.

Next, the effect of improving wing defects was confirmed to verify the DYRK1A inhibitory effect of the compound according to the present invention using the *Drosophila* DYRK1A/minibrain inhibitor discovery model. A medium supplemented with the compound at the concentration of 10 µM was prepared, in which embryos of *Drosophila* over-expressing minibrain specifically in wings were raised, followed by investigation of wing phenotype.

Figure 4A:
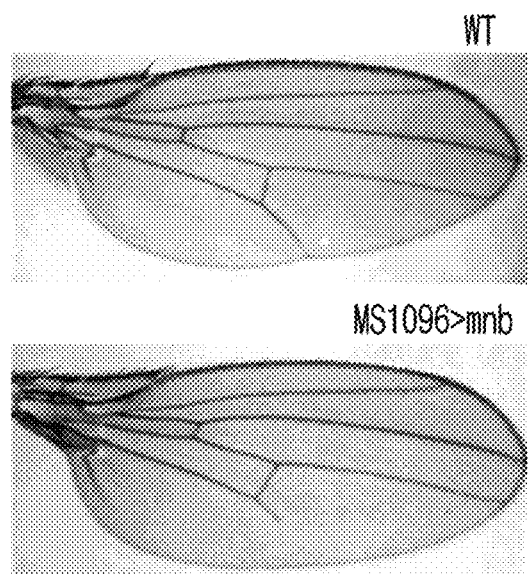
FIG. 4a is a photograph of wings of the control group and the Drosophila over-expressing minibrain specifically in the wings.
Figure 4B:
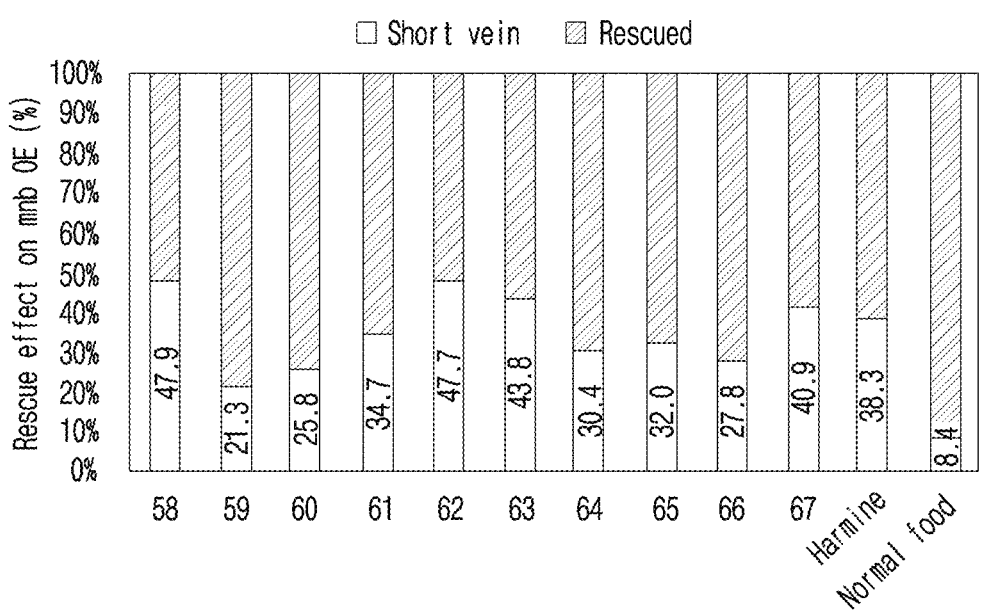
FIG. 4b is a graph illustrating the inhibitory effect of the compounds of Examples 58, 59, 60, 61, 62, 63, 64, 65, 66 and 67 of the present invention on the wing vein developmental abnormality.

FIG. 4a is a photograph of wings of the control group and the *Drosophila* over-expressing minibrain specifically in the wings, and FIG. 4b is a graph illustrating the inhibitory effect of the compounds of Examples 58, 59, 60, 61, 62, 63, 64, 65, 66 and 67 of the present invention on the wing vein developmental abnormality.

As shown in FIG. 4a, at least 90% of F1 generation (MS1096>2xmnb) displayed developmental abnormality in L5 vein (short wing vein phenotype).

As shown in FIG. 4b, it was confirmed that the compounds according to the present invention showed excellent inhibitory effect on the wing vein developmental abnormality. In particular, the compounds of Examples 58 (47.9%), 62 (47.7%) and 63 (43.8%) were confirmed to inhibit the wing vein developmental abnormality significantly.

3. Observation of Mouse Pancreatic β-Cell Proliferation

It is known that when human β-cells are treated with harmine that inhibits DYRK1A, the proliferation of β-cells is promoted by increasing the transcription factor activity by inhibiting the phosphorylation of NFAT known as a phosphorylation substrate of DYRK1A. In order to confirm the DYRK1A inhibitory effect of the compound of the present invention in vivo, an experiment was performed to examine the mouse pancreatic β-cell cell proliferation.

Particularly, pancreatic Langerhans islet tissues were extracted from the mouse at 8 weeks old, followed by culture in RPMI1640 medium supplemented with 10% FCS (fetal calves serum), 5.5 mM glucose and 1% penicillin-streptomycin for 24 hours.

Next, in order to separate β-cells as single cells from the Langerhans islet, cells were washed twice with PBS, followed by centrifugation. The collected cells were left in the medium supplemented with 1 mg/ml of trypsin for 10 minutes at 37° C. The cells were shaken using a pipette every 10 seconds for 5 minutes. Trypsin reaction was terminated by adding RPMI1640 containing 10% FCS (fetal calves serum), 5.5 mM glucose and 1% penicillin-streptomycin, followed by centrifugation to collect single cells.

Then, the single cells were loaded on the laminin-coated cover glass and stabilized for 24 hours. The cells were cultured in the medium containing the compound of the present invention for 72 hours. Immunofluorescence staining was performed using Ki-67 antibody which is useful for confirming cell division and insulin antibody which is useful for confirming β-cells. The cells double-stained with Ki-67/insulin were counted under Olympus F-1000 confocal fluorescence microscope to investigate cell proliferation.

Figure 5A:
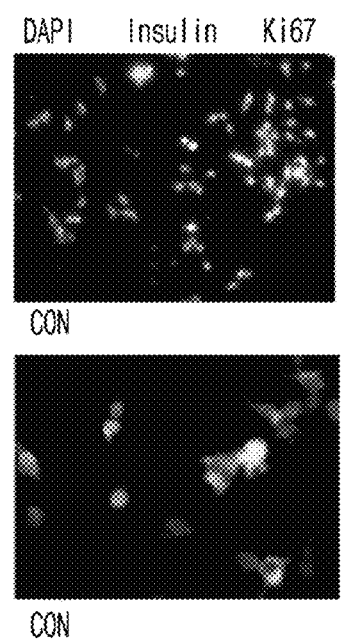
FIG. 5a is an immunofluorescent staining confocal fluorescence photomicrograph of the control group.
Figure 5B:
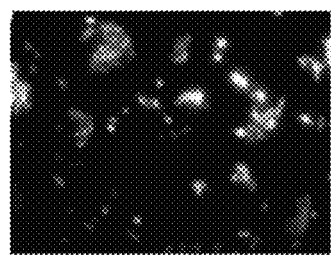
FIG. 5b is an immunofluorescent staining confocal fluorescence photomicrograph of the mouse treated with harmine.
Figure 5B:
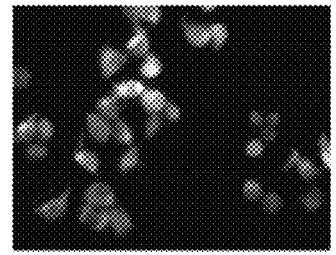
Figure 5C:
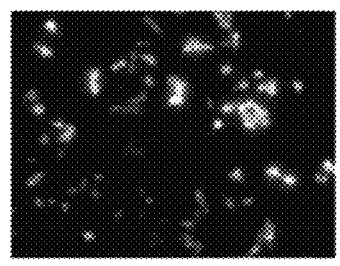
FIG. 5c is an immunofluorescent staining confocal fluorescence photomicrograph of the mouse treated with the compound of Example 57.
Figure 5C:
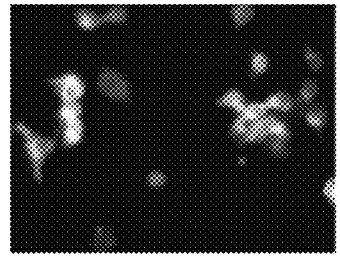
Figure 5D:
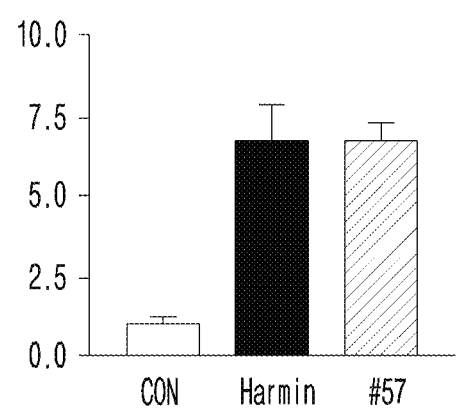
FIG. 5d is a graph illustrating the cell number of each mouse model.
Figure 6A:
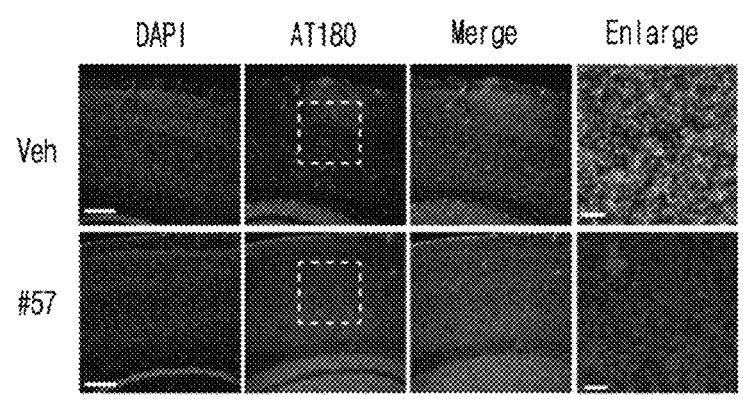
FIG. 6a: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), AT180: image obtained by immunohistochemistry using AT180 antibody, Merge: image obtained by overlapping DAPI and AT180 images, Enlarge: image obtained by enlarging AT180 image)
Figure 6B:
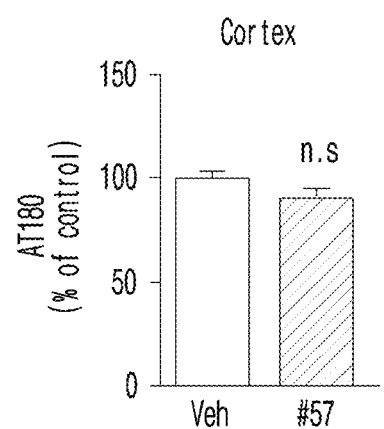
FIG. 6b: graph illustrating the immunoreactivity of AT180 in the cerebral cortex of the Alzheimer's disease animal model treated with vehicle (untreated group) or the compound of Example 57.
Figure 6C:
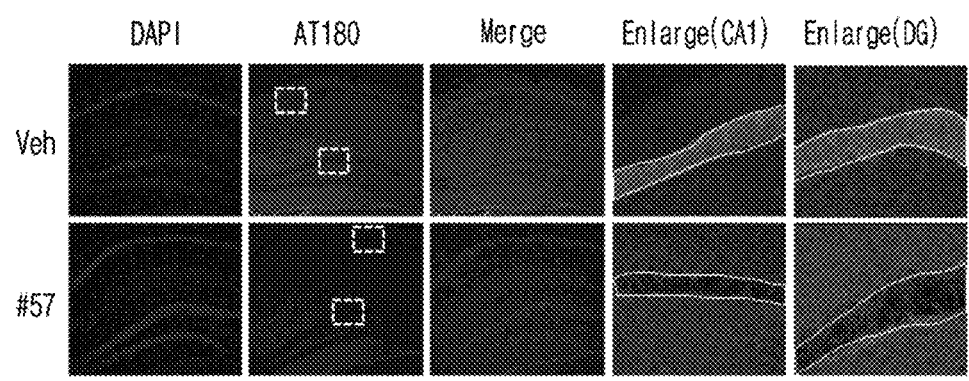
FIG. 6c: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), AT180: image obtained by immunohistochemistry using AT180 antibody, Enlarge (CA1): enlarged image of CA1 (cornus aminus, the region where the hippocampus begins and long-term memory is formed) of the hippocampus of AT180 image, Enlarge (DG): enlarged image of DG (dentate gyrus, the region where the hippocampus ends and new memory is formed) of the hippocampus of AT180 image, FIG. 6d: graph illustrating the immunoreactivity of AT180 in the CA1 (cornus aminus) of the Alzheimer's disease animal model treated with vehicle (untreated group) or the compound of Example 57, FIG. 6e: graph illustrating the immunoreactivity of AT180 in the DG (dentate gyrus) of the Alzheimer's disease animal model treated with vehicle (untreated group) or the compound of Example 57
Figure 6D:
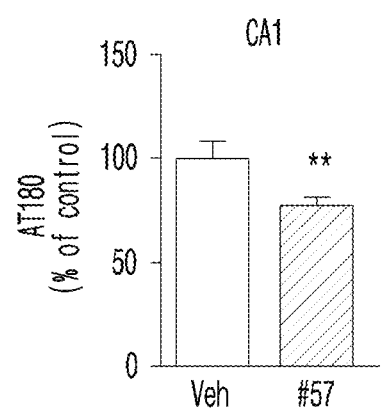
FIG. 6 presents the results of the evaluation of Tau phosphorylation inhibitory activity of the compound in the Alzheimer's disease animal model.
Figure 6E:
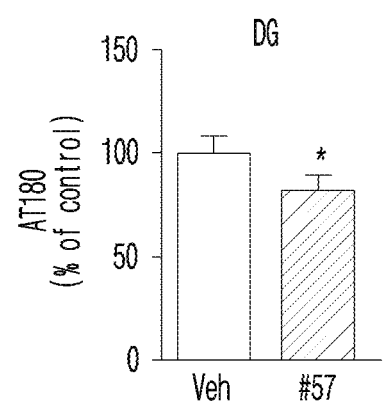
Figure 7A:
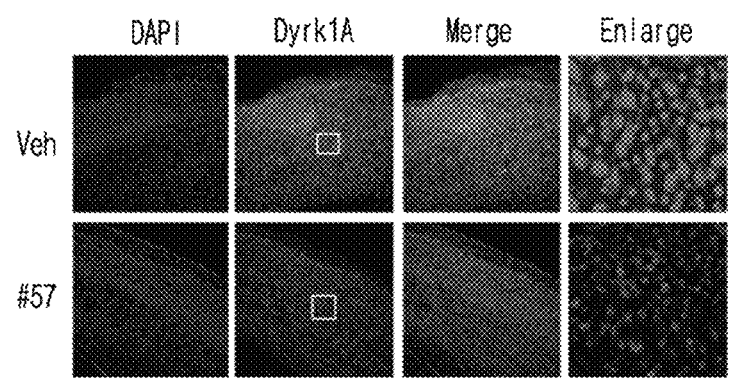
FIG. 7a: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), DYRK1A: image obtained by immunohistochemistry using DYRK1A protein, Merge: image obtained by overlapping DAPI and DYRK1A images, Enlarge: image obtained by enlarging DYRK1A image)
Figure 7B:
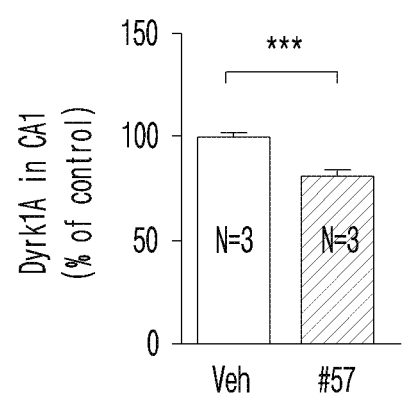
FIG. 7b: graph illustrating the immunoreactivity of DYRK1A in the cerebral cortex of the Alzheimer's disease animal model treated with vehicle (untreated group) or the compound of Example 57.
Figure 7C:
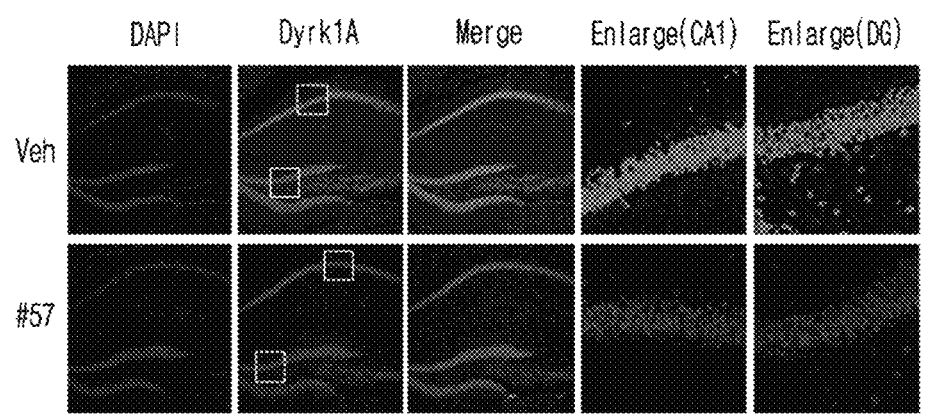
FIG. 7c: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), DYRK1A: image obtained by immunohistochemistry using DYRK1A protein, Enlarge (CA1): enlarged image of CA1 (cornus aminus, the region where the hippocampus begins and long-term memory is formed) of the hippocampus of DYRK1A image, Enlarge (DG): enlarged image of DG (dentate gyrus, the region where the hippocampus ends and new memory is formed) of the hippocampus of DYRK1A image, FIG. 7d: graph illustrating the immunoreactivity of DYRK1A in the CA1 (cornus aminus) of the Alzheimer's disease animal model treated with vehicle (untreated group) or the compound of Example 57, FIG. 7e: graph illustrating the immunoreactivity of DYRK1A in the DG (dentate gyrus) of the Alzheimer's disease animal model treated with vehicle (untreated group) or the compound of Example 57
Figure 7D:
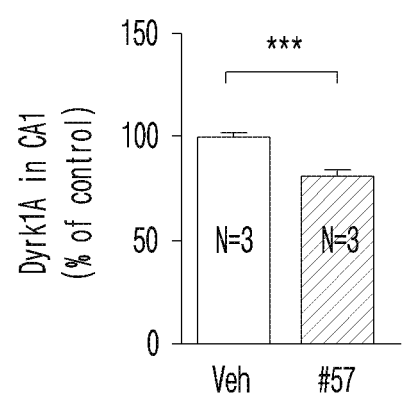
FIG. 7 presents the changes of DYRK1A protein by the compound of the present invention in the Alzheimer's disease animal model.
Figure 7E:
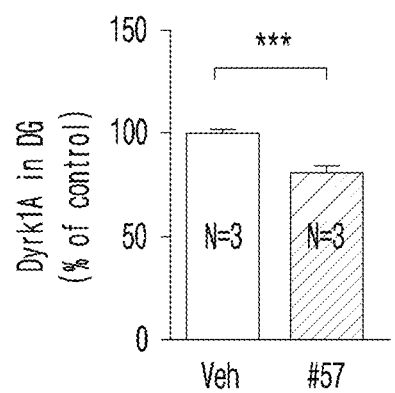
Figure 8A:
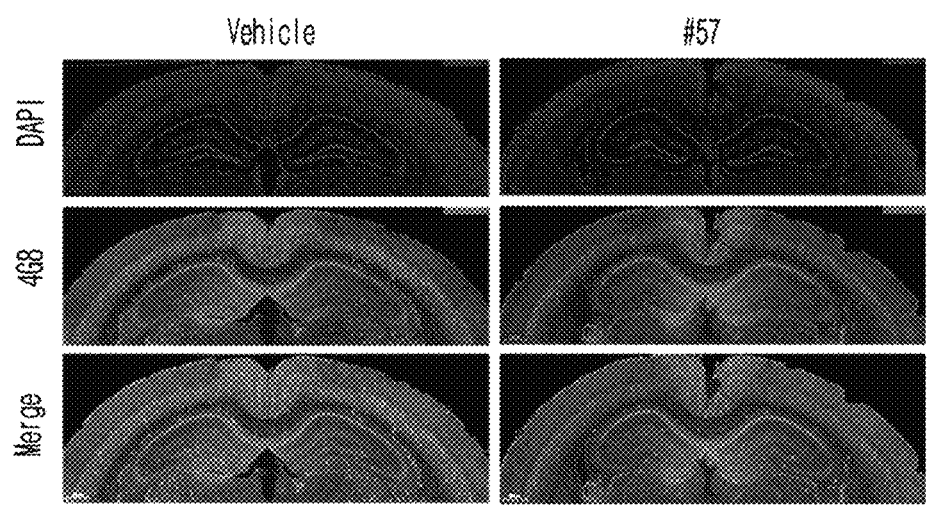
FIG. 8a: immunofluorescent staining confocal fluorescence photomicrograph of the cerebral cortex and the hippocampus of the Alzheimer's disease animal model treated with vehicle (untreated group) or the compound of Example 57 (DAPI: immunofluorescence image staining with DAPI (4',6-diamidino-2-phenylindol), 4G8: image obtained by immunohistochemistry using 4G8 antibody, Merge: image obtained by overlapping DAPI and 4G8 images)
Figure 8B:
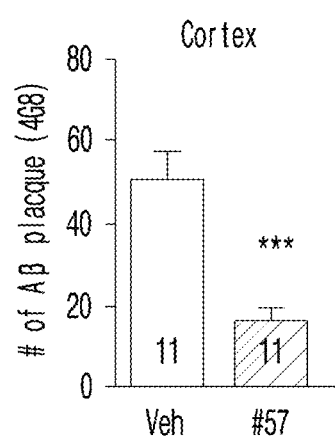
FIG. 8b: graph illustrating the changes in the number of amyloid plaque of 4G8 in the cerebral cortex of the Alzheimer's disease animal model treated with vehicle (untreated group) or the compound of Example 57.
Figure 8C:
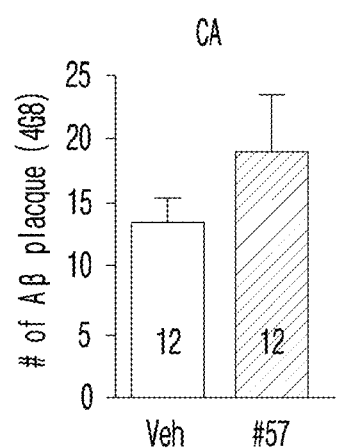
FIG. 8c: graph illustrating the changes in the number of amyloid plaque of 4G8 in the CA1 (cornus aminus) of the Alzheimer's disease animal model treated with vehicle (untreated group) or the compound of Example 57.
Figure 8D:
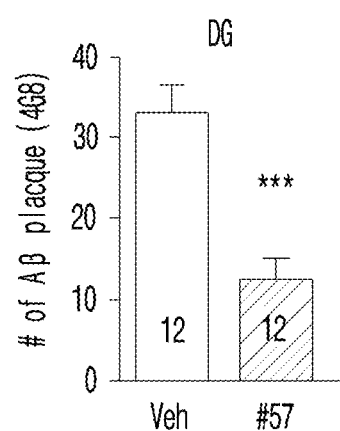
FIG. 8d: graph illustrating the changes in the number of amyloid plaque of 4G8 in the DG (dentate gyrus) of the Alzheimer's disease animal model treated with vehicle (untreated group) or the compound of Example 57

FIG. 5a is an immunofluorescent staining confocal fluorescence photomicrograph of the control group, FIG. 5b is an immunofluorescent staining confocal fluorescence photomicrograph of the mouse treated with harmine, FIG. 5c is an immunofluorescent staining confocal fluorescence photomicrograph of the mouse treated with the compound of Example 57, and FIG. 5d is a graph illustrating the cell number of each mouse model.

As shown in FIG. 5a and FIG. 5b, when harmine was treated, cell proliferation was active.

As shown in FIG. 5c, when the compound of Example 57 was treated, cell proliferation was also active.

Further, as shown in FIG. 5d, it was confirmed by quantitative measurement of cells that the treatment of the compound of Example 57 increased the cell number as much as 5 times.

It was confirmed by each in vivo experiment above that the compound of the present invention was able to inhibit the expression of DYRK1A efficiently. Therefore, since the compound of the present invention inhibited the expression of DYRK1A efficiently, it can be effectively used for the treatment and prevention of DYRK1A related disease.

<Experimental Example 6> Evaluation of Kinase Inhibitory Activity of the Compound According to the Present Invention The following experiment was performed to evaluate the activity of the compounds of the present invention to inhibit many enzymes.

Particularly, the compounds of Examples 18 and 57 were selected among all of those compounds of the present invention. DiscoverX Co. was asked to measure the enzyme (kinase) selectivity, and the experiment was performed using scanMAX™ Kinase assay panel.

At this time, the concentration of the drug treated to each enzyme was 1 uM in DMSO and the control percentage (% control) was determined by the following Equation 1. The results are shown in Table 7 below.

(Example Compound−Positive Control)/(Negative Control−Positive Control)×100    [Equation 1]

Herein, the positive control indicates the compound showing the % control of 0%, and the negative control indicates DMSO showing the % control of 100%. The enzyme selectivity in the present invention is defined as follows: When the % control for each enzyme is less than 35% (<35%), it is judged that the compound has the activity to the corresponding enzyme.

TABLE 7

|  | Example 18 | Example 57 |
|---|---|---|
| AAK1 | 69 | 54 |
| ABL1(E255K)-phosphorylated | 77 | 84 |
| ABL1(F317I)-nonphosphorylated | 89 | 96 |
| ABL1(F317I)-phosphorylated | 80 | 100 |
| ABL1(F317L)-nonphosphorylated | 95 | 86 |
| ABL1(F317L)-phosphorylated | 100 | 100 |
| ABL1(H396P)-nonphosphorylated | 89 | 68 |
| ABL1(H396P)-phosphorylated | 85 | 100 |
| ABL1(M351T)-phosphorylated | 100 | 98 |
| ABL1(Q252H)-nonphosphorylated | 95 | 54 |
| ABL1(Q252H)-phosphorylated | 100 | 100 |
| ABL1(T315I)-nonphosphorylated | 96 | 100 |
| ABL1(T315I)-phosphorylated | 100 | 96 |
| ABL1(Y253F)-phosphorylated | 89 | 100 |
| ABL1-nonphosphorylated | 97 | 51 |

TABLE 7-continued

|  | Example 18 | Example 57 |
|---|---|---|
| ABL1-phosphorylated | 87 | 61 |
| ABL2 | 93 | 98 |
| ACVR1 | 92 | 88 |
| ACVR1B | 88 | 82 |
| ACVR2A | 100 | 99 |
| ACVR2B | 100 | 98 |
| ACVRL1 | 80 | 89 |
| ADCK3 | 86 | 89 |
| ADCK4 | 100 | 75 |
| AKT1 | 100 | 97 |
| AKT2 | 87 | 90 |
| AKT3 | 96 | 96 |
| ALK | 2.7 | 2.5 |
| ALK(C1156Y) | 2.4 | 3.5 |
| ALK(L1196M) | 13 | 14 |
| AMPK-alpha1 | 92 | 75 |
| AMPK-alpha2 | 100 | 98 |
| ANKK1 | 78 | 100 |
| ARK5 | 94 | 94 |
| ASK1 | 79 | 77 |
| ASK2 | 82 | 92 |
| AURKA | 94 | 83 |
| AURKB | 73 | 81 |
| AURKC | 92 | 95 |
| AXL | 98 | 100 |
| BIKE | 90 | 85 |
| BLK | 99 | 73 |
| BMPR1A | 74 | 80 |
| BMPR1B | 85 | 100 |
| BMPR2 | 44 | 84 |
| BMX | 75 | 89 |
| BRAF | 83 | 98 |
| BRAF(V600E) | 87 | 94 |
| BRK | 95 | 94 |
| BRSK1 | 94 | 94 |
| BRSK2 | 96 | 79 |
| BTK | 99 | 100 |
| BUB1 | 76 | 99 |
| CAMK1 | 62 | 78 |
| CAMK1B | 34 | 81 |
| CAMK1D | 31 | 73 |
| CAMK1G | 71 | 63 |
| CAMK2A | 72 | 72 |
| CAMK2B | 73 | 80 |
| CAMK2D | 82 | 47 |
| CAMK2G | 77 | 72 |
| CAMK4 | 76 | 88 |
| CAMKK1 | 70 | 59 |
| CAMKK2 | 52 | 49 |
| CASK | 76 | 88 |
| CDC2L1 | 100 | 90 |
| CDC2L2 | 86 | 88 |
| CDC2L5 | 100 | 92 |
| CDK11 | 98 | 67 |
| CDK2 | 100 | 100 |
| CDK3 | 97 | 94 |
| CDK4 | 100 | 100 |
| CDK4-cyclinD1 | 100 | 95 |
| CDK4-cyclinD3 | 100 | 100 |
| CDK5 | 100 | 86 |
| CDK7 | 55 | 53 |
| CDK8 | 100 | 90 |
| CDK9 | 100 | 85 |
| CDKL1 | 89 | 63 |
| CDKL2 | 100 | 90 |
| CDKL3 | 100 | 61 |
| CDKL5 | 100 | 91 |
| CHEK1 | 100 | 91 |
| CHEK2 | 4.1 | 47 |
| CIT | 71 | 66 |
| CLK1 | 1.9 | 1.1 |
| CLK2 | 8.5 | 3.3 |
| CLK3 | 73 | 35 |
| CLK4 | 4 | 23 |
| CSF1R | 73 | 72 |
| CSF1R-autoinhibited | 51 | 83 |
| CSK | 93 | 76 |
| CSNK1A1 | 8.2 | 51 |
| CSNK1A1L | 3.1 | 71 |
| CSNK1D | 5.3 | 30 |
| CSNK1E | 0.6 | 51 |
| CSNK1G1 | 43 | 88 |
| CSNK1G2 | 27 | 86 |
| CSNK1G3 | 7.1 | 89 |
| CSNK2A1 | 83 | 100 |
| CSNK2A2 | 97 | 80 |
| CTK | 100 | 84 |
| DAPK1 | 16 | 70 |
| DAPK2 | 16 | 71 |
| DAPK3 | 14 | 86 |
| DCAMKL1 | 85 | 86 |
| DCAMKL2 | 77 | 79 |
| DCAMKL3 | 84 | 88 |
| DDR1 | 98 | 98 |
| DDR2 | 98 | 91 |
| DLK | 79 | 100 |
| DMPK | 81 | 100 |
| DMPK2 | 85 | 96 |
| DRAK1 | 56 | 67 |
| DRAK2 | 27 | 69 |
| DYRK1A | 2 | 0.4 |
| DYRK1B | 4 | 1.8 |
| DYRK2 | 14 | 27 |
| EGFR | 100 | 59 |
| EGFR(E746-A750del) | 83 | 98 |
| EGFR(G719C) | 95 | 91 |
| EGFR(G719S) | 80 | 92 |
| EGFR(L747-E749del, A750P) | 100 | 94 |
| EGFR(L747-S752del, P753S) | 92 | 97 |
| EGFR(L747-T751del, Sins) | 100 | 97 |
| EGFR(L858R) | 100 | 100 |
| EGFR(L858R, T790M) | 81 | 73 |
| EGFR(L861Q) | 85 | 94 |
| EGFR(S752-I759del) | 99 | 75 |
| EGFR(T790M) | 100 | 88 |
| EIF2AK1 | 92 | 99 |
| EPHA1 | 91 | 78 |
| EPHA2 | 97 | 83 |
| EPHA3 | 93 | 100 |
| EPHA4 | 98 | 94 |
| EPHA5 | 99 | 85 |
| EPHA6 | 98 | 87 |
| EPHA7 | 94 | 100 |
| EPHA8 | 85 | 100 |
| EPHB1 | 95 | 94 |
| EPHB2 | 87 | 100 |
| EPHB3 | 93 | 85 |
| EPHB4 | 100 | 88 |
| EPHB6 | 78 | 99 |
| ERBB2 | 99 | 73 |
| ERBB3 | 97 | 100 |
| ERBB4 | 85 | 82 |
| ERK1 | 100 | 98 |
| ERK2 | 94 | 74 |
| ERK3 | 85 | 94 |
| ERK4 | 98 | 93 |
| ERK5 | 20 | 50 |
| ERK8 | 99 | 93 |
| ERN1 | 24 | 61 |
| FAK | 78 | 77 |
| FER | 62 | 67 |
| FES | 89 | 87 |
| FGFR1 | 87 | 87 |
| FGFR2 | 85 | 72 |
| FGFR3 | 93 | 94 |
| FGFR3(G697C) | 88 | 78 |
| FGFR4 | 80 | 92 |
| FGR | 100 | 78 |
| FLT1 | 46 | 94 |
| FLT3 | 83 | 100 |
| FLT3(D835H) | 89 | 100 |
| FLT3(D835V) | 74 | 92 |
| FLT3(D835Y) | 82 | 88 |
| FLT3(ITD) | 92 | 79 |

TABLE 7-continued

| | Example 18 | Example 57 |
|---|---|---|
| FLT3(ITD, D835V) | 100 | 100 |
| FLT3(ITD, F691L) | 46 | 84 |
| FLT3(K663Q) | 84 | 94 |
| FLT3(N841I) | 89 | 85 |
| FLT3(R834Q) | 92 | 100 |
| FLT3-autoinhibited | 82 | 92 |
| FLT4 | 100 | 99 |
| FRK | 94 | 92 |
| FYN | 78 | 87 |
| GAK | 15 | 41 |
| GCN2(Kin.Dom.2, S808G) | 97 | 91 |
| GRK1 | 81 | 94 |
| GRK2 | 71 | 95 |
| GRK3 | 58 | 100 |
| GRK4 | 100 | 100 |
| GRK7 | 96 | 84 |
| GSK3A | 100 | 90 |
| GSK3B | 97 | 74 |
| HASPIN | 7.6 | 70 |
| HCK | 85 | 88 |
| HIPK1 | 63 | 54 |
| HIPK2 | 68 | 100 |
| HIPK3 | 74 | 71 |
| HIPK4 | 100 | 86 |
| HPK1 | 76 | 91 |
| HUNK | 57 | 51 |
| ICK | 84 | 100 |
| IGF1R | 74 | 71 |
| IKK-alpha | 44 | 100 |
| IKK-beta | 77 | 100 |
| IKK-epsilon | 96 | 96 |
| INSR | 36 | 48 |
| INSRR | 24 | 60 |
| IRAK1 | 79 | 100 |
| IRAK3 | 84 | 79 |
| IRAK4 | 99 | 100 |
| ITK | 87 | 97 |
| JAK1(JH1domain-catalytic) | 100 | 97 |
| JAK1(JH2domain-pseudokinase) | 82 | 45 |
| JAK2(JH1domain-catalytic) | 70 | 100 |
| JAK3(JH1domain-catalytic) | 54 | 100 |
| JNK1 | 0 | 40 |
| JNK2 | 0.1 | 52 |
| JNK3 | 0 | 52 |
| KIT | 49 | 91 |
| KIT(A829P) | 99 | 100 |
| KIT(D816H) | 80 | 96 |
| KIT(D816V) | 82 | 83 |
| KIT(L576P) | 77 | 100 |
| KIT(V559D) | 33 | 77 |
| KIT(V559D, T670I) | 48 | 78 |
| KIT(V559D, V654A) | 97 | 84 |
| KIT-autoinhibited | 66 | 100 |
| LATS1 | 97 | 94 |
| LATS2 | 26 | 100 |
| LCK | 96 | 90 |
| LIMK1 | 92 | 99 |
| LIMK2 | 90 | 99 |
| LKB1 | 62 | 92 |
| LOK | 91 | 84 |
| LRRK2 | 1.1 | 48 |
| LRRK2(G2019S) | 0.6 | 27 |
| LTK | 6.2 | 20 |
| LYN | 90 | 100 |
| LZK | 100 | 100 |
| MAK | 92 | 95 |
| MAP3K1 | 90 | 79 |
| MAP3K15 | 53 | 100 |
| MAP3K2 | 79 | 100 |
| MAP3K3 | 70 | 75 |
| MAP3K4 | 96 | 79 |
| MAP4K2 | 61 | 100 |
| MAP4K3 | 93 | 91 |
| MAP4K4 | 100 | 100 |
| MAP4K5 | 99 | 100 |
| MAPKAPK2 | 21 | 51 |
| MAPKAPK5 | 43 | 100 |
| MARK1 | 84 | 82 |
| MARK2 | 89 | 93 |
| MARK3 | 100 | 92 |
| MARK4 | 80 | 76 |
| MAST1 | 93 | 66 |
| MEK1 | 19 | 100 |
| MEK2 | 26 | 100 |
| MEK3 | 4.3 | 81 |
| MEK4 | 0 | 98 |
| MEK5 | 77 | 99 |
| MEK6 | 53 | 72 |
| MELK | 62 | 69 |
| MERTK | 100 | 91 |
| MET | 100 | 100 |
| MET(M1250T) | 100 | 100 |
| MET(Y1235D) | 100 | 85 |
| MINK | 55 | 100 |
| MKK7 | 89 | 93 |
| MKNK1 | 93 | 100 |
| MKNK2 | 60 | 95 |
| MLCK | 87 | 78 |
| MLK1 | 100 | 100 |
| MLK2 | 72 | 77 |
| MLK3 | 99 | 80 |
| MRCKA | 100 | 95 |
| MRCKB | 92 | 100 |
| MST1 | 99 | 76 |
| MST1R | 81 | 70 |
| MST2 | 95 | 100 |
| MST3 | 88 | 84 |
| MST4 | 81 | 100 |
| MTOR | 86 | 88 |
| MUSK | 97 | 100 |
| MYLK | 6 | 7.8 |
| MYLK2 | 72 | 85 |
| MYLK4 | 88 | 83 |
| MYO3A | 71 | 70 |
| MYO3B | 73 | 83 |
| NDR1 | 69 | 89 |
| NDR2 | 95 | 80 |
| NEK1 | 100 | 81 |
| NEK10 | 73 | 100 |
| NEK11 | 100 | 100 |
| NEK2 | 100 | 94 |
| NEK3 | 87 | 93 |
| NEK4 | 86 | 99 |
| NEK5 | 92 | 91 |
| NEK6 | 97 | 84 |
| NEK7 | 89 | 85 |
| NEK9 | 91 | 89 |
| NIK | 25 | 82 |
| NIM1 | 81 | 100 |
| NLK | 84 | 84 |
| OSR1 | 41 | 82 |
| p38-alpha | 100 | 83 |
| p38-beta | 77 | 76 |
| p38-delta | 99 | 85 |
| p38-gamma | 77 | 77 |
| PAK1 | 92 | 73 |
| PAK2 | 82 | 40 |
| PAK3 | 93 | 83 |
| PAK4 | 88 | 93 |
| PAK6 | 98 | 78 |
| PAK7 | 80 | 100 |
| PCTK1 | 98 | 83 |
| PCTK2 | 100 | 98 |
| PCTK3 | 86 | 86 |
| PDGFRA | 77 | 100 |
| PDGFRB | 76 | 92 |
| PDPK1 | 99 | 86 |
| PFCDPK1(P. falciparum) | 72 | 98 |
| PFPK5(P. falciparum) | 98 | 98 |
| PFTAIRE2 | 79 | 94 |
| PFTK1 | 89 | 95 |
| PHKG1 | 16 | 26 |
| PHKG2 | 12 | 23 |
| PIK3C2B | 100 | 78 |

TABLE 7-continued

| | Example 18 | Example 57 |
|---|---|---|
| PIK3C2G | 92 | 100 |
| PIK3CA | 100 | 87 |
| PIK3CA(C420R) | 87 | 100 |
| PIK3CA(E542K) | 96 | 100 |
| PIK3CA(E545A) | 100 | 77 |
| PIK3CA(E545K) | 92 | 73 |
| PIK3CA(H1047L) | 85 | 100 |
| PIK3CA(H1047Y) | 71 | 73 |
| PIK3CA(I800L) | 100 | 69 |
| PIK3CA(M1043I) | 100 | 99 |
| PIK3CA(Q546K) | 100 | 100 |
| PIK3CB | 89 | 100 |
| PIK3CD | 100 | 100 |
| PIK3CG | 100 | 87 |
| PIK4CB | 80 | 100 |
| PIKFYVE | 99 | 77 |
| PIM1 | 59 | 94 |
| PIM2 | 96 | 98 |
| PIM3 | 78 | 78 |
| PIP5K1A | 100 | 88 |
| PIP5K1C | 67 | 69 |
| PIP5K2B | 87 | 100 |
| PIP5K2C | 16 | 71 |
| PKAC-alpha | 70 | 100 |
| PKAC-beta | 66 | 92 |
| PKMYT1 | 90 | 96 |
| PKN1 | 85 | 71 |
| PKN2 | 92 | 92 |
| PKNB(*M. tuberculosis*) | 82 | 100 |
| PLK1 | 41 | 100 |
| PLK2 | 81 | 90 |
| PLK3 | 79 | 98 |
| PLK4 | 40 | 47 |
| PRKCD | 75 | 87 |
| PRKCE | 77 | 64 |
| PRKCH | 95 | 99 |
| PRKCI | 76 | 63 |
| PRKCQ | 94 | 96 |
| PRKD1 | 14 | 73 |
| PRKD2 | 2 | 83 |
| PRKD3 | 9.6 | 78 |
| PRKG1 | 64 | 98 |
| PRKG2 | 58 | 85 |
| PRKR | 95 | 93 |
| PRKX | 92 | 80 |
| PRP4 | 100 | 91 |
| PYK2 | 60 | 76 |
| QSK | 92 | 87 |
| RAF1 | 97 | 72 |
| RET | 100 | 100 |
| RET(M918T) | 99 | 100 |
| RET(V804L) | 97 | 91 |
| RET(V804M) | 99 | 95 |
| RIOK1 | 94 | 94 |
| RIOK2 | 63 | 100 |
| RIOK3 | 98 | 96 |
| RIPK1 | 94 | 92 |
| RIPK2 | 86 | 94 |
| RIPK4 | 69 | 95 |
| RIPK5 | 18 | 79 |
| ROCK1 | 9.1 | 100 |
| ROCK2 | 7.8 | 100 |
| ROS1 | 83 | 69 |
| RPS6KA4(Kin.Dom.1-N-terminal) | 100 | 100 |
| RPS6KA4(Kin.Dom.2-C-terminal) | 0.3 | 100 |
| RPS6KA5(Kin.Dom.1-N-terminal) | 100 | 100 |
| RPS6KA5(Kin.Dom.2-C-terminal) | 10 | 83 |
| RSK1(Kin.Dom.1-N-terminal) | 73 | 76 |
| RSK1(Kin.Dom.2-C-terminal) | 64 | 77 |
| RSK2(Kin.Dom.1-N-terminal) | 78 | 96 |
| RSK2(Kin.Dom.2-C-terminal) | 100 | 100 |
| RSK3(Kin.Dom.1-N-terminal) | 92 | 75 |
| RSK3(Kin.Dom.2-C-terminal) | 12 | 82 |
| RSK4(Kin.Dom.1-N-terminal) | 81 | 100 |
| RSK4(Kin.Dom.2-C-terminal) | 71 | 80 |
| S6K1 | 70 | 100 |
| SBK1 | 86 | 90 |
| SGK | 64 | 100 |
| SgK110 | 100 | 96 |
| SGK2 | 64 | 100 |
| SGK3 | 79 | 100 |
| SIK | 100 | 90 |
| SIK2 | 87 | 95 |
| SLK | 95 | 80 |
| SNARK | 57 | 100 |
| SNRK | 100 | 100 |
| SRC | 100 | 100 |
| SRMS | 80 | 96 |
| SRPK1 | 89 | 85 |
| SRPK2 | 100 | 100 |
| SRPK3 | 96 | 100 |
| STK16 | 60 | 64 |
| STK33 | 17 | 16 |
| STK35 | 85 | 98 |
| STK36 | 98 | 98 |
| STK39 | 26 | 43 |
| SYK | 66 | 68 |
| TAK1 | 59 | 79 |
| TAOK1 | 82 | 100 |
| TAOK2 | 77 | 85 |
| TAOK3 | 94 | 100 |
| TBK1 | 76 | 85 |
| TEC | 100 | 92 |
| TESK1 | 90 | 79 |
| TGFBR1 | 100 | 69 |
| TGFBR2 | 100 | 97 |
| TIE1 | 88 | 100 |
| TIE2 | 82 | 89 |
| TLK1 | 100 | 73 |
| TLK2 | 98 | 88 |
| TNIK | 89 | 94 |
| TNK1 | 81 | 100 |
| TNK2 | 92 | 86 |
| TNNI3K | 91 | 100 |
| TRKA | 86 | 100 |
| TRKB | 100 | 100 |
| TRKC | 93 | 100 |
| TRPM6 | 87 | 97 |
| TSSK1B | 34 | 53 |
| TSSK3 | 30 | 91 |
| TTK | 8.9 | 67 |
| TXK | 99 | 85 |
| TYK2(JH1domain-catalytic) | 59 | 100 |
| TYK2(JH2domain-pseudokinase) | 67 | 100 |
| TYRO3 | 80 | 96 |
| ULK1 | 78 | 94 |
| ULK2 | 67 | 93 |
| ULK3 | 95 | 83 |
| VEGFR2 | 63 | 95 |
| VPS34 | 96 | 79 |
| VRK2 | 87 | 100 |
| WEE1 | 100 | 100 |
| WEE2 | 91 | 96 |
| WNK1 | 93 | 100 |
| WNK2 | 91 | 100 |
| WNK3 | 82 | 100 |
| WNK4 | 79 | 100 |
| YANK1 | 100 | 100 |
| YANK2 | 100 | 94 |
| YANK3 | 96 | 71 |
| YES | 90 | 83 |
| YSK1 | 99 | 73 |
| YSK4 | 6.7 | 100 |
| ZAK | 96 | 87 |
| ZAP70 | 38 | 100 |

As shown in Table 7, the compounds of the present invention demonstrated smaller % control than 35% for such kinases as ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK and YSK4. The result above indicates that the compounds of the present invention have the activity of inhibiting the listed enzymes above, confirming the usability of the compounds of the invention for the disease relating to the enzymes listed above.

Therefore, the pyrrolo-pyridine derivative compounds of the present invention can be effectively used as a pharmaceutical composition for the treatment or prevention of ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK or YSK4 related disease.

<Experimental Example 7> Evaluation of Tau Phosphorylation Inhibitory Activity of the Compound of the Invention in the Alzheimer's Disease Animal Model The following experiment was performed to investigate the effect of the compound of Example 57 of the present invention on tau phosphorylation in the Alzheimer's disease animal model.

Particularly, 5× FAD mice were administered with the compound of Example 57 of the present invention (20 mg/kg) or vehicle (non-treated group) via i.p. injection every day for 2 weeks. 2 weeks later, immunohistochemistry was performed using AT180, one of Tau phosphorylation antibodies, and as a result confocal microscope images were obtained. Quantitative analysis with the images was performed using image j software. The results are shown in FIG. 6.

FIG. 6 presents the results of the evaluation of Tau phosphorylation inhibitory activity of the compound in the Alzheimer's disease animal model. FIG. 6a: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), AT180: image obtained by immunohistochemistry using AT180 antibody, Merge: image obtained by overlapping DAPI and AT180 images, Enlarge: image obtained by enlarging AT180 image), FIG. 6b: graph illustrating the immunoreactivity of AT180 in the cerebral cortex of the Alzheimer's disease animal model treated with vehicle (untreated group) or the compound of Example 57, FIG. 6c: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), AT180: image obtained by immunohistochemistry using AT180 antibody, Enlarge (CA1): enlarged image of CA1 (cornus aminus, the region where the hippocampus begins and long-term memory is formed) of the hippocampus of AT180 image, Enlarge (DG): enlarged image of DG (dentate gyrus, the region where the hippocampus ends and new memory is formed) of the hippocampus of AT180 image, FIG. 6d: graph illustrating the immunoreactivity of AT180 in the CA1 (cornus aminus) of the Alzheimer's disease animal model treated with vehicle (untreated group) or the compound of Example 57, FIG. 6e: graph illustrating the immunoreactivity of AT180 in the DG (dentate gyrus) of the Alzheimer's disease animal model treated with vehicle (untreated group) or the compound of Example 57

As shown in FIG. 6, it was confirmed that the immunoreactivity of AT180 was significantly reduced in the hippocampus of the mice intraperitoneally administered with 20 mg/kg of the compound of Example of the present invention (vehicle vs #57 (20 mg/kg): *p<0.05, **p<0.001). However, there was no significant change in the immunoreactivity of AT180 in the cerebral cortex region, compared with the group treated with vehicle (non-treated group).

From the above results, it was confirmed that the compound represented by chemical formula 1 of the present invention was able to alleviate the symptoms of Alzheimer's disease.

<Experimental Example 8> Evaluation of Changes of DYRK1A Protein by the Compound of the Invention in the Alzheimer's Disease Animal Model The following experiment was performed to investigate the effect of the compound of Example 57 of the present invention on the target gene DYRK1A protein in the Alzheimer's disease animal model.

Particularly, 5× FAD mice were administered with the compound of Example 57 of the present invention (20 mg/kg) or vehicle (non-treated group) via i.p. injection every day for 2 weeks. 2 weeks later, immunohistochemistry was performed using DYRK1A, and as a result confocal microscope images were obtained. Quantitative analysis with the images was performed using image j software. The results are shown in FIG. 7.

FIG. 7 presents the changes of DYRK1A protein by the compound of the present invention in the Alzheimer's disease animal model. FIG. 7a: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4', 6-diamidino-2-phenylindol), DYRK1A: image obtained by immunohistochemistry using DYRK1A protein, Merge: image obtained by overlapping DAPI and DYRK1A images, Enlarge: image obtained by enlarging DYRK1A image), FIG. 7b: graph illustrating the immunoreactivity of DYRK1A in the cerebral cortex of the Alzheimer's disease animal model treated with vehicle (untreated group) or the compound of Example 57, FIG. 7c: immunofluorescent staining confocal fluorescence photomicrograph of the cerebral cortex of the Alzheimer's disease animal model treated with vehicle (untreated group) or the compound of Example 57 (DAPI: immunofluorescence image staining with DAPI (4',6-diamidino-2-phenylindol), DYRK1A: image obtained by immunohistochemistry using DYRK1A protein, Enlarge (CA1): enlarged image of CA1 (cornus aminus, the region where the hippocampus begins and long-term memory is formed) of the hippocampus of DYRK1A image, Enlarge (DG): enlarged image of DG (dentate gyrus, the region where the hippocampus ends and new memory is formed) of the hippocampus of DYRK1A image, FIG. 7d: graph illustrating the immunoreactivity of DYRK1A in the CA1 (cornus aminus) of the Alzheimer's disease animal model treated with vehicle (untreated group) or the compound of Example 57, FIG. 7e: graph illustrating the immunoreactivity of DYRK1A in the DG (dentate gyrus) of the Alzheimer's disease animal model treated with vehicle (untreated group) or the compound of Example 57 As shown in FIG. 7, it was confirmed that the immunoreactivity of DYRK1A was significantly reduced not only in the cerebral cortex but also in the CA1 and DG regions of the hippocampus in the mice intraperitoneally administered with 20 mg/kg of the compound of Example 57 of the present invention (vehicle vs #57(20 mg/kg): ***p<0.0001).

From the above results, it was confirmed that the compound represented by chemical formula 1 of the present invention was able to alleviate the symptoms of Alzheimer's disease.

<Experimental Example 9> Evaluation of Changes of Amyloid Plaque by the Compound of the Invention in the Alzheimer's Disease Animal Model The following experiment was performed to investigate the effect of the compound of Example 57 of the present invention on amyloid plaque, one of key factors causing Alzheimer's disease, in the Alzheimer's disease animal model.

Particularly, 5× FAD mice were administered with the compound of Example 57 of the present invention (20 mg/kg) or vehicle (non-treated group) via i.p. injection every day for 2 weeks. 2 weeks later, immunohistochemistry was performed using 4G8 antibody capable of detecting amyloid plaque, and as a result confocal microscope images were obtained. Quantitative analysis with the images was performed using image j software. The results are shown in FIG. 8.

FIG. 8 presents the changes of amyloid plaque by the compound of Example 57 in the Alzheimer's disease animal model. FIG. 8a: immunofluorescent staining confocal fluorescence photomicrograph of the cerebral cortex and the hippocampus of the Alzheimer's disease animal model treated with vehicle (untreated group) or the compound of Example 57 (DAPI: immunofluorescence image staining with DAPI (4',6-diamidino-2-phenylindol), 4G8: image obtained by immunohistochemistry using 4G8 antibody, Merge: image obtained by overlapping DAPI and 4G8 images), FIG. 8b: graph illustrating the changes in the number of amyloid plaque of 4G8 in the cerebral cortex of the Alzheimer's disease animal model treated with vehicle (untreated group) or the compound of Example 57, FIG. 8c: graph illustrating the changes in the number of amyloid plaque of 4G8 in the CA1 (cornus aminus) of the Alzheimer's disease animal model treated with vehicle (untreated group) or the compound of Example 57, FIG. 8d: graph illustrating the changes in the number of amyloid plaque of 4G8 in the DG (dentate gyrus) of the Alzheimer's disease animal model treated with vehicle (untreated group) or the compound of Example 57

As shown in FIG. 8, it was confirmed that the number of amyloid plaque was significantly reduced not only in the cerebral cortex but also in the DG region of the hippocampus in the mice intraperitoneally administered with 20 mg/kg of the compound of Example of the present invention (vehicle vs 20 mg/kg: ***p<0.0001). However, in the CA region of the hippocampus, the number of amyloid plaque was not much reduced, compared with the non-treated group.

From the above results, it was confirmed that the compound represented by chemical formula 1 of the present invention was able to alleviate the symptoms of Alzheimer's disease.

<Experimental Example 10> Evaluation of Short Term Cognitive Improvement Effect of the Compound of the Invention Through Behavioral Test (Y-Maze)

The following experiment was performed to investigate whether the compound of Example 57 of the present invention was able to improve short term cognitive function in the Alzheimer's disease animal model.

Particularly, 5× FAD mice were administered with the compound of Example 57 of the present invention (20 mg/kg) or vehicle (non-treated group) via i.p. injection every day for 2 weeks. Then, the mice were placed in Y-maze composed of three arms abutting 120°, and each arm was lifted sequentially for five minutes to calculate the number of alternation triplets to see how well the mice remembered where they visited.

Figure 9A:
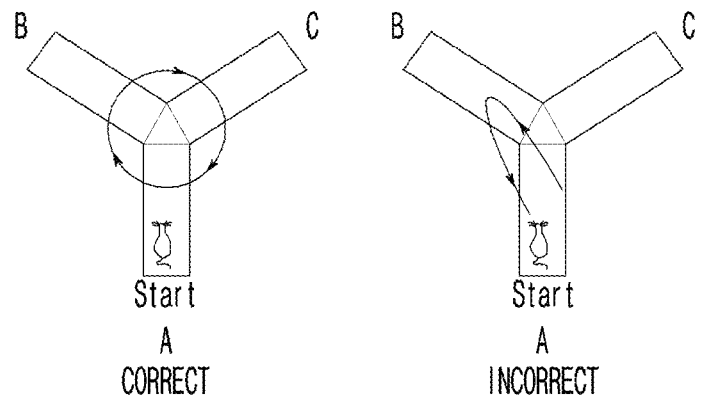
FIG. 9a: schematic diagram of Y-maze to measure the short term memory of the brain.

The equipment used for Y-maze test is composed of three arms. The length of each arm was 42 cm, the width thereof was 3 cm and the height was 12 cm. The angle of contact between the three arms is 120°. All experimental devices were made of black polyvinyl plastic. Each arm was assigned with A, B and C. A test mouse was carefully located in one arm and let move freely for 8 minutes. Then, the arm which the test mouse entered was recorded. At this time, the 'enter' means the case when the mouse tail was completely in. If the mouse entered an arm where it had already visited, the case was also recorded. If the mouse entered three different arms one by one (actual alternation), one point was given. Alternation behavior was defined by that the mouse entered three different arms stepwise, which was calculated by the following equation. FIG. 9a shows the schematic diagram of Y-maze, and FIG. 9b presents the calculation results.

[alternation behavior (%)=actual alternation/*maximum alternation×100]

*maximum alternation: total entries−2

Figure 9B:
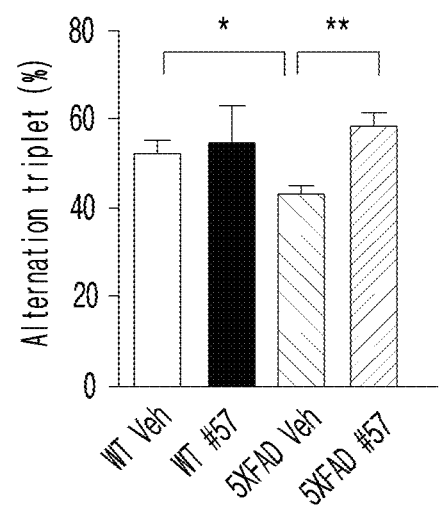
FIG. 9b: graph illustrating the behavioral changes of the mouse tested with Y-maze

FIG. 9 presents the results of evaluating short term cognitive improvement effect through behavioral tests. FIG. 9a: schematic diagram of Y-maze to measure the short term memory of the brain, FIG. 9b: graph illustrating the behavioral changes of the mouse tested with Y-maze As shown in FIG. 9, short term memory was declined in the non-treated group (5× FAD mice were administered with vehicle through i.p. injection), compared with the wild type group (wild type mice were administered with vehicle through i.p. injection), confirmed by alteration behavior test above. On the other hand, the experimental group (5× FAD mice were administered with the compound of Example 57 of the present invention at the concentration of 20 mg/kg through i.p. injection) showed improved short term memory, compared with the non-treated group (5× FAD: vehicle vs 20 mg/kg: **p<0.01).

From the above results, it was confirmed that the compound represented by chemical formula 1 of the present invention was able to improve short term cognitive decline caused by Alzheimer's disease.

<Experimental Example 11> Evaluation of Long Term Cognitive Improvement Effect of the Compound of the Invention Through Behavioral Test—Novel Object Recognition Test The following experiment was performed to investigate whether the compound of Example 57 of the present invention was able to improve long term cognitive function in the Alzheimer's disease animal model. Novel object recognition test is an experiment to test the memory of perception of an object. Mice were let to see two identical objects. After a certain period of time had passed (several hours~a week), the mice were let to see a novel object together with the object previously presented. Then, how much those mice were interested in the novel object and studied it was evaluated, leading to the evaluation of long term memory of the previous object.

Figure 10A:
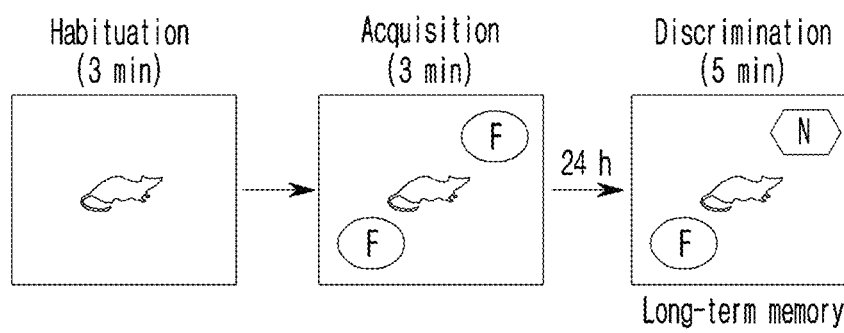
FIG. 10a: schematic diagram of novel object recognition test to measure the long term memory of the brain and equation to calculate novel object preference.

Particularly, 5× FAD mice were administered with the compound of Example 57 of the present invention (20 mg/kg) or vehicle (non-treated group) via i.p. injection every day for 2 weeks. Two objects which were the same in the shape and in the size (F, F) were placed in a specific corner of the open field box (42×42×42 cm) made that the outside is not invisible from the inside, and a test mouse was started from the center of the box. Then, the number and time of the test mouse touching those two objects were recorded for 5 minutes (Acquisition). 24 hours later, one of those two objects was replaced with a new one (F, N). The number and time of access to the original object (F) and the new object (N) were recorded and digitized (Discrimination). Preference for the object (p) was calculated by (time to approach to a certain object)/(total time to approach to two objects). FIG. 10(a) presents the schematic diagram of novel object recognition test, and FIG. 10(b) presents the calculation results.

Figure 10B:
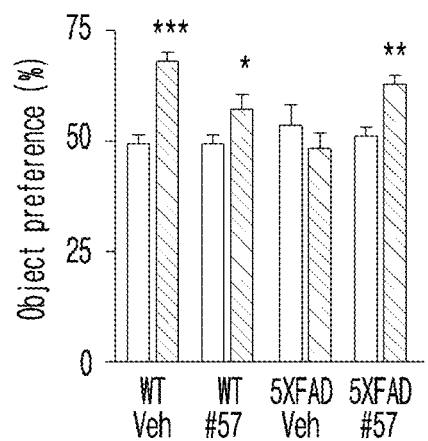
FIG. 10b: graph illustrating the object preference of the test mouse evaluated by novel object recognition test.
Figure 10C:
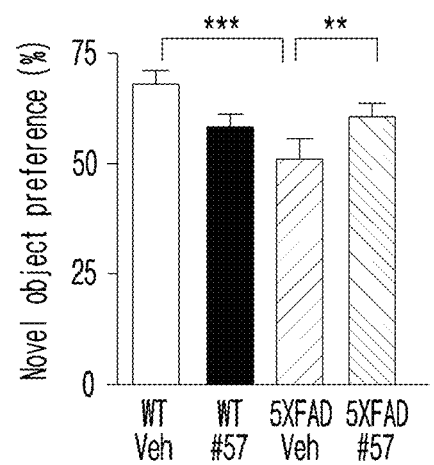
FIG. 10c: graph illustrating the novel object preference of the test mouse evaluated by novel object recognition test

FIG. 10 presents the results of evaluating long term cognitive improvement effect through behavioral tests. FIG. 10a: schematic diagram of novel object recognition test to measure the long term memory of the brain and equation to calculate novel object preference, FIG. 10b: graph illustrating the object preference of the test mouse evaluated by novel object recognition test, FIG. 10c: graph illustrating the novel object preference of the test mouse evaluated by novel object recognition test As shown in FIG. 10, in the stage of discrimination, long term memory measured by preference for the new object was declined in the non-treated group (5× FAD mice were administered with vehicle through i.p. injection), compared with the wild type group (wild type mice were administered with vehicle through i.p. injection). On the other hand, the experimental group (5× FAD mice were administered with the compound of Example 57 of the present invention at the concentration of 20 mg/kg through i.p. injection) showed improved long term memory, compared with the non-treated group (5× FAD: vehicle vs 20 mg/kg: **p<0.01).

From the above results, it was confirmed that the compound represented by chemical formula 1 of the present invention was able to improve long term cognitive decline caused by Alzheimer's disease.

The compound represented by chemical formula 1 of the present invention, the optical isomer thereof or the pharmaceutically acceptable salt thereof was confirmed to have excellent activity to inhibit DYRK1A kinase in Experimental Examples 1 and 2. In addition, the compound represented by chemical formula 1 of the present invention, the optical isomer thereof or the pharmaceutically acceptable salt thereof was confirmed to have excellent activity to inhibit DYRK1A phosphorylation at the cellular level in Experimental Example 3. It was also confirmed in Experimental Example 4 that the compound represented by chemical formula 1 of the present invention, the optical isomer thereof or the pharmaceutically acceptable salt thereof was excellent in inhibiting phosphorylation of Tau, an important factor of Down syndrome. Further, it was also confirmed in Experimental Example 5 that the compound represented by chemical formula 1 of the present invention, the optical isomer thereof or the pharmaceutically acceptable salt thereof had DYRK1A kinase activity inhibiting effect in vivo.

The compound represented by chemical formula 1 of the present invention, the optical isomer thereof or the pharmaceutically acceptable salt thereof was confirmed to have excellent activity to inhibit Tau phosphorylation in the Alzheimer's disease animal model in Experimental Example 7. It was also confirmed in Experimental Example 8 that the compound represented by chemical formula 1 of the present invention, the optical isomer thereof or the pharmaceutically acceptable salt thereof was excellent in inhibiting DYRK1A protein activity. In Experimental Example 9, the compound represented by chemical formula 1 of the present invention, the optical isomer thereof or the pharmaceutically acceptable salt thereof was confirmed to reduce amyloid plaque, one of causes of Alzheimer's disease. In Experimental Example 10, the compound represented by chemical formula 1 of the present invention, the optical isomer thereof or the pharmaceutically acceptable salt thereof was confirmed to improve the short term cognitive decline caused by Alzheimer's disease, and also confirmed to improve the long term cognitive decline caused by Alzheimer's disease in Experimental Example 11.

Therefore, a pharmaceutical composition and a health functional food composition comprising the compound represented by chemical formula 1 of the present invention, the optical isomer thereof or the pharmaceutically acceptable salt thereof can be effectively used for the treatment or prevention of DYRK1A related disease. In particular, they can be effectively used for the prevention, treatment or amelioration of Alzheimer's disease, dementia or Alzheimer's dementia.

INDUSTRIAL APPLICABILITY

The compound represented by chemical formula 1 of the present invention, the optical isomer thereof or the pharmaceutically acceptable salt thereof can be effectively used for the treatment or prevention of protein kinase related disease. In particular, it can be effectively used for the prevention, treatment or amelioration of Alzheimer's disease, dementia or Alzheimer's dementia.

What is claimed is:

1. A compound represented by chemical formula 1 below, an optical isomer thereof or a pharmaceutically acceptable salt thereof:

[Chemical Formula 1]

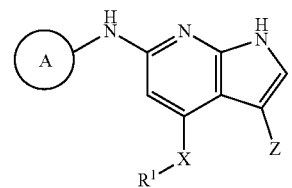

In chemical formula 1,

Z is cyano (—CN); or straight or branched $C_1$-$C_3$ alkyl substituted with one or more halogens;

X is —$NR^a$—, —O— or —S—, wherein $R^a$ is hydrogen or straight or branched $C_1$-$C_{10}$ alkyl, wherein, the alkyl can be substituted with one or more substituents selected from the group consisting of —OH and $C_1$-$C_3$ alkoxy;

$R^1$ is straight or branched $C_1$-$C_{10}$ alkyl, $C_3$-$C_8$ cycloalkyl or $C_{6-14}$ aryl, wherein, the alkyl or cycloalkyl can be substituted with one or more substituents selected from the group consisting of —OH, and, straight or branched $C_1$-$C_3$ alkyl and $C_1$-$C_3$ alkoxy, and the aryl can be substituted with one or more substituents selected from the group consisting of straight or branched $C_1$-$C_3$ alkyl and straight or branched $C_1$-$C_3$ alkoxy, nonsubstituted or substituted with one or more halogens;

or, $R^a$ can form nonsubstituted or substituted 5-8 membered heterocycloalkyl containing one or more heteroatoms selected from the group consisting of N, O and S along with $R^1$ and nitrogen atom to which they are attached, and the substituted heterocycloalkyl can be substituted with one or more substituents selected from the group consisting of straight or branched $C_1$-$C_6$ alkyl and straight or branched $C_1$-$C_6$ alkoxy; and

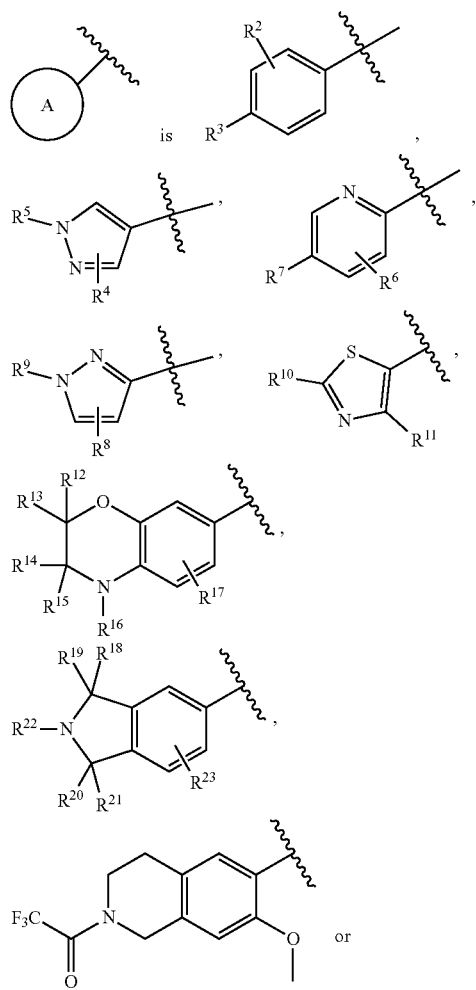

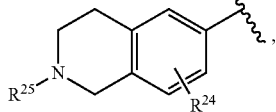

wherein, each $R^2$, $R^4$, $R^6$, $R^8$, $R^{11}$, $R^{17}$, $R^{23}$ and $R^{24}$ are independently one or more substituents selected from the group consisting of hydrogen, halogen, straight or branched $C_1$-$C_6$ alkyl and straight or branched $C_1$-$C_6$ alkoxy;

$R^3$, $R^5$, $R^7$ and $R^9$ are independently hydrogen; straight or branched $C_1$-$C_6$ alkyl or alkoxy; 3-8 membered heterocycloalkyl containing one or more heteroatoms selected from the group consisting of N and O; or —(C═O)$NR^{26}R^{27}$, wherein $R^{26}$ and $R^{27}$ are independently hydrogen, straight or branched $C_1$-$C_3$ alkyl or 3-8 membered heterocycloalkyl containing one or more heteroatoms selected from the group consisting of N and O substituted with 3-5 membered heterocycloalkyl containing one or more oxygen atoms, or, $R^{26}$ and $R^{27}$ form 3-8 membered heterocycloalkyl containing one or more heteroatoms selected from the group consisting of N and O along with nitrogen atom to which they are attached, wherein, the alkyl or heterocycloalkyl is substituted with one or more substituents selected from the group consisting of —CN, halogen, straight or branched $C_1$-$C_3$ alkyl, and, 3-6 membered heterocycloalkyl containing one or more heteroatoms selected from the group consisting of N and O nonsubstituted or substituted with one or more straight or branched $C_1$-$C_3$ alkyl $R^{10}$ is —$CR^{28}R^{29}$—CN, wherein $R^{28}$ and $R^{29}$ are independently hydrogen or straight or branched $C_1$-$C_3$ alkyl, $R^{12}$, $R^{13}$, $R^{14}$, $R^{15}$, $R^{18}$, $R^{19}$, $R^{20}$ and $R^{21}$ are independently hydrogen or straight or branched $C_1$-$C_3$ alkyl, or, two of $R^{12}$, $R^{13}$, $R^{14}$, $R^{15}$, $R^{18}$, $R^{19}$, $R^{20}$ and $R^{21}$ bonded to the same carbon can form carbonyl along with the carbon to which they are attached, and $R^{16}$, $R^{22}$ and $R^{25}$ are independently hydrogen or straight or branched $C_1$-$C_3$ alkyl, wherein the alkyl can be substituted with one or more halogens.

2. The compound, the optical isomer thereof or the pharmaceutically acceptable salt thereof according to claim 1, wherein:

Z is —CN or methyl substituted with one or more halogens;

X is —$NR^a$— or —O—, wherein $R^a$ is hydrogen or straight or branched $C_1$-$C_6$ alkyl, wherein, the alkyl can be substituted with one or more substituents selected from the group consisting of —OH and $C_1$-$C_3$ alkoxy;

$R^1$ is straight or branched $C_1$-$C_6$ alkyl, $C_3$-$C_8$ cycloalkyl or $C_{6-10}$ aryl, wherein, the alkyl can be substituted with one or more substituents selected from the group consisting of —OH, methyl and methoxy, and the aryl can be substituted with one or more substituents selected from the group consisting of methyl and methoxy, nonsubstituted or substituted with one or more halogens;

or, $R^a$ can form nonsubstituted or substituted 5-6 membered heterocycloalkyl containing one or more heteroatoms selected from the group consisting of N, O and S along with $R^1$ and nitrogen atom to which they are attached, and the substituted heterocycloalkyl can be substituted with one or more substituents selected from the group consisting of straight or branched $C_1$-$C_3$ alkyl and straight or branched $C_1$-$C_3$ alkoxy; and

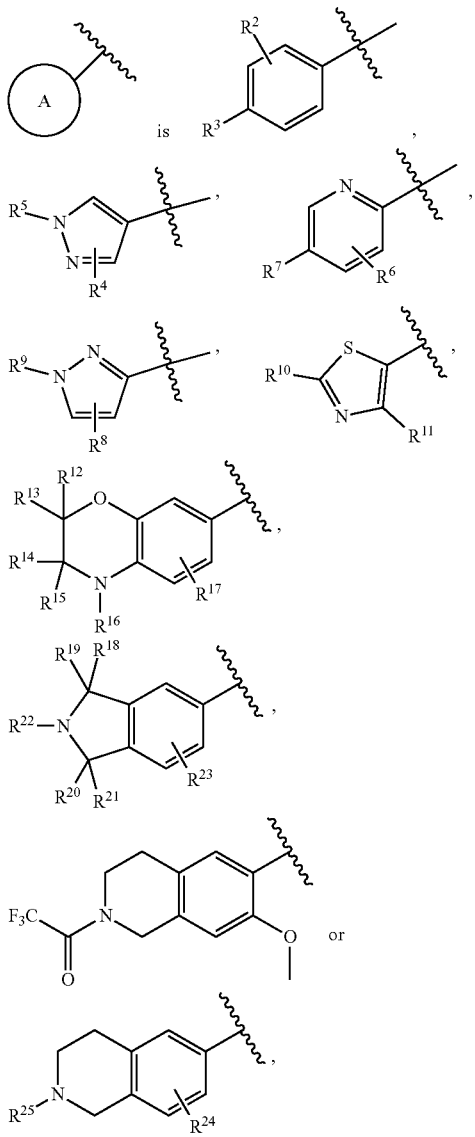

wherein, $R^2$, $R^4$, $R^6$, $R^8$, $R^{11}$, $R^{17}$, $R^{23}$ and $R^{24}$ are independently one or more substituents selected from the group consisting of hydrogen, halogen, straight or branched $C_1$-$C_3$ alkyl and straight or branched $C_1$-$C_3$ alkoxy;

$R^3$, $R^5$, $R^7$ and $R^9$ are independently hydrogen, straight or branched $C_1$-$C_3$ alkyl or alkoxy, morpholinyl, piperazinyl, piperidinyl or —(C=O)NR$^{26}$R$^{27}$, wherein $R^{26}$ and $R^{27}$ are independently hydrogen, methyl, morpholinyl, piperazinyl or piperidinyl, or, $R^{26}$ and $R^{27}$ form morpholinyl, piperazinyl or piperidinyl along with nitrogen atom to which they are attached, wherein, the $C_1$-$C_3$ alkyl, morpholinyl, piperazinyl or piperidinyl can be substituted with one or more substituents selected from the group consisting of —CN, fluoro, oxetanyl, morpholinyl, piperazinyl, and, nonsubstituted or methyl substituted piperidinyl, $R^{10}$ is —CR$^{28}$R$^{29}$—CN, wherein $R^{28}$ and $R^{29}$ are independently hydrogen, methyl or ethyl, $R^{12}$, $R^{13}$, $R^{14}$, $R^{15}$, $R^{18}$, $R^{19}$, $R^{20}$ and $R^{21}$ are independently hydrogen, methyl or ethyl, or, two of $R^{12}$, $R^{13}$, $R^{14}$, $R^{15}$, $R^{18}$, $R^{19}$, $R^{20}$ and $R^{21}$ bonded to the same carbon can form carbonyl along with the carbon to which they are attached, and $R^{16}$, $R^{22}$ and $R^{25}$ are independently hydrogen, methyl nonsubstituted or substituted with one or more halogens or ethyl nonsubstituted or substituted with one or more halogens.

3. The compound, the optical isomer thereof or the pharmaceutically acceptable salt thereof according to claim 1, wherein:

Z is —CN or —CF$_3$;

X is —NR$^a$— or —O—, wherein R$^a$ is hydrogen or methyl;

$R^1$ is methyl, ethyl, n-propyl, isopropyl, cyclopropyl,

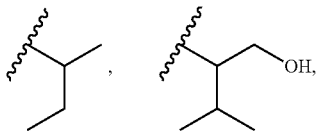

1-methylcyclopropyl, or, phenyl substituted with one or more CF$_3$;

or, R$^a$ can form morpholinyl along with $R^1$ and nitrogen atom to which they are attached; and

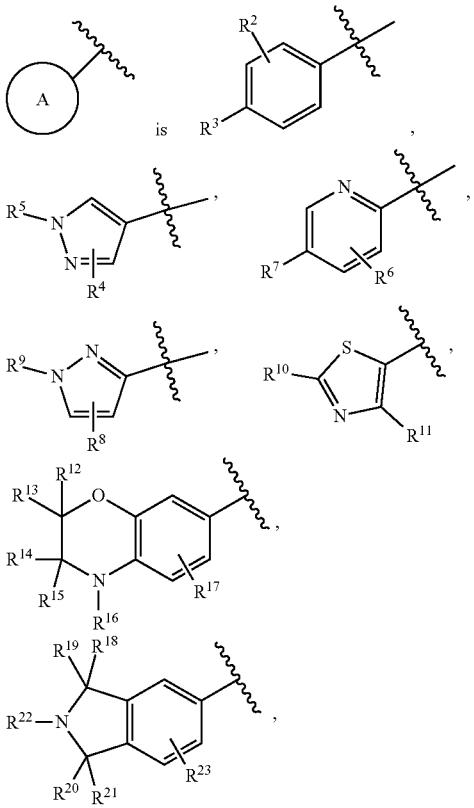

-continued

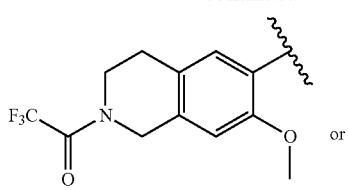
or
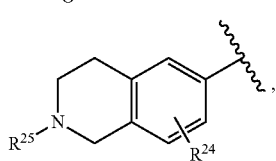, wherein, $R^2$, $R^4$, $R^6$, $R^8$, $R^{11}$, $R^{17}$, $R^{23}$ and $R^{24}$ are independently one or more substituents selected from the group consisting of hydrogen, chloro, fluoro, methyl and methoxy;

$R^3$ and $R^7$ are independently methoxy,

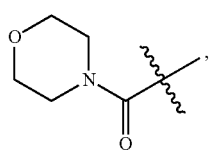, 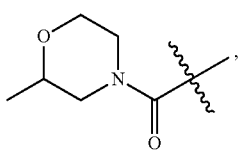,

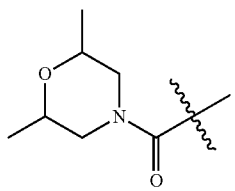, 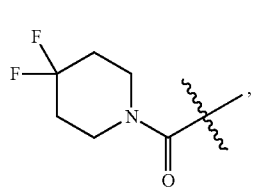,

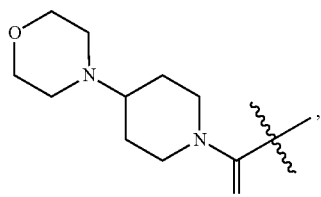,

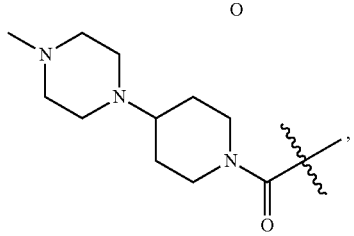,

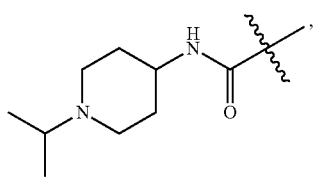

or 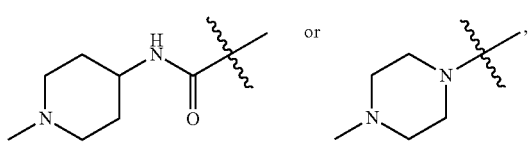, $R^5$ and $R^9$ are independently methyl, isopropyl,

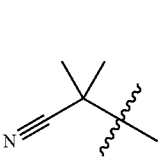 or 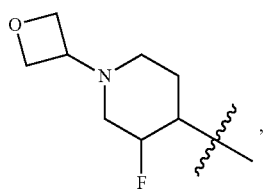, $R^{10}$ is —$CR^{28}R^{29}$—CN, wherein $R^{28}$ and $R^{29}$ are independently hydrogen or methyl, $R^{12}$, $R^{13}$, $R^{14}$, $R^{15}$, $R^{18}$, $R^{19}$, $R^{20}$ and $R^{21}$ are independently hydrogen or methyl, or, two of $R^{12}$, $R^{13}$, $R^{14}$, $R^{15}$, $R^{18}$, $R^{19}$, $R^{20}$ and $R^{21}$ bonded to the same carbon can form carbonyl along with the carbon to which they are attached, and $R^{16}$, $R^{22}$ and $R^{25}$ are independently hydrogen, or, methyl nonsubstituted or substituted with one or more halogens.

4. The compound, the optical isomer thereof or the pharmaceutically acceptable salt thereof according to claim 1, wherein:

Z is —CN or —$CF_3$;

X is —$NR^a$— or —O—, wherein $R^a$ is hydrogen or methyl;

$R^1$ is methyl, ethyl, n-propyl, isopropyl, cyclopropyl,

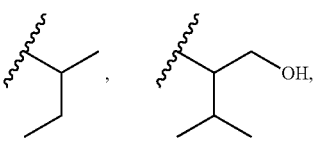, 1-methylcyclopropyl, or

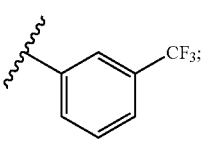;

or, $R^a$ can form morpholinyl along with $R^1$ and nitrogen atom to which they are attached; and

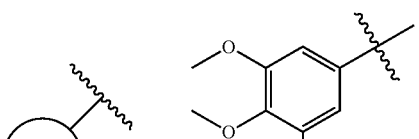

is 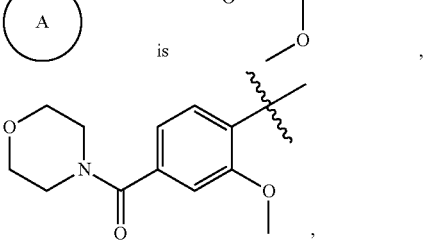,

107
-continued
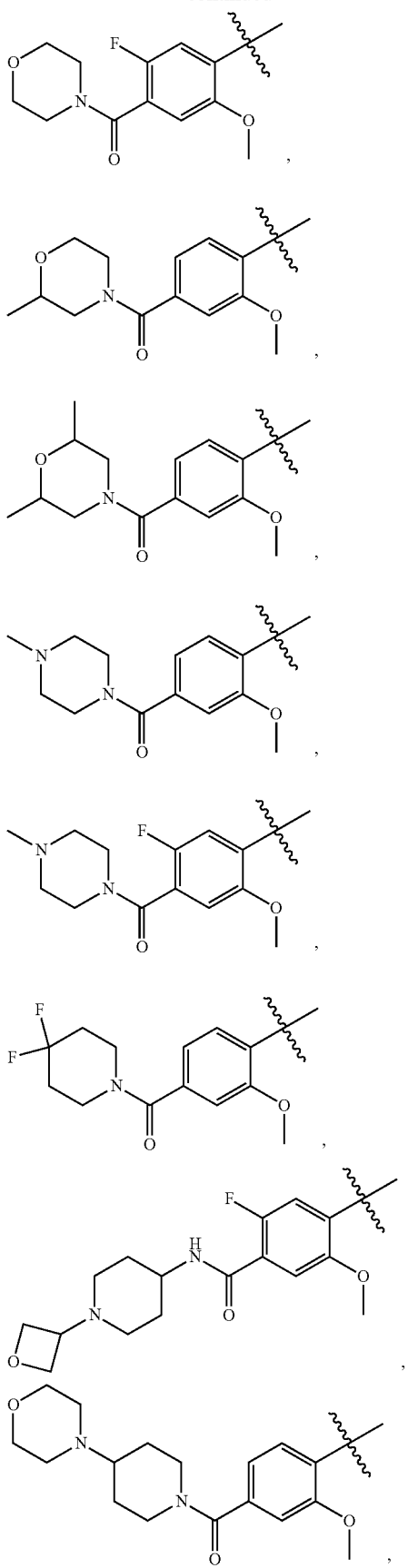
108
-continued
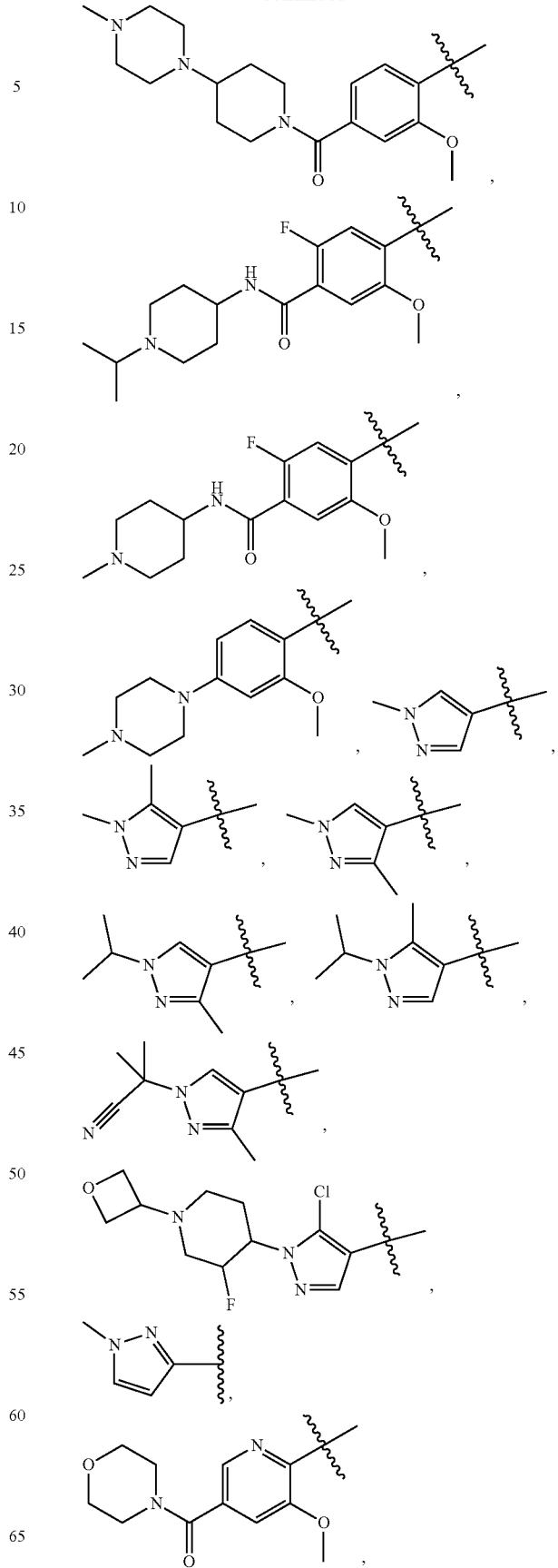

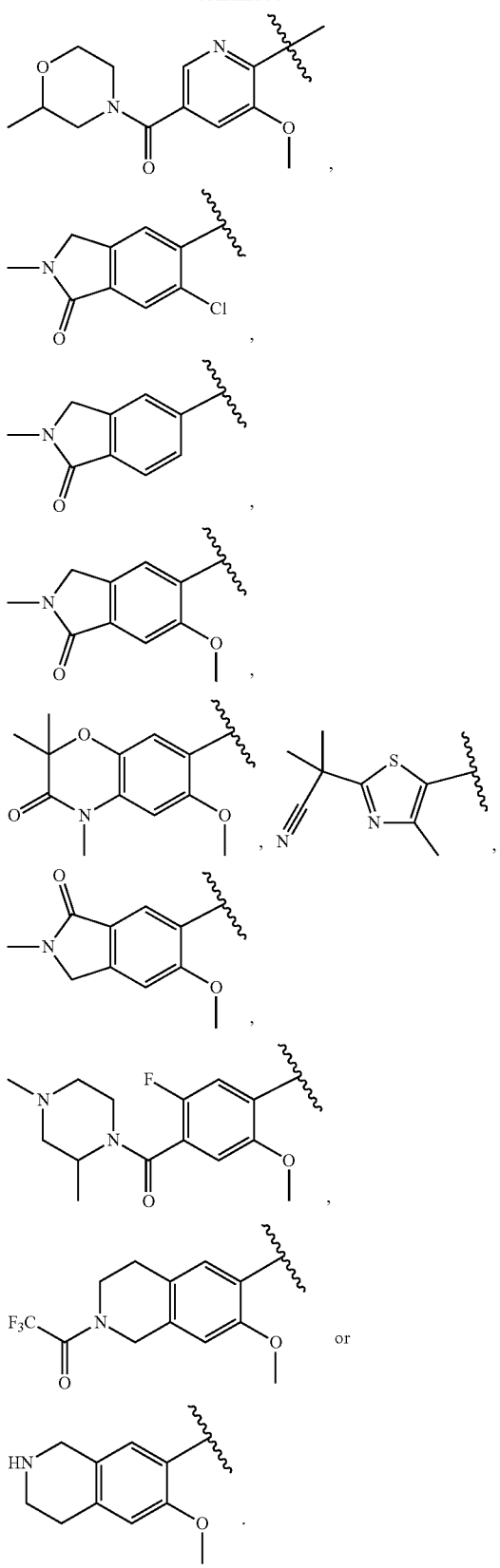

1, wherein the compound represented by chemical formula 1 is selected from the group consisting of the following compounds:

(1) 6-((2-methoxy-4-(morpholine-4-carbonyl)phenyl) amino)-4-(methylamino)-1H-pyrrolo[2,3-b]pyridine-3-carbonitrile;

(2) 4-(ethylamino)-6-((2-methoxy-4-(morpholine-4-carbonyl)phenyl)amino)-1H-pyrrolo[2,3-b]pyridine-3-carbonitrile;

(3) 6-((2-methoxy-4-(4-morpholinopiperidine-1-carbonyl)phenyl)amino)-4-((2-methoxyethyl)amino)-1H-pyrrolo[2,3-b]pyridine-3-carbonitrile;

(4) 6-((2-methoxy-4-(morpholine-4-carbonyl)phenyl) amino)-4-((2-methoxyethyl)amino)-1H-pyrrolo[2,3-b] pyridine-3-carbonitrile;

(5) 4-((2-methoxyethyl)amino)-6-((3,4,5-trimethoxyphenyl)amino)-1H-pyrrolo[2,3-b]pyridine-3-carbonitrile;

(6) 4-((2-methoxyethyl)amino)-6-((1-methyl-1H-pyrazol-4-yl)amino)-1H-pyrrolo[2,3-b]pyridine-3-carbonitrile;

(7) 4-((2-methoxyethyl)amino)-6-((1-methyl-1H-pyrazol-3-yl)amino)-1H-pyrrolo[2,3-b]pyridine-3-carbonitrile;

(8) 4-(ethylamino)-6-((3,4,5-trimethoxyphenyl)amino)-1H-pyrrolo[2,3-b]pyridine-3-carbonitrile;

(9) 6-((2-methoxy-4-(4-morpholinopiperidine-1-carbonyl)phenyl)amino)-4-(propylamino)-1H-pyrrol o[2,3-b]pyridine-3-carbonitrile;

(10) 6-((2-methoxy-4-(morpholine-4-carbonyl)phenyl) amino)-4-(propylamino)-1H-pyrrolo[2,3-b]pyridine-3-carbonitrile;

(11) 4-(propylamino)-6-((3,4,5-trimethoxyphenyl) amino)-1H-pyrrolo[2,3-b]pyridine-3-carbonitrile;

(12) 6-(1-methyl-1H-pyrazol-4-yl)amino)-4-(propylamino)-1H-pyrrolo[2,3-b]pyridine-3-carbonitrile;

(13) 6-(1-methyl-1H-pyrazol-3-yl)amino)-4-(propylamino)-1H-pyrrolo[2,3-b]pyridine-3-carbonitrile;

(14) 4-(ethylamino)-6-((1-methyl-1H-pyrazol-4-yl) amino)-1H-pyrrolo[2,3-b]pyridine-3-carbonitrile;

(15) 4-(ethylamino)-6-((1-methyl-1H-pyrazol-3-yl) amino)-1H-pyrrolo[2,3-b]pyridine-3-carbonitrile;

(16) 6-((2-methoxy-4-(4-morpholinopiperidine-1-carbonyl)phenyl)amino)-4-(methylamino)-1H-pyrrolo[2,3-b]pyridine-3-carbonitrile;

(17) 6-((5-fluoro-2-methoxy-4-(4-morpholinopiperidine-1-carbonyl)phenyl)amino)-4-(methylamino)-1H-pyrrolo[2,3-b]pyridine-3-carbonitrile;

(18) 4-(ethylamino)-6-((2-methoxy-4-(4-morpholinopiperidine-1-carbonyl)phenyl)amino)-1H-pyrrolo[2,3-b] pyridine-3-carbonitrile;

(19) 6-((5-fluoro-2-methoxy-4-(morpholine-4-carbonyl) phenyl)amino)-4-(methylamino)-1H-pyrrolo[2,3-b] pyridine-3-carbonitrile;

(20) 6-((2-methoxy-4-(morpholine-4-carbonyl)phenyl) amino)-4-((2-methoxyethyl)(methyl)amino)-1H-pyrrolo[2,3-b]pyridine-3-carbonitrile;

(21) 6-((5-fluoro-2-methoxy-4-(morpholine-4-carbonyl) phenyl)amino)-4-((2-methoxyethyl)(methyl)amino)-1H-pyrrolo[2,3-b]pyridine-3-carbonitrile;

(22) (R)-6-((2-methoxy-4-(2-methylmorpholine-4-carbonyl)phenyl)amino)-4-(methylamino)-1H-pyrrolo[2,3-b]pyridine-3-carbonitrile;

(23) (S)-6-((2-methoxy-4-(2-methylmorpholine-4-carbonyl)phenyl)amino)-4-(methylamino)-1H-pyrrolo[2,3-b]pyridine-3-carbonitrile;

5. The compound, the optical isomer thereof or the pharmaceutically acceptable salt thereof according to claim

(24) 6-((4-((2R,6S)-2,6-dimethylmorpholine-4-carbonyl)-2-methoxyphenyl)amino)-4-(methylamino)-1H-pyrrolo[2,3-b]pyridine-3-carbonitrile;
(25) 6-((4-(4,4-difluoropiperidine-1-carbonyl)-2-methoxyphenyl)amino)-4-(methylamino)-1H-pyrrolo[2,3-b]pyridine-3-carbonitrile;
(26) (R)-4-(ethylamino)-6-((2-methoxy-4-(2-methylmorpholine-4-carbonyl)phenyl)amino)-1H-pyrrolo[2,3-b]pyridine-3-carbonitrile;
(27) (S)-4-(ethylamino)-6-((2-methoxy-4-(2-methylmorpholine-4-carbonyl)phenyl)amino)-1H-pyrrolo[2,3-b]pyridine-3-carbonitrile;
(28) 6-((4-((2R,6S)-2,6-dimethylmorpholine-4-carbonyl)-2-methoxyphenyl)amino)-4-(ethylamino)-1H-pyrrolo[2,3-b]pyridine-3-carbonitrile;
(29) 6-((4-(4,4-difluoropiperidine-1-carbonyl)-2-methoxyphenyl)amino)-4-(ethylamino)-1H-pyrrolo[2,3-b]pyridine-3-carbonitrile;
(30) 6-((1,3-dimethyl-1H-pyrazol-4-yl)amino)-4-(ethylamino)-1H-pyrrolo[2,3-b]pyridine-3-carbonitrile;
(31) 6-((1,5-dimethyl-1H-pyrazol-4-yl)amino)-4-(ethylamino)-1H-pyrrolo[2,3-b]pyridine-3-carbonitrile;
(32) 4-(ethylamino)-6-((1-isopropyl-3-methyl-1H-pyrazol-4-yl)amino)-1H-pyrrolo[2,3-b]pyridine-3-carbonitrile;
(33) 4-(ethylamino)-6-((1-isopropyl-5-methyl-1H-pyrazol-4-yl)amino)-1H-pyrrolo[2,3-b]pyridine-3-carbonitrile;
(34) 6-((1,5-dimethyl-1H-pyrazol-4-yl)amino)-4-(methylamino)-1H-pyrrolo[2,3-b]pyridine-3-carbonitrile;
(35) 6-((1,3-dimethyl-1H-pyrazol-4-yl)amino)-4-(methylamino)-1H-pyrrolo[2,3-b]pyridine-3-carbonitrile;
(36) 6-((1-isopropyl-3-methyl-1H-pyrazol-4-yl)amino)-4-(methylamino)-1H-pyrrolo[2,3-b]pyridine-3-carbonitrile;
(37) 6-((1-isopropyl-5-methyl-1H-pyrazol-4-yl)amino)-4-(methylamino)-1H-pyrrolo[2,3-b]pyridine-3-carbonitrile;
(38) 6-((1-(2-cyanopropan-2-yl)-3-methyl-1H-pyrazol-4-yl)amino)-4-(methylamino)-1H-pyrrolo[2,3-b]pyridine-3-carbonitrile;
(39) 6-((3-methoxy-5-(morpholine-4-carbonyl)pyridin-2-yl)amino)-4-(methylamino)-1H-pyrrolo[2,3-b]pyridine-3-carbonitrile;
(40) 4-(ethylamino)-6-((3-methoxy-5-(morpholine-4-carbonyl)pyridin-2-yl)amino)-1H-pyrrolo[2,3-b]pyridine-3-carbonitrile;
(41) 6-((5-chloro-1-((3 S,4S)-3-fluoro-1-(oxetan-3-yl)piperidin-4-yl)-1H-pyrazol-4-yl)amino)(methylamino)-1H-pyrrolo[2,3-b]pyridine-3-carbonitrile;
(42) 6-((5-chloro-1-((3 S,4S)-3-fluoro-1-(oxetan-3-yl)piperidin-4-yl)-1H-pyrazol-4-yl)amino)(ethylamino)-1H-pyrrolo[2,3-b]pyridine-3-carbonitrile;
(43) (R)-4-(ethylamino)-6-((3-methoxy-5-(2-methylmorpholine-4-carbonyl)pyridin-2-yl)amino)-1H-pyrrolo[2,3-b]pyridine-3-carbonitrile;
(44) (R)-6-((3-methoxy-5-(2-methylmorpholine-4-carbonyl)pyridin-2-yl)amino)-4-(methylamino)-1H-pyrrolo[2,3-b]pyridine-3-carbonitrile;
(45) (5-methoxy-6-(4-(methylamino)-3-(trifluromethyl)-1H-pyrrolo[2,3-b]pyridin-6-ylamino)pyridin-3-yl)(4-methylpiperazin-1-yl)methanone;
(46) (3-methoxy-4-((4-morpholino-3-(trifluoromethyl)-1H-pyrrolo[2,3-b]pyridin-6-yl)amino)phenyl)(4-(4-methylpiperazin-1-yl)piperidin-1-yl)methanone;
(47) 4-methoxy-6-((2-methoxy-4-(4-morpholinopiperidine-1-carbonyl)phenyl)amino)-1H-pyrrolo[2,3-b]pyridine-3-carbonitrile;
(48) 4-methoxy-6-((2-methoxy-4-(morpholine-4-carbonyl)phenyl)amino)-1H-pyrrolo[2,3-b]pyridine-3-carbonitrile;
(49) 4-ethoxy-6-((2-methoxy-4-(4-morpholinopiperidine-1-carbonyl)phenyl)amino)-1H-pyrrolo[2,3-b]pyridine-3-carbonitrile;
(50) 4-ethoxy-6-((2-methoxy-4-(morpholine-4-carbonyl)phenyl)amino)-1H-pyrrolo[2,3-b]pyridine-3-carbonitrile;
(51) (R)-6-((3-methoxy-5-(2-methylmorpholine-4-carbonyl)pyridin-2-yl)amino)-4-(1-methylcyclopropoxy)-1H-pyrrolo[2,3-b]pyridine-3-carbonitrile;
(52) 6-((3-methoxy-5-(morpholine-4-carbonyl)pyridin-2-yl)amino)-4-(1-methylcyclopropoxy)-1H-pyrrolo[2,3-b]pyridine-3-carbonitrile;
(53) $N^4$-ethyl-3-(trifluoromethyl)-$N^6$-(3,4,5-trimethoxyphenyl)-1H-pyrrolo[2,3-b]pyridine-4,6-diamine;
(54) $N^4$-ethyl-$N^6$-(1-methyl-1H-pyrazol-3-yl)-3-(trifluoromethyl)-1H-pyrrolo[2,3-b]pyridine-4,6-diamine;
(55) $N^4$-ethyl-$N^6$-(1-methyl-1H-pyrazol-4-yl)-3-(trifluoromethyl)-1H-pyrrolo[2,3-b]pyridine-4,6-diamine;
(56) (4-((4-(ethylamino)-3-(trifluoromethyl)-1H-pyrrolo[2,3-b]pyridin-6-yl)amino)-3-methoxyphenyl)(morpholino)methanone;
(57) (4-((4-(ethylamino)-3-(trifluoromethyl)-1H-pyrrolo[2,3-b]pyridin-6-yl)amino)-3-methoxyphenyl)(4-morpholinopiperidin-1-yl)methanone;
(58) (3-methoxy-4-((4-(methylamino)-3-(trifluoromethyl)-1H-pyrrolo[2,3-b]pyridin-6-yl)amino)phenyl)(morpholino)methanone;
(59) (3-methoxy-4-((4-(methylamino)-3-(trifluoromethyl)-1H-pyrrolo[2,3-b]pyridin-6-yl)amino)phenyl)(4-morpholinopiperidin-1-yl)methanone;
(60) (2-fluoro-5-methoxy-4-((4-(methylamino)-3-(trifluoromethyl)-1H-pyrrolo[2,3-b]pyridin-6-yl)amino)phenyl)(4-methylpiperazin-1-yl)methanone;
(61) (3-methoxy-4-((4-(methylamino)-3-(trifluoromethyl)-1H-pyrrolo[2,3-b]pyridin-6-yl)amino)phenyl)(4-(4-methylpiperazin-1-yl)piperidin-1-yl)methanone;
(62) $N^6$-(2-methoxy-4-(4-methylpiperazin-1-yl)phenyl)-$N^4$-methyl-3-(trifluoromethyl)-1H-pyrrolo[2,3-b]pyridine-4,6-diamine;
(63) (3-methoxy-4-((4-(methylamino)-3-(trifluoromethyl)-1H-pyrrolo[2,3-b]pyridin-6-yl)amino)phenyl)(4-methylpiperazin-1-yl)methanone;
(64) (3-methoxy-4-((4-((2-methoxyethyl)amino)-3-(trifluoromethyl)-1H-pyrrolo[2,3-b]pyridine-6yl)amino)phenyl)(morpholino)methanone;
(65) (3-methoxy-4-((4-((2-methoxyethyl)amino)-3-(trifluoromethyl)-1H-pyrrolo[2,3-b]pyridin-6-yl)amino)phenyl)(4-morpholinopiperidin-1-yl)methanone;
(66) (3-methoxy-4-((4-((2-methoxyethyl)amino)-3-(trifluoromethyl)-1H-pyrrolo[2,3-b]pyridin-6-yl)amino)phenyl)(4-methylpiperazin-1-yl)-methanone;
(67) (3-methoxy-4-((4-((2-methoxyethyl)amino)-3-(trifluoromethyl)-1H-pyrrolo[2,3-b]pyridin-6-yl)amino)phenyl)(4-methylpiperazin-1-yl)piperidin-1-yl)methanone;
(68) $N^6$-(2-methoxy-4-(4-methylpiperazin-1-yl)phenyl)-$N^4$-(2-methoxyethyl)-3-(trifluoromethyl)-1H-pyrrolo[2,3-b]pyridine-4,6-diamine;
(69) $N^6$-(5-chloro-1-((3 S,4S)-3-fluoro-1-(oxetan-3-yl)piperidin-4-yl)-1H-pyrazol-4-yl)-N4-ethyl-3-(trifluoromethyl)-1H-pyrrolo[2,3-b]pyridine-4,6-diamine;

(70) (4-(ethylamino)-3-(trifluoromethyl)-1H-pyrrolo[2,3-b]pyridin-6-yl)amino)-3-methoxyphenyl)(4-(4-methylpiperazin-1-yl)piperidin-1-yl)methanone;

(71) 4-((4-(ethylamino)-3-(trifluoromethyl)-1H-pyrrolo[2,3-b]pyridin-6-yl)amino)-2-fluoro-5methoxy-N-(1-(oxetanepiperidin-4-yl)benzamide;

(72) 4-((4-(ethylamino)-3-(trifluoromethyl)-1H-pyrrolo[2,3-b]pyridin-6-yl)amino)-2-fluoro-5-methoxy-N-(1-methylpiperidin-4-yl)benzylamide;

(73) 2-fluoro-5-methoxy-4-((4-((2-methoxyethyl)amino)-3-(trifluoromethyl)-1H-pyrrolo[2,3-b]pyridin-6-yl)amino)(1-methylpiperidin-4-yl)benzamide;

(74) 4-((4-(ethylamino-3-(trifluoromethyl)-1H-pyrrolo[2,3-b]pyridin-6-yl)amino)-2-fluoro-N-(1-isopropylpiperidin-4-yl)-5-methoxybenzamide;

(75) (R)-(2,4-dimethylpiperazin-1-yl)(2-fluoro-5-methoxy-4-((4-(methylamino)-3-(trifluoromethyl)-1H-pyrrolo[2,3-b]pyridin-6-yl)amino)phenyl)methanone;

(76) (3-methoxy-4-((4-morpholino-3-(trifluoromethyl)-1H-pyrrolo[2,3-b]pyridin-6-yl)amino)phenyl)(morpholino)methanone;

(77) N-(5-chloro-1-((3 S,4S)-3-fluoro-1-(oxetan-3-yl)piperidin-4-yl)-1H-pyrazol-4-yl)-4-morpholino-3-(trifluoromethyl)-1H-pyrrolo[2,3-b]pyridine-6-amine;

(78) N6-(5-chloro-1-((3S, 4 S)-3-fluoro-1-(oxetan-3-yl)piperidin-4-yl)-1H-pyrazol-4-yl)-N4-methyl-3-(trifluoromethyl)-1H-pyrrolo[2,3-b]pyridine-4,6-diamine;

(79) N6-(5-chloro-1-((3S, 4 S)-3-fluoro-1-(oxetan-3-yl)piperidin-4-yl)-1H-pyrazol-4-yl)-3-methoxyethyl)-3-(trifluoromethyl)-1H-pyrrolo[2,3-b]pyridine-4,6-diamine;

(80) 1-(6-((4-(ethylamino)-3-(trifluoromethyl)-1H-pyrrolo[2,3-b]pyridin-6-yl)amino)-7-methoxy-3,4-dihydroisoquinolin-2(1H)-yl)-2,2,2-trifluoroethan-1-one;

(81) N4-ethyl-N6-(7-methoxy-1,2,3,4-tetrahydroisoquinolin-6-yl)-3-(trifluoromethyl)-1H-pyrrolo[2,3-b]pyridine-4,6-diamine;

(82) (3-methoxy-4-((4-morpholino-3-(trifluoromethyl)-1H-pyrrolo[2,3-b]pyridin-6-yl)amino)phenyl)(4-methylpiperazin-1-yl)methanone;

(83) (3-methoxy-4-((4-morpholino-3-(trifluoromethyl)-1H-pyrrolo[2,3-b]pyridin-6-yl)amino)phenyl)(4-(4-methylpiperazin-1-yl)piperidin-1-yl)methanone;

(84) (3-methoxy-4-(3-(trifluoromethyl)-4-(3-(trifluoromethyl)phenylamino)-1H-pyrrolo[2,3-b]pyridin-6-ylamino)phenyl)(morpholino)methanone;

(85) (3-methoxy-4-(3-(trifluoromethyl)-4-(3-(trifluoromethyl)phenylamino)-1H-pyrrolo[2,3-b]pyridin-6-ylamino)phenyl)(4-morpholinopiperidin-1-yl)methanone;

(86) N6-(5-chloro-1-((3S, 4S)-3-fluoro-1-(oxetan-3-yl)piperidin-4-yl)-1H-pyrazol-4-yl)-3-(trifluoromethyl)-N4-(3-(trifluoromethyl)phenyl)-1H-pyrrolo[2,3-b]pyridine-4,6-diamine;

(87) (3-methoxy-4-((4-methoxyethyl)(methyl)amino)-3-(trifluoromethyl)-1H-pyrrolo[2,3-b]pyridin-6-yl)amino)phenyl)(morpholino)methanone;

(88) (3-methoxy-4-((4-methoxyethyl)(methyl)amino)-3-(trifluoromethyl)-1H-pyrrolo[2,3-b]pyridin-6-yl)amino)phenyl)((4-morpholinopiperidin-1-yl)methanone;

(89) N6-(5-chloro-1-((3S,4S)-3-fluoro-1-(oxetan-3-yl)piperidin-4-yl)-1H-pyrazol-4-yl)methoxyethyl)-N4-methyl-3-(trifluoromethyl)-1H-pyrrolo[2,3-b]pyridine-4,6-diamine;

(90) (4-(4-(isopropylamino)-3-(trifluoromethyl)-1H-pyrrolo[2,3-b]pyridin-6-ylamino)-3-methoxyphenyl)(4-morpholinopiperidin-1-yl)methanone;

(91) (R)-(4-((4-((1-hydroxy-3-methylbutan-2-yl)amino)-3-(trifluoromethyl)-1H-pyrrolo[2,3-b]amino)-3-methoxyphenyl)(4-morpholinopiperidin-1-yl)methanone;

(92) (R)-(4-((4-((1-hydroxy-3-methylbutan-2-yl)amino)-3-(trifluoromethyl)-1H-pyrrolo[2,3-b]amino)-3-methoxyphenyl)(morpholino)methanone;

(93) (S)-(4-((4-(2-butylamino)-3-(trifluoromethyl)-1H-pyrrolo[2,3-b]pyridin-6-yl)amino)-3-methoxyphenyl)(4-morpholinopiperidin-1-yl)-methanone;

(94) (4-((4-(cyclopropylamino)-3-(trifluoromethyl)-1-((2-(trimethylsilyl)ethoxy)methyl)-1H-pyrrolo[2,3-b]pyridin-6-yl)-3-methoxyphenyl)(4-morpholinopiperidin-1-yl)methanone;

(95) (4-((4-(cyclopropylamino)-3-(trifluoromethyl)-1H-pyrrolo[2,3-b]pyridin-6-yl)amino)-3-methoxyphenyl)(morpholino)methanone;

(96) 5-((4-(ethylamino)-3-(trifluoromethyl)-1H-pyrrolo[2,3-b]pyridin-6-yl)amino)-6-methoxy-2-methylisoindolin-1-one;

(97) 7-((4-(ethylamino)-3-(trifluoromethyl)-1H-pyrrolo[2,3-b]pyridin-6-yl)amino)-6-methoxy-2,2,4-trimethyl-2H-benzo[1,4]oxazin-3(4H)-1-one;

(98) 6-((4-(ethylamino)-3-(trifluoromethyl)-1H-pyrrolo[2,3-b]pyridin-6-yl)amino)-5-methoxy-2-methylisoindolin-1-one;

(99) 4-(ethylamino)-6-((6-methoxy-2-methyl-3-oxoisoindol-5-yl)amino)-1H-pyrrolo[2,3-b]pyridine-3-carbonitrile;

(100) 6-((2(2(2-cyanopropan-2-yl)-4-methylthiazol-5-yl)amino)-4-(ethylamino)-1H-pyrrolo[2,3-b]pyridine-3-carbonitrile;

(101) (6-chloro-5-((4-(ethylamino)-3-(trifluoromethyl)-1H-pyrrolo[2,3-b]pyridin-6-yl)amino)-2-methylisoindolin-1-one;

(102) 5-((4-(ethylamino)-3-(trifluoromethyl)-1H-pyrrolo[2,3-b]pyridin-6-yl)amino)-2-methylisoindolin-1-one;

(103) 4-(ethylamino)-6-((2-methyl-1-oxoisoindol-5-yl)amino)-1H-pyrrolo[2,3-b]pyridine-3-carbonitrile;

(104) 6-((6-chloro-2-methyl-1-oxoisoindolin-5-yl)amino)-4-(ethylamino)-1H-pyrrolo[2,3-b]pyridine-3-carbonitrile; and, (105) 4-(ethylamino)-6-((6-methoxy-2,2,4-trimethyl-3-oxo-3,4-dihydro-2H-benzo[b][1,4]oxazin-7-yl)amino)-1H-pyrrolo[2,3-b]pyridine-3-carbonitrile.

6. A preparation method of a compound represented by of claim 1 comprising the following steps, as shown in reaction formula 1 below:

preparing a compound represented by chemical formula 4 by reacting a compound represented by chemical formula 2 with a compound represented by chemical formula 3 (step 1); and preparing a compound represented by chemical formula 1 by reacting the compound represented by chemical formula 4 prepared in step 1 above in the presence of an acid (step 2):

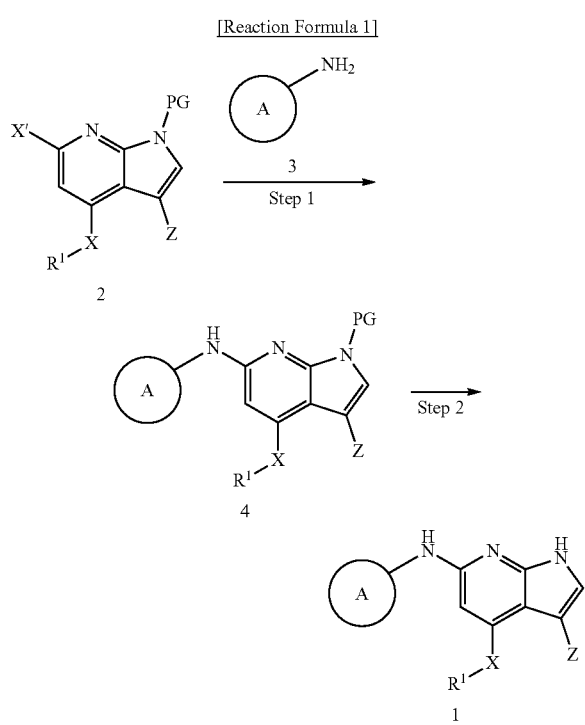

wherein X' is halogen; and
PG is (2-(trimethylsilyl)methoxy)methyl (SEM), t-butyloxycarbonyl (BOC), carbobenzyloxy (Cbz), 9-fluorenylmethyloxycarbonyl (Fmoc), acetyl (Ac), benzoyl (Bz), benzyl (Bn), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), aryloxycarbonyl (Alloc) or p-methoxybenzyl (PMB).

7. A method of treating a subject having degenerative brain disease, comprising administering an effective amount of compound represented by chemical formula 1 of claim 1, the optical isomer thereof or the pharmaceutically acceptable salt thereof to the subject, wherein the degenerative brain disease is selected from the group consisting of Alzheimer's disease, Parkinson's disease, Huntington's disease, or mild cognitive impairment.

8. The method according to claim 7, wherein the compound inhibits protein kinase activity.

9. The method according to claim 8, wherein the protein kinase is one or more enzymes selected from the group consisting of ALK, ALK (C1156Y), ALK (L1196M), CAMK1B, CAMK1D, CHEK2, CLK1, CLK2, CLK3, CLK4, CSNK1A1, CSNK1A1L, CSNK1D, CSNK1E, CSNK1G2, CSNK1G3, DAPK1, DAPK2, DAPK3, DRAK2, DYRK1A, DYRK1B, DYRK2, ERK5, ERN1, GAK, HASPIN, INSRR, JNK1, JNK2, JNK3, KIT (V559D), LATS2, LRRK2, LRRK2 (G2019S), LTK, MAPKAPK2, MEK1, MEK2, MEK3, MEK4, MYLK, NIK, PHKG1, PHKG2, PIP5K2C, PRKD1, PRKD2, PRKD3, RIPK5, ROCK1, ROCK2, RPS6KA4 (Kin.Dom.2-C-terminal), RPS6KA5 (Kin.Dom.2-C-terminal), RSK3 (Kin.Dom.2-C-terminal), STK33, STK39, TSSK1B, TSSK3, TTK and YSK4.

* * * * *